(12) United States Patent
Mkrtchyan et al.

(10) Patent No.: US 10,040,752 B2
(45) Date of Patent: Aug. 7, 2018

(54) SYNTHESIS OF LEVOMETHADONE HYDROCHLORIDE OR DEXTROMETHADONE HYDROCHLORIDE AND METHODS FOR USE THEREOF

(71) Applicant: Cody Laboratories, Inc., Cody, WY (US)

(72) Inventors: Gnel Mkrtchyan, Cody, WY (US); Qingwei Yao, Cody, WY (US)

(73) Assignee: Cody Laboratories, Inc., Cody, WY (US)

( * ) Notice: Subject to any disclaimer, the term of this patent is extended or adjusted under 35 U.S.C. 154(b) by 0 days.

(21) Appl. No.: 15/245,935

(22) Filed: Aug. 24, 2016

(65) Prior Publication Data

US 2017/0057909 A1     Mar. 2, 2017

Related U.S. Application Data

(60) Provisional application No. 62/209,168, filed on Aug. 24, 2015.

(51) Int. Cl.
| | | |
|---|---|---|
| C07C 221/00 | (2006.01) | |
| C07C 225/16 | (2006.01) | |
| C07C 213/00 | (2006.01) | |
| C07C 227/18 | (2006.01) | |
| C07C 253/30 | (2006.01) | |

(52) U.S. Cl.
CPC .......... *C07C 221/00* (2013.01); *C07C 213/00* (2013.01); *C07C 225/16* (2013.01); *C07C 227/18* (2013.01); *C07C 253/30* (2013.01); *C07B 2200/07* (2013.01)

(58) Field of Classification Search
USPC ........................................ 514/663, 646, 649
See application file for complete search history.

(56) References Cited

U.S. PATENT DOCUMENTS

| | | |
|---|---|---|
| 2,497,739 A | 2/1950 | Pfister |
| 2,540,636 A | 2/1951 | Stoughton |
| 2,601,323 A | 6/1952 | Reid et al. |
| 4,048,211 A | 9/1977 | Barnett |
| 4,242,274 A | 12/1980 | Taylor |
| 6,143,933 A | 11/2000 | Scheinmann et al. |
| 2014/0088155 A1 | 3/2014 | Manfredi et al. |
| 2014/0350302 A1 | 11/2014 | Ismail et al. |

FOREIGN PATENT DOCUMENTS

| | | |
|---|---|---|
| GB | 1124682 | 8/1968 |
| WO | 97/45551 | 12/1997 |
| WO | 2012/162635 | 11/2012 |
| WO | 2013/077720 | 5/2013 |

OTHER PUBLICATIONS

Mahmood, Synthesis; 2011, No. 3, 490-496.*
Beckett et al., "Configurational studies in synthetic analgesics: the synthesis of (−)-Methadone from D-(−)-Alanine", Journal of the Chemical Society, vol. 0, No. 0, Jan. 1, 1957, pp. 858-861.
Portoghese et al., "Synthesis, x-ray crystallographic determination, and opioid activity of erythro-5-methylmethadone enantiomers. Evidence which suggests that mu and delta opioid receptors possess different stereochemical requirements," J. Med. Chem., Jan. 1, 1982, vol. 25, No. 6 pp. 684-688.
International Search Report and Written Opinion of the International Searching Authority for PCT/US2016/048380, dated Oct. 21, 2016, 14 pages total.
Moryl et al., "A phase I study of D-methadone in patients with chronic pain," J. Opioid Management, 12:1 Jan./Feb. 2016, pp. 47-55.
Attenburrow et al., "Analgesics. II. The synthesis of amidone and some of its analogs," Journal of the Chemical Society (1949) pp. 510-518.
Barnett et al., "Stereochemistry of Bockmuehl's synthesis of methadone," Journal of Organic Chemistry (1976), 41(4), pp. 710-711.
Amani et al., "Crystal structure of 2,2-diphenyl-4-dimethylaminopentanenitrile, C19H22N2", Zeitschrift fuer Kristallographie—New Crystal Structures (2005), 220(4), pp. 549-550.
Ansermot et al., "Substitution of (R,S)-Methadone by (R)-Methadone", Arch Intern Med, Mar. 22, 2010, 170(6), pp. 529-536.
Schultz et al., "The Preparation and rearrangements of 1,2-dimethylaminochloropropanes," Journal of the American Chemical Society (1948), 70, pp. 48-52.
Brode et al., "Rearrangement of the isomeric 1,2-(dimethylamino)-chloropropanes. The synthesis of amidone," Journal of the American Chemical Society (1947), 69, p. 724.
Bracher et al. "A Novel Approach to Isomeric Pure (±)-Methadone," Sci. Phar., (1996), 64, pp. 271-278. (English language abstract provided).
Poupaert, "Dibenzo-18-crown-6 as phase transfer catalyst in Bockmuehl's synthesis of methadone," Journal of Chemical Research, Synopses (1981), (7), 192.
Berge, et al. "Pharmaceutical Salts," J. Pharma. Sci. 1977; 66:1.
European Pharmacopoeia 8.0, Levomethadone hydrochloride Monograph of 01/2008:1787.
Paterson et al., "Total synthesis of Aplyronine C", Org Lett 2013, 15, pp. 3118-3121.
Porter, "Resolution of chiral drugs", Pure & Appl Chem, 1991, vol. 63, No. 8, pp. 1119-1122.
Bhattacharyya, "Borohydride reductions in dichloromethane: a convenient, environmentally compatable procedure for the methylation of amines", Synth. Commun. 1995, 25, pp. 2061-2069.

(Continued)

*Primary Examiner* — Pancham Bakshi
(74) *Attorney, Agent, or Firm* — Merchant & Gould, P.C.

(57) ABSTRACT

Highly efficient methods for synthesis of levomethadone hydrochloride or dextromethadone hydrochloride are provided starting from D-alanine, or L-alanine, respectively, with retention of configuration. Methods for treating a subject are provided comprising administering a composition comprising an effective amount of levomethadone hydrochloride having not more than 10 ppm dextromethadone.

22 Claims, 28 Drawing Sheets

(56) References Cited

OTHER PUBLICATIONS

Tajbakhsh et al., "Catalyst-free one-pot reductive alkylation of primary and secondary amines and N,N-dimethylation of amino acids using sodium borohydride in 2,2,2-trifluoroethanol", Synthesis, 2011, pp. 490-496.

Weiberth et al., "Copper(I)-activated addition of Grignard reagents to nitriles. Synthesis of ketimines, ketones and amines", Journal of Organic Chemistry (1987) 52, pp. 3901-3904.

* cited by examiner

US 10,040,752 B2

SYNTHESIS OF LEVOMETHADONE HYDROCHLORIDE OR DEXTROMETHADONE HYDROCHLORIDE AND METHODS FOR USE THEREOF

BACKGROUND

Methadone hydrochloride is a long-acting opiate used for treatment of opiate dependence, opiate detoxification and for treatment of chronic, severe pain. Methadone hydrochloride currently approved for use by the FDA is a racemic mixture of levomethadone and dextromethadone, also known as DL-methadone, or (R,S)-methadone.

The active enantiomer of methadone for treatment of opiate dependence, opiate detoxification and for treatment of chronic, severe pain is levomethadone, also known as L-methadone, or R-(−)-methadone. Known methods for preparation of levomethadone may suffer from low overall yield and/or undesirable impurity profiles.

Beckett et al., J Chem Soc, 1957, 858-861, provides a chiral synthesis of levomethadone from D-Alanine in about 7 steps to produce levomethadone in about a 5-6% overall yield from D-alanine.

U.S. Publication US2014/0350302 provides a method for preparing levomethadone comprising racemic synthesis of methadone followed by resolution as a bromocamphor salt. The resolution step introduces undesirable impurities and significantly reduces the overall yield of levomethadone.

An efficient, low cost method for providing levomethadone hydrochloride in good yield, high enantiomeric excess, and with a minimal impurity profile is desirable.

On the other hand, dextromethadone, also known as D-methadone, or (S)-(+)-methadone, is known to be practically devoid of opioid activity, but maintains N-methyl-D-aspartate (NMDA) receptor antagonism. Other NMDA receptor antagonists attenuate neuronal plasticity, reverse opioid analgesic tolerance, and alleviate chronic pain states.

Moryl et al., J Opioid Management, 12:1 January/February 2016, pp. 47-55, disclose a phase I study of D-methadone in patients with chronic pain.

U.S. Publication US 2014/0088155, Manfredi et al., discloses use of D-methadone for the treatment of psychiatric symptoms.

Therefore, efficient, low cost methods are desirable for providing either dextromethadone hydrochloride or levomethadone hydrochloride in good yield, high enantiomeric excess, and with minimal impurity profiles.

SUMMARY

Highly efficient methods for synthesis of levomethadone hydrochloride or dextromethadone hydrochloride are provided starting from D-alanine, or L-alanine, respectively, with retention of configuration. Methods for treating a subject are provided comprising administering a composition comprising an effective amount of levomethadone hydrochloride having not more than 10 ppm dextromethadone.

In some embodiments, a method is provided to produce either levomethadone hydrochloride or dextromethadone hydrochloride in greater than 95%, 98%, 99%, 99.5%, or 99.9% enantiomeric excess in greater than 40% overall yield from D-alanine, or L-alanine, respectively. In one embodiment, a method is provided to produce enantiomerically pure levomethadone in greater than 40% overall yield from D-alanine.

In some embodiments, a highly efficient asymmetric synthesis of levomethadone is provided using D-alanine as the starting material. The synthesis employs low cost, readily available chemicals and produces levomethadone, or a pharmaceutically acceptable salt thereof, in greater than 40% overall yield and greater than 99% enantiomeric excess (e.e.). In some embodiments, levomethadone hydrochloride is provided in greater than 99% enantiomeric excess with not more than 100 ppm, 50 ppm, or 10 ppm of an impurity selected from the group consisting of dextromethadone, diphenylacetonitrile, levomethadone nitrile, isolevomethadone nitrile, and isolevomethadone.

In some embodiments, a process for preparing levomethadone hydrochloride is provided comprising converting D-alanine to N,N-dimethyl-D-alanine; reducing the N,N-dimethyl-D-alanine to form N,N-dimethyl-D-alaninol; combining the N,N-dimethyl-D-alaninol with an activating reagent to form an R-activated intermediate; mixing the R-activated intermediate and a base with diphenylacetonitrile to provide levomethadone nitrile; and exposing the levomethadone nitrile to ethyl magnesium bromide, and hydrochloric acid, to provide levomethadone hydrochloride.

In some embodiments, a process for preparing dextromethadone hydrochloride is provided comprising converting L-alanine to N,N-dimethyl-L-alanine; reducing the N,N-dimethyl-L-alanine to form N,N-dimethyl-L-alaninol; combining the N,N-dimethyl-L-alaninol with an activating reagent to form an S-activated intermediate; mixing the S-activated intermediate and a base with diphenylacetonitrile to provide dextromethadone nitrile; and exposing the dextromethadone nitrile to ethyl magnesium bromide, and hydrochloric acid, to provide dextromethadone hydrochloride.

In some embodiments, a process for preparing levomethadone hydrochloride is provided comprising converting D-alanine to D-alaninol; converting the D-alaninol to N,N-dimethyl-D-alaninol; combining the N,N-dimethyl-D-alaninol with an activating reagent to form an R-activated intermediate; mixing the R-activated intermediate and a base with diphenylacetonitrile to provide levomethadone nitrile; and exposing the levomethadone nitrile to ethyl magnesium bromide, and hydrochloric acid, to provide levomethadone hydrochloride.

In some embodiments, a process for preparing dextromethadone hydrochloride is provided comprising converting L-alanine to L-alaninol; converting the L-alaninol to N,N-dimethyl-L-alaninol; combining the N,N-dimethyl-L-alaninol with an activating reagent to form an S-activated intermediate; mixing the S-activated intermediate and a base with diphenylacetonitrile to provide dextromethadone nitrile; and exposing the dextromethadone nitrile to ethyl magnesium bromide, and hydrochloric acid, to provide dextromethadone hydrochloride.

In some embodiments, a process for preparing levomethadone hydrochloride is provided comprising converting D-alanine to N,N-dimethyl-D-alanine, wherein the converting comprises hydrogenating the D-alanine with formaldehyde and/or paraformaldehyde with a catalyst to form N,N-dimethyl-D-alanine.

In some embodiments, a process for preparing dextromethadone hydrochloride is provided comprising converting L-alanine to N,N-dimethyl-L-alanine, wherein the converting comprises hydrogenating the L-alanine with formaldehyde and/or paraformaldehyde with a catalyst to form N,N-dimethyl-L-alanine.

In some embodiments, a process for preparing levomethadone hydrochloride is provided comprising reducing the N,N-dimethyl-D-alanine to form N,N-dimethyl-D-alaninol, wherein the reducing comprises exposing the N,N-dimethyl-D-alanine to one or more reducing agents selected from LiAlH$_4$, BH$_3$/THF, BH$_3$/Et$_2$O, BH$_3$/BF$_3$ Et$_2$O, BH$_3$/Me$_2$S, NaBH$_4$/I$_2$, BH$_4$/cyanuric chloride, NaBH$_3$CN/ZnCl$_2$, NaBH$_4$/ZnCl$_2$, Zn(BH$_4$)$_2$, or NaBH$_4$/BF$_3$.Et$_2$O. In a specific aspect, the reducing agent is LiAlH$_4$.

In some embodiments, a process for preparing dextromethadone hydrochloride is provided comprising reducing the N,N-dimethyl-L-alanine to form N,N-dimethyl-D-alaninol, wherein the reducing comprises exposing the N,N-dimethyl-D-alanine to one or more reducing agents selected from LiAlH$_4$, BH$_3$/THF, BH$_3$/Et$_2$O, BH$_3$/BF$_3$ Et$_2$O, BH$_3$/Me$_2$S, NaBH$_4$/I$_2$, BH$_4$/cyanuric chloride, NaBH$_3$CN/ZnCl$_2$, NaBH$_4$/ZnCl$_2$, Zn(BH$_4$)$_2$, or NaBH$_4$/BF$_3$.Et$_2$O. In a specific aspect, the reducing agent is LiAlH$_4$.

In some embodiments, a process for preparing levomethadone hydrochloride is provided comprising reducing D-alanine to form D-alaninol, wherein the reducing comprises exposing the D-alanine to one or more reducing agents selected from LiAlH$_4$, BH$_3$/THF, BH$_3$/Et$_2$O, BH$_3$/BF$_3$ Et$_2$O, BH$_3$/Me$_2$S, NaBH$_4$/I$_2$, BH$_4$/cyanuric chloride, NaBH$_3$CN/ZnCl$_2$, NaBH$_4$/ZnCl$_2$, Zn(BH$_4$)$_2$, or NaBH$_4$/BF$_3$.Et$_2$O. In a specific aspect, the reducing agent is Zn(BH$_4$)$_2$.

In some embodiments, a process for preparing dextromethadone hydrochloride is provided comprising reducing L-alanine to form L-alaninol, wherein the reducing comprises exposing the L-alanine to one or more reducing agents selected from LiAlH$_4$, BH$_3$/THF, BH$_3$/Et$_2$O, BH$_3$/BF$_3$ Et$_2$O, BH$_3$/Me$_2$S, NaBH$_4$/I$_2$, BH$_4$/cyanuric chloride, NaBH$_3$CN/ZnCl$_2$, NaBH$_4$/ZnCl$_2$, Zn(BH$_4$)$_2$, or NaBH$_4$/BF$_3$.Et$_2$O. In a specific aspect, the reducing agent is Zn(BH$_4$)$_2$.

In some embodiments, a process for preparing levomethadone hydrochloride is provided comprising combining N,N-dimethyl-D-alaninol with an activating reagent to form an activated intermediate, wherein the activating reagent is selected from thionyl chloride, methanesulfonyl chloride, p-toluenesulfonyl chloride, trifluoromethanesulfonyl chloride, methanesulfonic anhydride, trifluoromethanesulfonic anhydride, or p-toluenesulfonic anhydride.

In some embodiments, a process for preparing dextromethadone hydrochloride is provided comprising combining N,N-dimethyl-L-alaninol with an activating reagent to form an activated intermediate, wherein the activating reagent is selected from thionyl chloride, methanesulfonyl chloride, p-toluenesulfonyl chloride, trifluoromethanesulfonyl chloride, methanesulfonic anhydride, trifluoromethanesulfonic anhydride, or p-toluenesulfonic anhydride.

In some embodiments, the activated intermediate is selected from (R)-1-chloro-N,N-dimethylpropan-2-amine HCl, (R)-1-chloro-N,N-dimethylpropan-2-amine, (R)-2-(dimethylamino)propyl 4-methylbenzenesulfonate, or (R)-2-(dimethylamino)propyl methanesulfonate. In a specific aspect, the activated intermediate is (R)-1-chloro-N,N-dimethylpropan-2-amine HCl. In another aspect, the activated intermediate is isolated before being used in the reacting step, or is prepared and used in the next step without isolation.

In some embodiments, a process for preparing levomethadone hydrochloride is provided comprising mixing an activated intermediate and a base with diphenylacetonitrile to provide levomethadone nitrile, wherein the mixing comprises exposing the activated intermediate to a base and diphenylacetonitrile in a solvent to form the levomethadone nitrile. In some embodiments, the base is selected from the group consisting of sodium hydroxide, potassium hydroxide, potassium t-butoxide, sodium t-butoxide, sodium methoxide, potassium methoxide, sodium ethoxide, potassium ethoxide, sodium tert-pentoxide (sodium tert-amoxide), potassium tert-pentoxide (potassium tert-amoxide), sodium isopropoxide, and potassium isopropoxide. In a specific aspect, the base is potassium t-butoxide. In some embodiments, the solvent is selected from dimethylformamide, dimethylacetamide, tetrahydrofuran, dimethyl sulfoxide, N-methyl-2-pyrrolidone, dioxane, water, or a combination thereof. In specific aspects, levomethadone nitrile is formed in >95%, >97%, >99%, >99.5%, or >99.9% enantiomeric excess (e.e.). In a specific aspect, levomethadone nitrile is formed in >99% enantiomeric excess (e.e.).

In some embodiments, a process for preparing dextromethadone hydrochloride is provided comprising mixing an activated intermediate and a base with diphenylacetonitrile to provide dextromethadone nitrile, wherein the mixing comprises exposing the activated intermediate to a base and diphenylacetonitrile in a solvent to form the dextromethadone nitrile. In some embodiments, the base is selected from the group consisting of sodium hydroxide, potassium hydroxide, potassium t-butoxide, sodium t-butoxide, sodium methoxide, potassium methoxide, sodium ethoxide, potassium ethoxide, sodium tert-pentoxide (sodium tert-amoxide), potassium tert-pentoxide (potassium tert-amoxide), sodium isopropoxide, and potassium isopropoxide. In a specific aspect, the base is potassium t-butoxide. In some embodiments, the solvent is selected from dimethylformamide, dimethylacetamide, tetrahydrofuran, dimethyl sulfoxide, N-methyl-2-pyrrolidone, dioxane, water, or a combination thereof. In specific aspects, dextromethadone nitrile is formed in >95%, >97%, >99%, >99.5%, or >99.9% enantiomeric excess (e.e.). In a specific aspect, dextromethadone nitrile is formed in >99% enantiomeric excess (e.e.).

In some embodiments, a process is provided for preparing levomethadone hydrochloride from D-alanine or dextromethadone hydrochloride from L-alanine, the process comprising: converting D-alanine to N,N-dimethyl-D-alaninol or converting L-alanine to N,N-dimethyl-L-alaninol; combining the N,N-dimethyl-D-alaninol or the N,N-dimethyl-L-alaninol with an activating reagent to form a R-activated intermediate or an S-activated intermediate, respectively; mixing the R- or S-activated intermediate and a base with diphenylacetonitrile to provide levomethadone nitrile or dextromethadone nitrile, respectively; exposing the levomethadone nitrile or dextromethadone nitrile to a Grignard reagent of formula RMgX, where R is ethyl and X=Cl, Br, or I, to form a reaction mixture; and adding hydrochloric acid to the reaction mixture to provide levomethadone hydrochloride or dextromethadone hydrochloride, respectively.

In some embodiments, a process for preparing levomethadone hydrochloride is provided comprising: converting D-alanine to N,N-dimethyl-D-alanine; reducing the N,N-dimethyl-D-alanine to form N,N-dimethyl-D-alaninol; combining the N,N-dimethyl-D-alaninol with an activating reagent to form an activated intermediate; mixing the activated intermediate and a base with diphenylacetonitrile to provide levomethadone nitrile; and exposing the levomethadone nitrile to ethyl magnesium bromide, and hydrochloric acid, to provide levomethadone hydrochloride, wherein the exposing comprises adding ethyl magnesium bromide to a stirred solution of levomethadone nitrile in an anhydrous solvent to form a reaction mixture; heating the reaction mixture to 100° C. for 1-6 hrs; cooling the reaction mixture to ambient temperature; adding hydrochloric acid to the reaction mixture with external cooling such that the reaction temperature does not exceed 50° C.; and isolating the levomethadone hydrochloride.

In some embodiments, a process is provided for preparing levomethadone hydrochloride or dextromethadone hydrochloride, the process comprising obtaining N,N-dimethyl-D-alaninol or N,N-dimethyl-L-alaninol; combining the N,N-dimethyl-D-alaninol or the N,N-dimethyl-L-alaninol with an activating reagent to form a R-activated intermediate or an S-activated intermediate, respectively; mixing the R- or S-activated intermediate and a base with diphenylacetonitrile to provide levomethadone nitrile or dextromethadone nitrile, respectively; and exposing the levomethadone nitrile or dextromethadone nitrile to a Grignard reagent of formula RMgX, where R is ethyl and X=Cl, Br, or I, to form a reaction mixture; and adding hydrochloric acid to the reaction mixture to provide levomethadone hydrochloride or dextromethadone hydrochloride, respectively.

In some embodiments, a process is provided for preparing levomethadone hydrochloride or dextromethadone hydrochloride, the process comprising obtaining N,N-dimethyl-D-alaninol or N,N-dimethyl-L-alaninol; converting the N,N-dimethyl-D-alaninol or N,N-dimethyl-L-alaninol to levomethadone nitrile or dextromethadone nitrile, respectively; and converting the levomethadone nitrile or dextromethadone nitrile to levomethadone hydrochloride or dextromethadone hydrochloride, respectively.

In some embodiments, a process is provided for preparing levomethadone hydrochloride or dextromethadone hydrochloride, the process comprising obtaining N,N-dimethyl-D-alaninol or N,N-dimethyl-L-alaninol; and converting the N,N-dimethyl-D-alaninol or N,N-dimethyl-L-alaninol to levomethadone hydrochloride or dextromethadone hydrochloride, respectively.

In some embodiments, a process is provided for preparing levomethadone hydrochloride from D-alanine or dextromethadone hydrochloride from L-alanine, the process comprising: converting D-alanine or L-alanine to levomethadone nitrile or dextromethadone nitrile, respectively; and converting the levomethadone nitrile or dextromethadone nitrile to levomethadone hydrochloride or dextromethadone hydrochloride, respectively.

In some embodiments, a process for preparing levomethadone hydrochloride is provided herein, wherein the levomethadone hydrochloride comprises not more than 0.05%(500 ppm), 0.025%(250 ppm), or 0.01%(100 ppm) of an impurity selected from dextromethadone hydrochloride, dextromethadone, isodextromethadone, isodextromethadone hydrochloride, isolevomethadone, isolevomethadone hydrochloride, levomethadone nitrile, dextromethadone nitrile, isolevomethadone nitrile, isodextromethadone nitrile, diphenylacetonitrile, 2S)-2-[[(4-methylphenyl)sulphonyl] amino]pentanedioic acid (N-tosyl-L-glutamic acid); a tartaric acid, or a bromocamphor sulfonic acid, such as a 3-bromocamphor-10-sulfonic acid.

In some embodiments, a process for preparing levomethadone hydrochloride is provided herein, wherein the levomethadone hydrochloride comprises not more than 100 ppm of an impurity selected from the group consisting of dextromethadone, diphenylacetonitrile, levomethadone nitrile, isolevomethadone nitrile, and isolevomethadone.

In some embodiments, a pharmaceutical composition is provided comprising an effective amount of levomethadone hydrochloride having not more than 100 ppm of an impurity selected from the group consisting of dextromethadone, diphenylacetonitrile, levomethadone nitrile, isolevomethadone nitrile, and isolevomethadone; and a pharmaceutically-acceptable carrier. In one aspect, a pharmaceutical composition is provided comprising an effective amount of levomethadone hydrochloride having not more than 50 ppm of dextromethadone. In another aspect, a pharmaceutical composition is provided comprising an effective amount of levomethadone hydrochloride having not more than 25 ppm of dextromethadone. In another aspect, a pharmaceutical composition is provided comprising an effective amount of levomethadone hydrochloride having not more than 10 ppm of dextromethadone.

In some embodiments, a method for management of pain, opioid detoxification, or maintenance of opioid addiction in a subject in need thereof is provided, comprising administering a pharmaceutical composition comprising an effective amount of levomethadone hydrochloride having not more than 100 ppm of an impurity selected from the group consisting of dextromethadone, diphenylacetonitrile, levomethadone nitrile, isolevomethadone nitrile, and isolevomethadone; and a pharmaceutically acceptable carrier.

In some embodiments, a method for the management of pain is provided selected from management of chronic malignant pain; management of chronic non-malignant pain; or management of pain severe enough to require daily, around-the-clock, long-term opioid treatment comprising administering a pharmaceutical composition comprising an effective amount of levomethadone hydrochloride having not more than 100 ppm of an impurity selected from the group consisting of dextromethadone, diphenylacetonitrile, levomethadone nitrile, isolevomethadone nitrile, and isolevomethadone; and a pharmaceutically acceptable carrier.

In some embodiments, a method for opioid detoxification is provided selected from detoxification treatment of opioid addiction (heroin or other morphine-like drugs); detoxification treatment of opiate addiction; and facilitation of weaning from opiate medications after extended periods in the intensive care unit (ICU), on the ward, or as an outpatient, comprising administering a pharmaceutical composition comprising an effective amount of levomethadone hydrochloride having not more than 100 ppm of an impurity selected from the group consisting of dextromethadone, diphenylacetonitrile, levomethadone nitrile, isolevomethadone nitrile, and isolevomethadone; and a pharmaceutically acceptable carrier.

In some aspects, a method for the maintenance of opioid addiction is provided that is maintenance treatment of opioid addiction (heroin or other morphine-like drugs), comprising administering a pharmaceutical composition comprising an effective amount of levomethadone hydrochloride having not more than 100 ppm of an impurity selected from the group consisting of dextromethadone, diphenylacetonitrile, levomethadone nitrile, isolevomethadone nitrile, and isolevomethadone; and a pharmaceutically acceptable carrier.

In some embodiments, a method for management of pain, opioid detoxification, or maintenance of opioid addiction in a subject in need thereof is provided, comprising administering a pharmaceutical composition comprising an effective amount of levomethadone hydrochloride having not more than 100 ppm of an impurity selected from the group consisting of dextromethadone, diphenylacetonitrile, levomethadone nitrile, isolevomethadone nitrile, and isolevomethadone; and a pharmaceutically acceptable carrier, wherein the effective amount of levomethadone hydrochloride is an amount from 0.5 mg to 500 mg, 1.0 mg to 250 mg, or 2 mg to 50 mg levomethadone hydrochloride. In some aspects, the effective amount is selected from 2.5 mg, 5 mg, 10 mg, 20 mg, 30 mg, 40 mg, 50 mg, 60 mg, 70 mg, 80 mg, 90 mg, 100 mg, 110 mg, 120 mg, 130 mg, 140 mg. 150 mg, 160 mg. 170 mg, 180 mg, 190 mg, 200 mg, 210 mg, 220 mg, 230 mg, 240 mg, or 250 mg levomethadone hydrochloride.

In some embodiments, a method for management of pain, opioid detoxification, or maintenance of opioid addiction in a subject in need thereof is provided, comprising administering a pharmaceutical composition comprising an effective amount of levomethadone hydrochloride comprising not more than 50 ppm, 25 ppm, or 10 ppm of dextromethadone or a salt thereof.

In some embodiments, a method is provided for treating a subject in need thereof, comprising administering to the subject a pharmaceutical composition comprising an effective amount of dextromethadone hydrochloride having not more than 100 ppm, not more than 50 ppm, or not more than 10 ppm of an impurity selected from the group consisting of levomethadone, diphenylacetonitrile, dextromethadone nitrile, isodextromethadone nitrile, and isodextromethadone; and a pharmaceutically acceptable carrier. In some embodiments, the subject in need thereof is suffering from a disease or condition selected from the group consisting of anxiety disorders, Alzheimer's disease, chronic pain, dementia, depression, neuropathic pain, anti-NMDA receptor encephalitis, opioid analgesic tolerance, schizophrenia, stroke, and traumatic brain injury. In some embodiments, the pharmaceutical composition comprises an effective amount of dextromethadone hydrochloride in an amount from 0.5 mg to 500 mg, 1.0 mg to 250 mg, or 2 mg to 50 mg dextromethadone hydrochloride; or the effective amount is selected from 2.5 mg, 5 mg, 10 mg, 20 mg, 30 mg, or 40 mg dextromethadone hydrochloride. In some embodiments, a dextromethadone hydrochloride composition is provided comprising not more than 50 ppm, not more than 25 ppm, or not more than 10 ppm of levomethadone or a salt thereof.

In some embodiments, an isolated compound according to Formula (I), or a pharmaceutically acceptable salt thereof, is provided

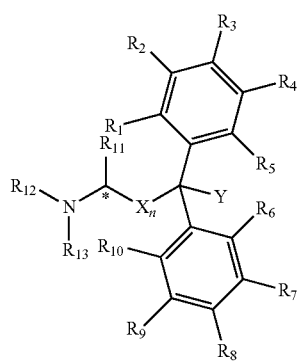

(I)

wherein $R_1$, $R_2$, $R_3$, $R_4$, $R_5$, $R_6$, $R_7$, $R_8$, $R_9$, $R_{10}$ are independently H, amino, C1-6 alkyl, alkenyl, alkynyl, halo, hydroxyl, carbocyclic, heterocyclic, or aryl;

$R_{11}$ is H, acyl, amino, amido, azido, carboxyl, alkyl, aryl, aralkyl, halo, guanidinyl, oxo, sulfanyl, sulfenyl, sulfonyl, heterocyclyl, heteroaryl, or hydroxyl;

$R_{12}$, $R_{13}$ are independently H, acyl, alkyl, alkyenyl, alkynyl, aralkyl, aryl, carboxyl, cycloalkyl, heterocyclic, or other amino (in the case of hydrazide) or $R_{12}$ and $R_{13}$ together with the nitrogen atom to which they are attached, form a ring having 4-8 atoms.

X is $(CH_2)_n$, where n=1-6;

Y is —CN or —C(O)$R_{14}$;

$R_{14}$ is alkyl, alkanyl, alkynyl, cycloalkyl, heterocyclyl, aryl, heteroaryl, alkoxy, aryloxy, aralkyl, or amino; and

*is a stereocenter selected from R or S configuration, wherein the stereocenter *is in an R configuration, and wherein the compound is present in greater than 90%, 95%, 97%, 99%, 99.5%, or 99.9% enantiomeric excess (e.e) compared to the S isomer, or wherein the stereocenter *is in an S configuration, and wherein the compound is present in greater than 90%, 95%, 97%, 99%, 99.5%, or 99.9% enantiomeric excess (e.e) compared to the R isomer.

In some embodiments, a method for preparing an isolated compound according to Formula (I), or pharmaceutically acceptable salt thereof, is provided, wherein the method comprises converting a D-amino acid to an N,N-dialkyl amino acid; treating the N,N-dialkyl amino acid with a reducing agent to form an N,N-dialkyl aminoalcohol; converting the N,N-dialkyl aminoalcohol to an activated intermediate comprising a halo group or a sulfonyl group; mixing the activated intermediate with a base and a diarylacetonitrile to provide a nitrile intermediate of formula (I), wherein Y is —CN; and exposing the nitrile intermediate to a Grignard reagent and an acid to form the compound of formula (I), wherein Y is —C(O)$R_{14}$.

In some embodiments, a method for preparing an isolated compound according to Formula (I), or pharmaceutically acceptable salt thereof, is provided, wherein Y=—C(O)$R_{14}$; $R_1$, $R_2$, $R_3$, $R_4$, $R_5$, $R_6$, $R_7$, $R_8$, $R_9$, $R_{10}$ are independently H; $R_{11}$ is —$CH_3$, —$CH(CH_3)_2$, —$CH_2CH(CH_3)_2$, —$CH(CH_3)CH_2CH_3$, -or-$CH_2Ph$; $R_{12}$ and $R_{13}$ are independently $C_{1-6}$ alkyl; $R_{14}$ is alkyl, alkenyl or aryl; n=1; and * is in the R configuration in greater than 99% e.e.

In some embodiments, a method for preparing the isolated compound of formula (I), or pharmaceutically acceptable salt thereof, is provided wherein $R_1$, $R_2$, $R_3$, $R_4$, $R_5$, $R_6$, $R_7$, $R_8$, $R_9$, $R_{10}$ are independently H; $R_{11}$ is methyl; $R_{12}$ and $R_{13}$ are independently methyl; $R_{14}$ is ethyl; n=1; and * is in the R configuration in greater than 99.5% e.e.

Figure 2A:
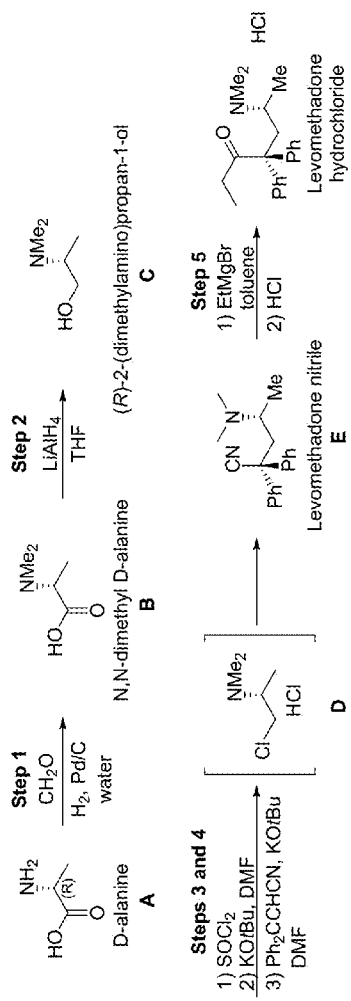
FIG. 2A shows one specific embodiment of the method for preparation of levomethadone hydrochloride in about 5 steps from D-alanine. Conversion of D-alanine to N,N- dimethyl alanine is followed by reduction with LiAlH$_4$ and subsequent conversion of the resulting amino alcohol to levomethadone HCl.
Figure 2B:
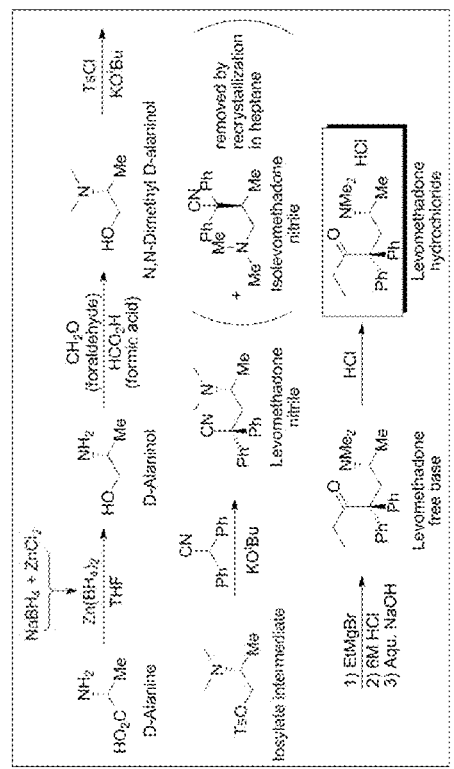

FIG. 2B shows another specific embodiment with sequential Zn(BH$_4$) reduction-CH$_2$O/HCO$_2$H dimethylation of D-alanine and subsequent conversion of the resulting amino alcohol to levomethadone HCl.

Figures 3, 4:
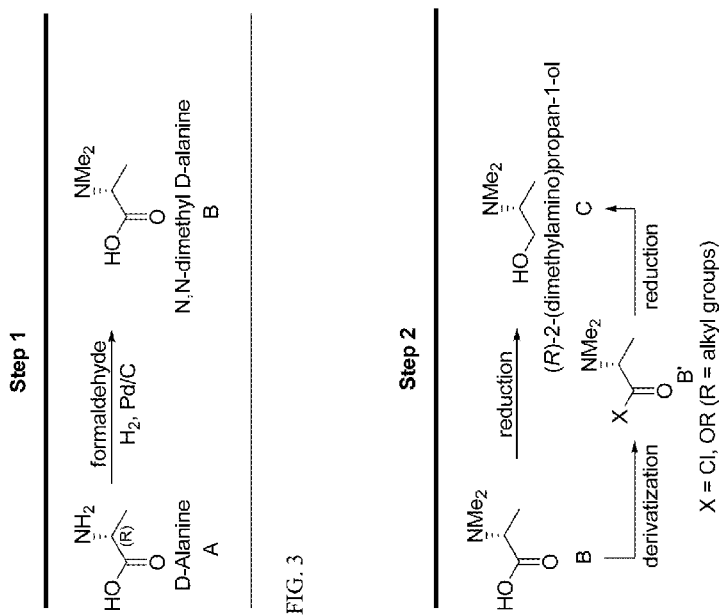

FIG. 3 shows one embodiment for formation of N,N-dimethyl D-alanine (B) by treating D-alanine starting material (A) with formaldehyde, hydrogen and palladium on carbon (Pd/C).

FIG. 4 shows one embodiment for formation of (R)-2-(dimethylamino)propan-1-ol (C) by direct reduction of N,N-dimethyl D-alanine (B) or via derivatization of B followed by reduction.

Figure 5:
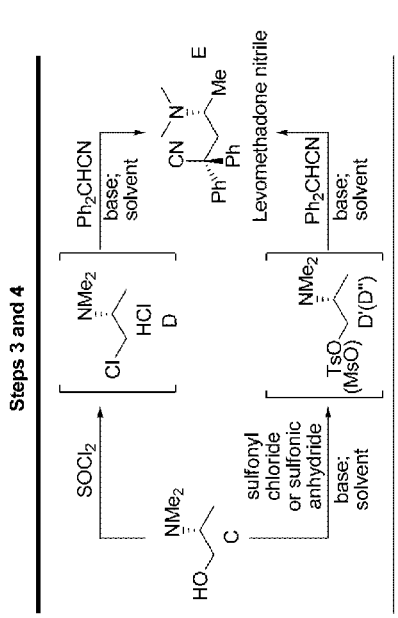

FIG. 5 shows three embodiments for activation of (R)-2-(dimethylamino)propan-1-ol (C) by thionyl chloride to form intermediate (D), (R)-1-chloro-N,N-dimethylpropan-2-amine HCl; or conversion of (C) to a sulfonate ester such as D' and D", where D' is (R)-2-(dimethylamino)propyl 4-methylbenzenesulfonate; and D" is (R)-2-(dimethylamino)propyl methanesulfonate. The activated intermediate D, D' or D" is treated with a base and diphenylacetonitrile to form levomethadone nitrile (E).

Figure 6:
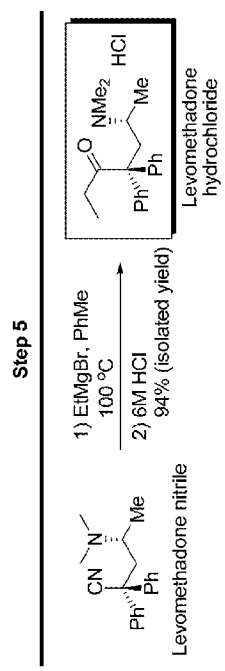

FIG. 6 shows one embodiment for the synthesis of levomethadone hydrochloride from levomethadone nitrile (E).

Figure 7:
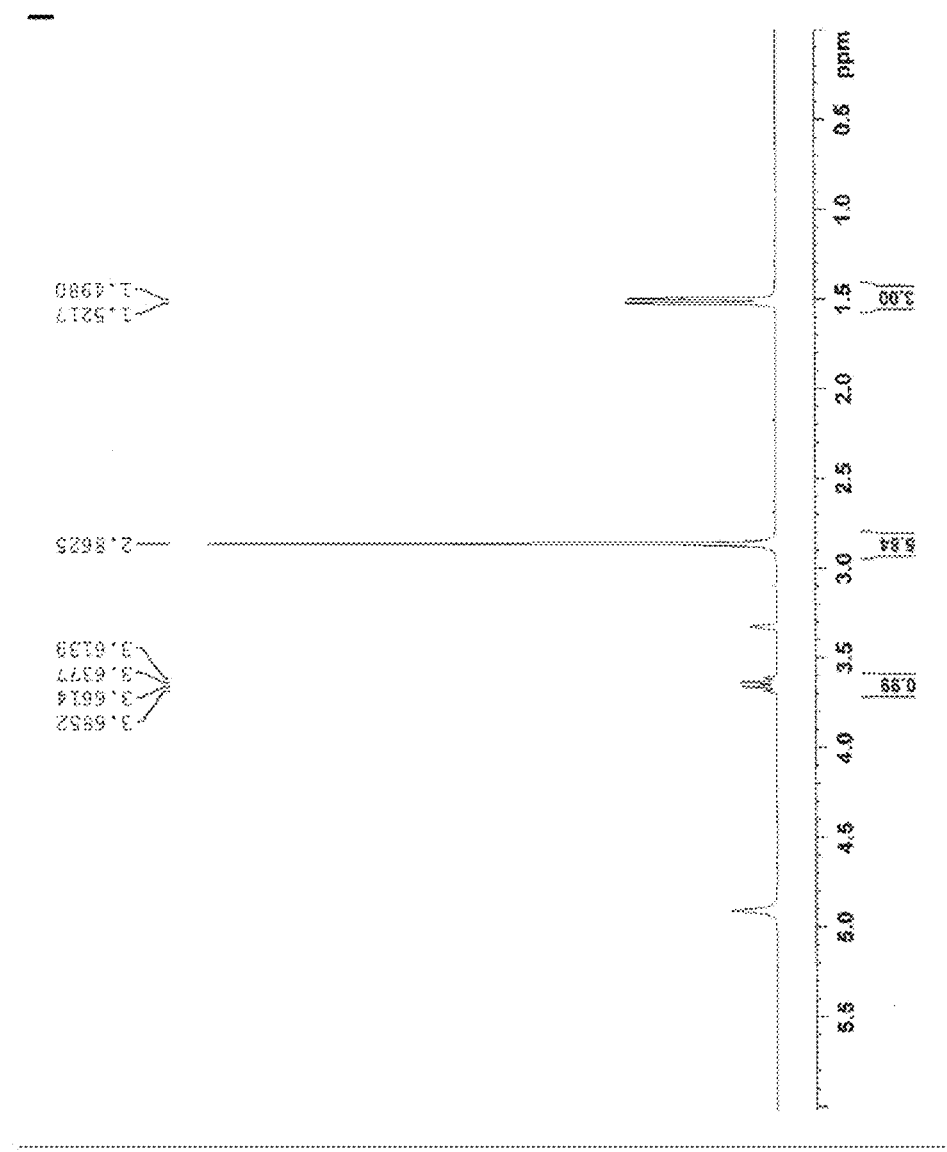

FIG. 7 shows a $^1$H-NMR spectrum of N,N-dimethyl D-alanine, intermediate B, in MeOH-d4 at 300 MHz.

Figure 8:
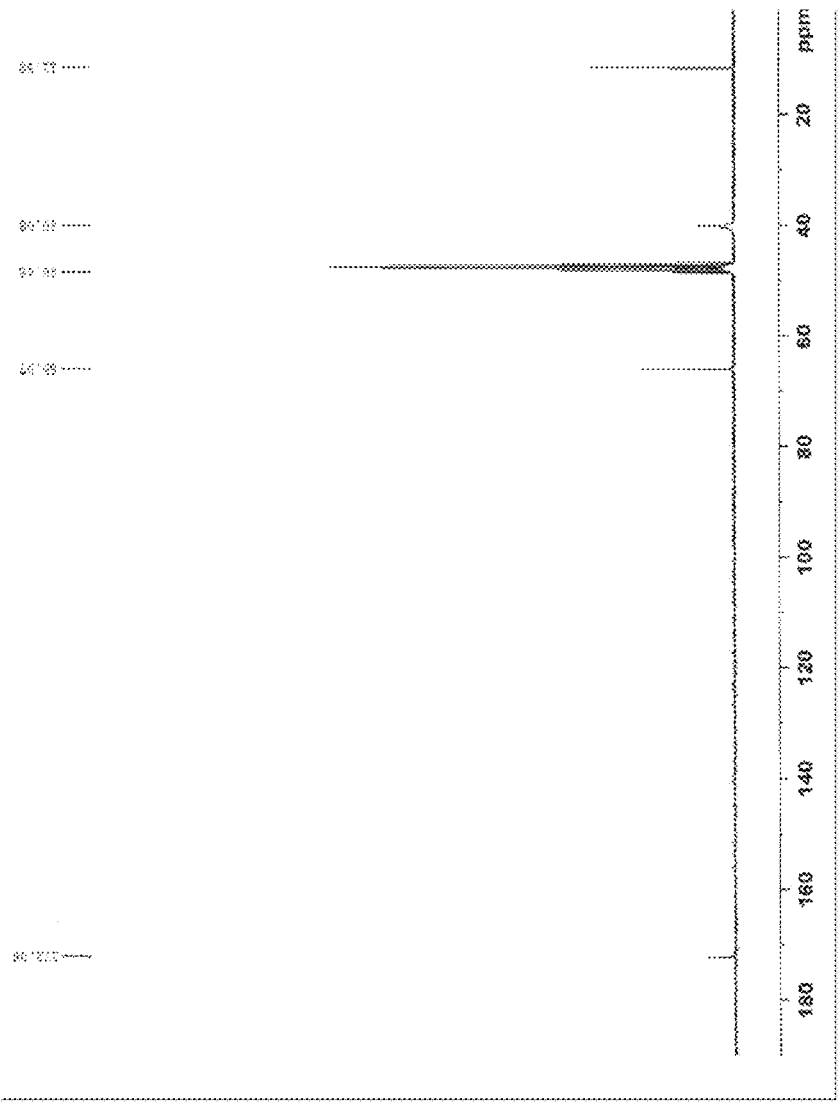

FIG. 8 shows $^{13}$C-NMR spectrum of N,N-dimethyl D-alanine, intermediate B, in MeOH-d4 at 75 MHz.

Figure 9:
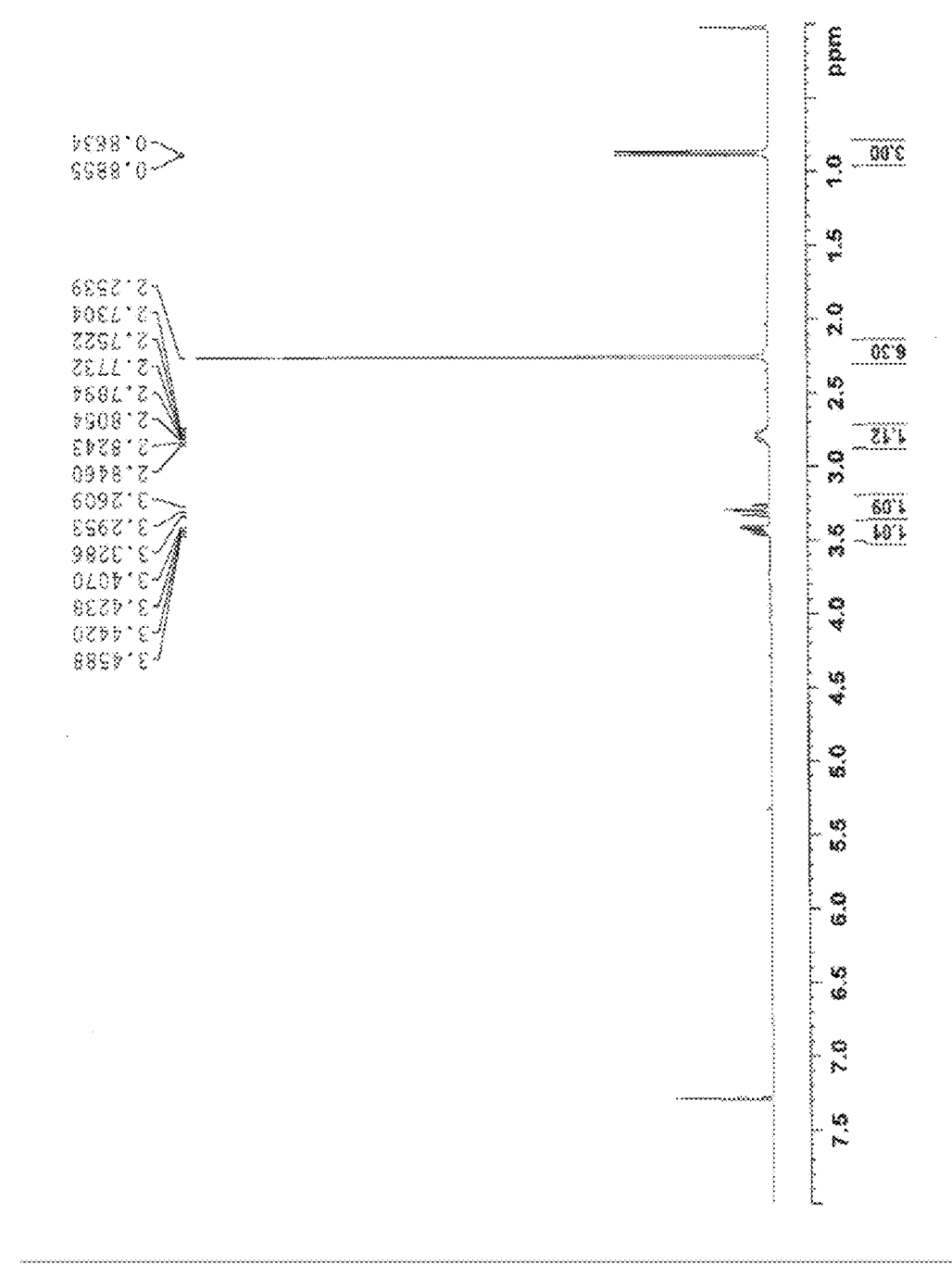

FIG. 9 shows $^1$H-NMR spectrum of crude (R)-2-(N,N-dimethylamino)propan-1-ol (N,N-dimethyl D-alaninol) in CDCl$_3$ at 300 MHz.

Figure 10:
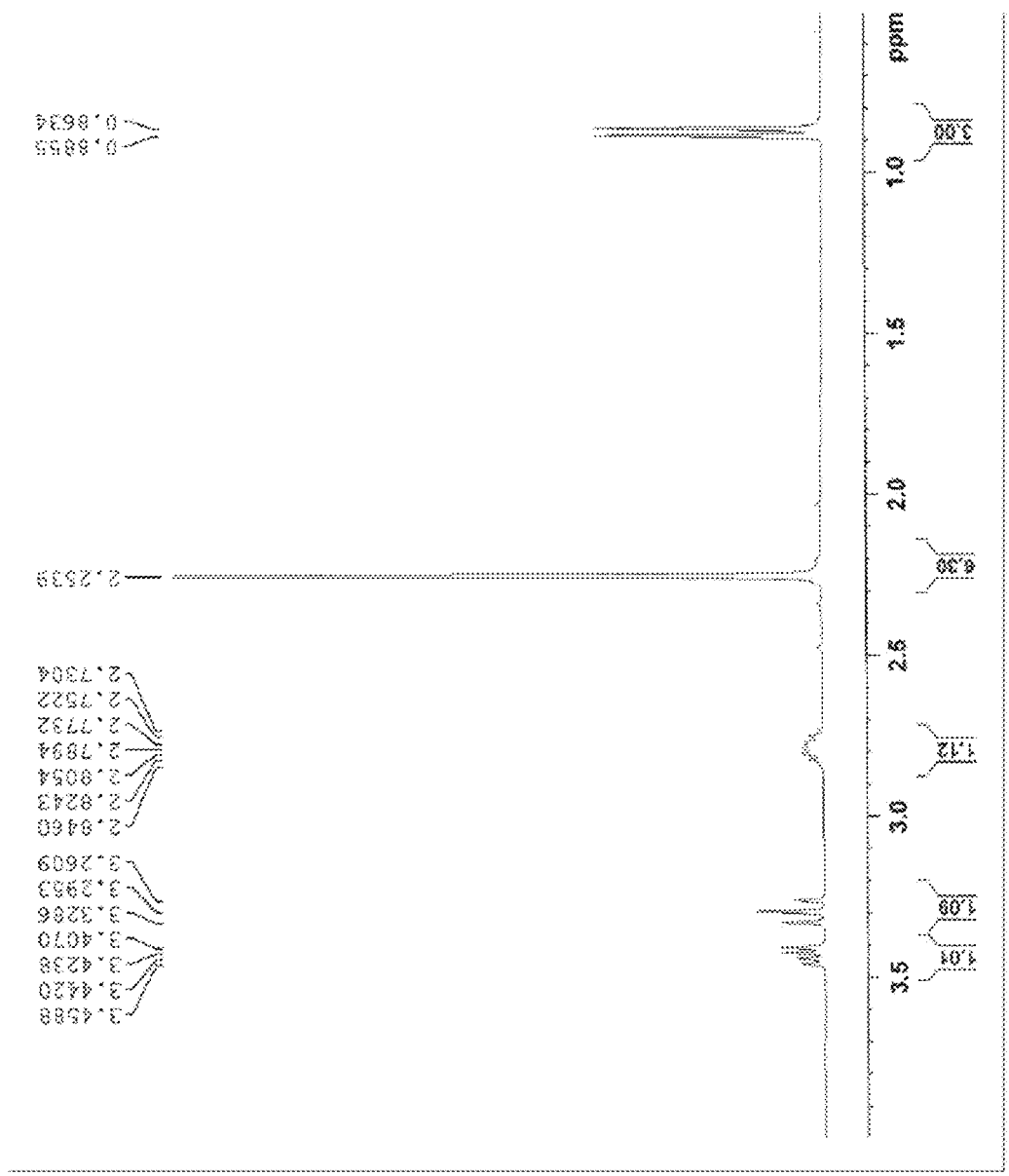

FIG. 10 shows a magnified portion of FIG. 9, $^1$H-NMR spectrum of crude N,N-dimethyl D-alaninol, intermediate C, in CDCl$_3$ at 300 MHz from about δ 0.1-4.0 ppm.

Figure 11:
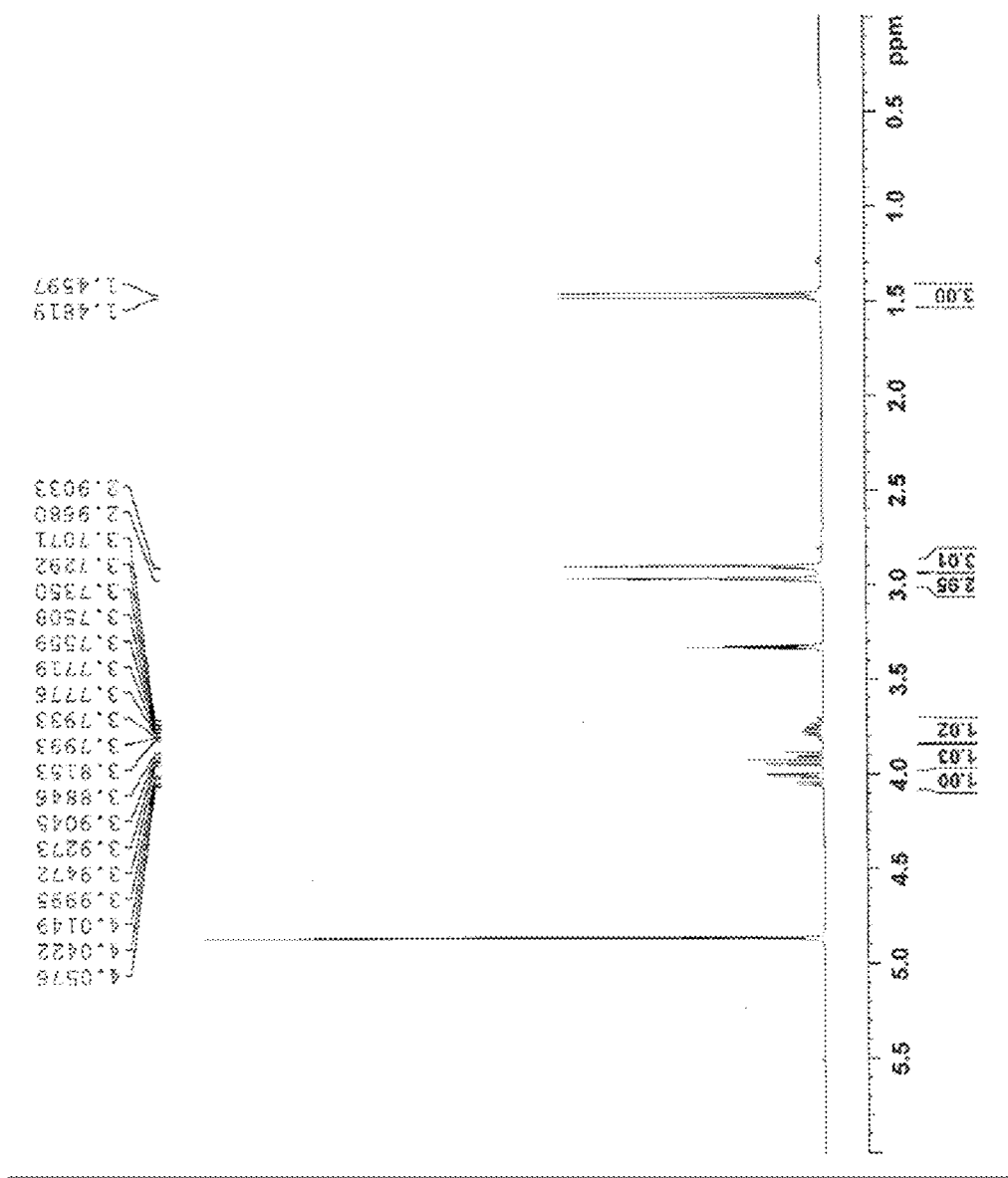

FIG. 11 shows a $^1$H-NMR spectrum of crude intermediate D, (R)-1-chloro-N,N-dimethylpropan-2-amine HCl, in MeOH-d4 at 300 MHz.

Figure 12:
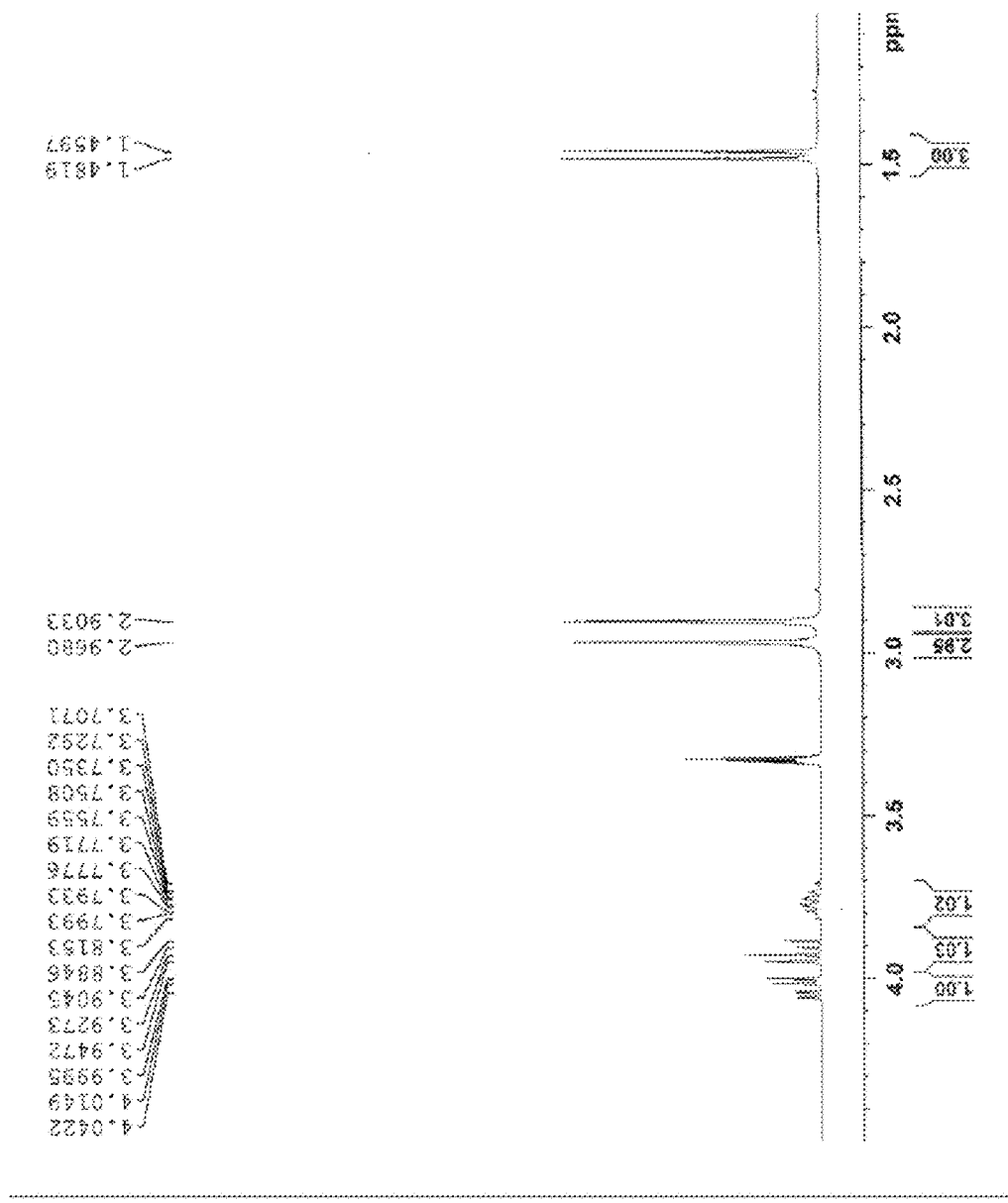

FIG. 12 shows a magnified portion of FIG. 11, $^1$H-NMR spectrum of crude intermediate D, (R)-1-chloro-N,N-dimethylpropan-2-amine HCl, in MeOH-d4 at 300 MHz from about δ 1-5 ppm.

Figure 13:
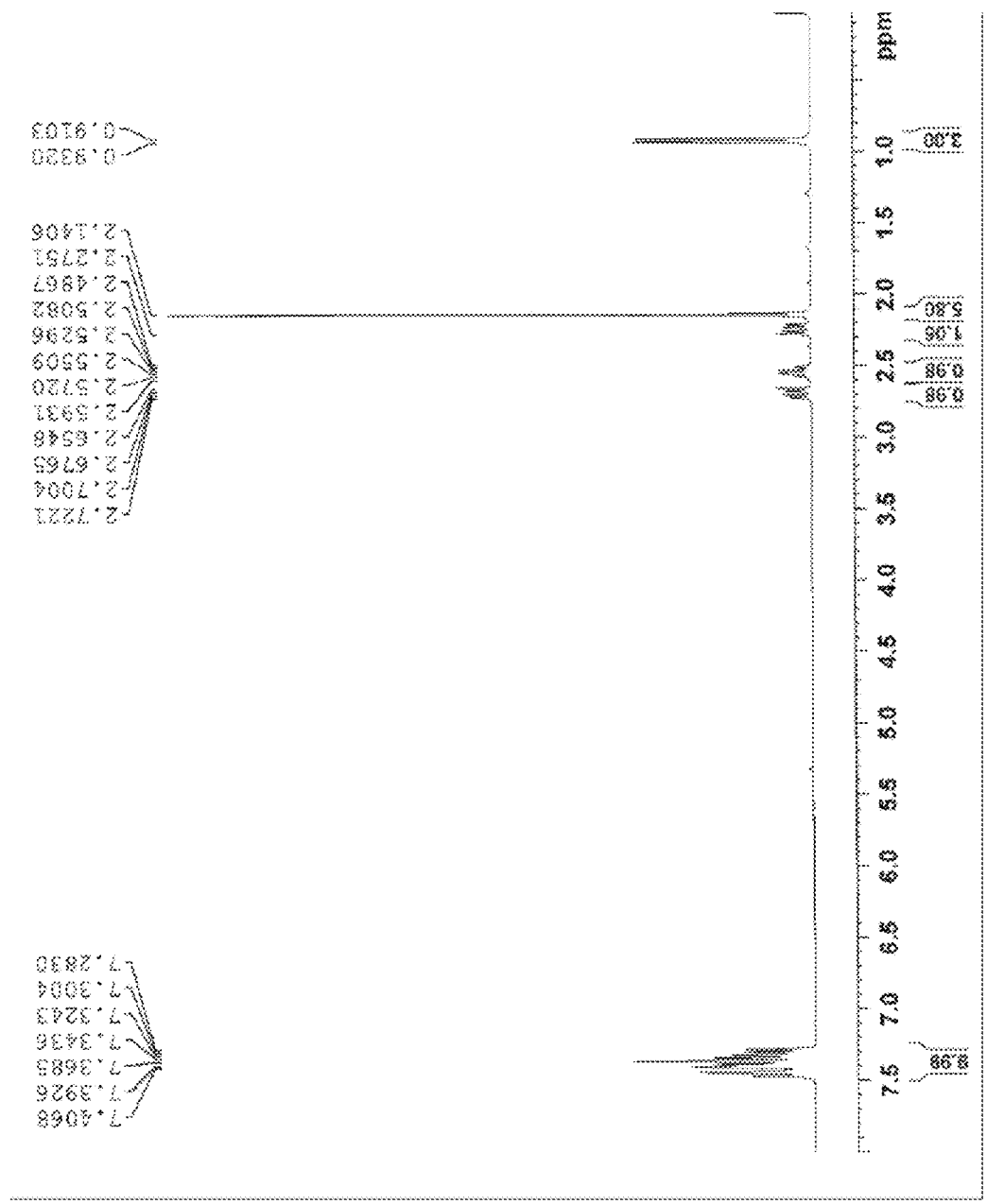

FIG. 13 shows $^1$H-NMR spectrum of levomethadone nitrile, intermediate E.

Figure 14:
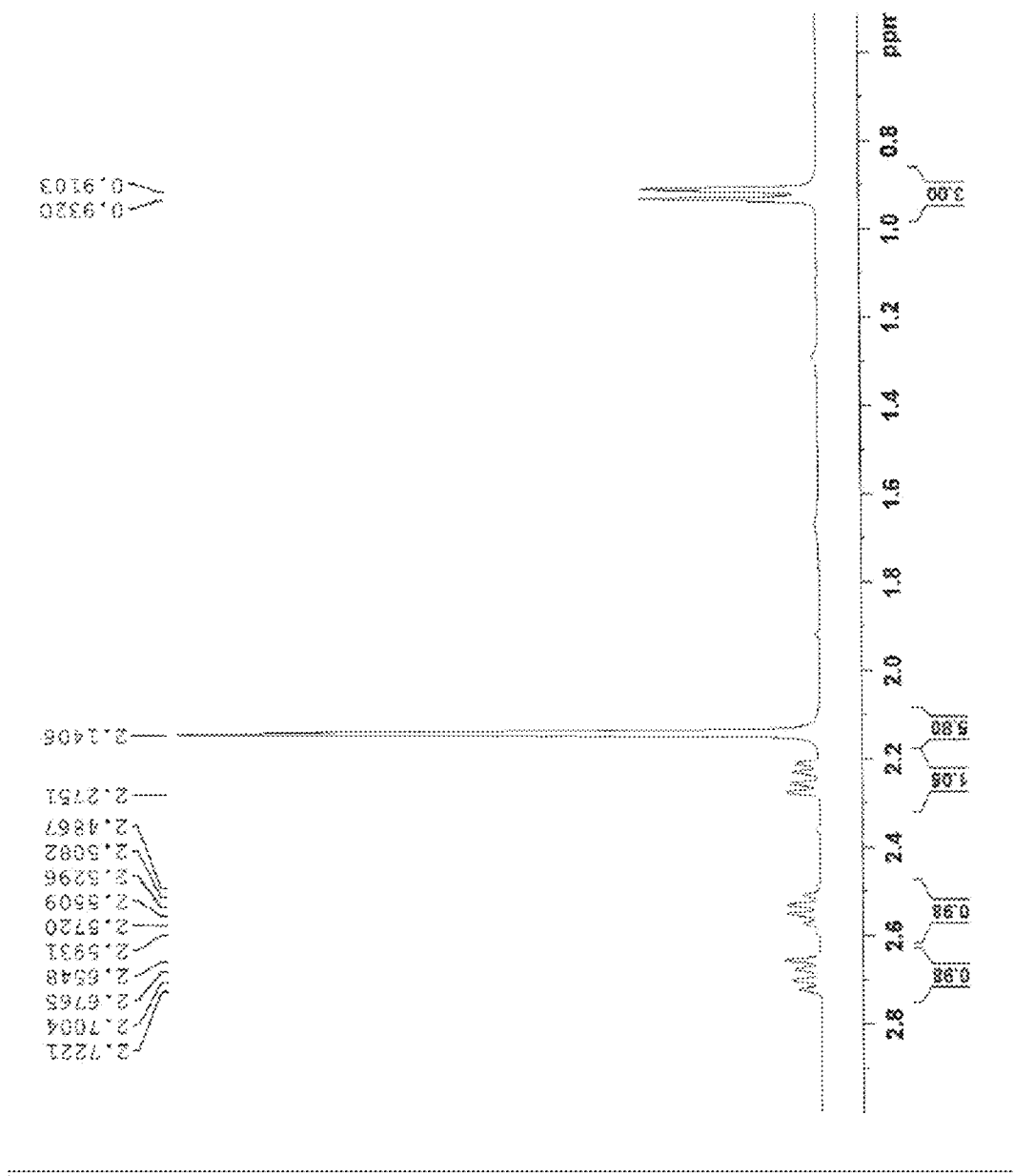

FIG. 14 shows a magnified portion of FIG. 13, $^1$H-NMR spectrum of levomethadone nitrile, intermediate E, from about 0.6 to 3 ppm.

Figure 15:
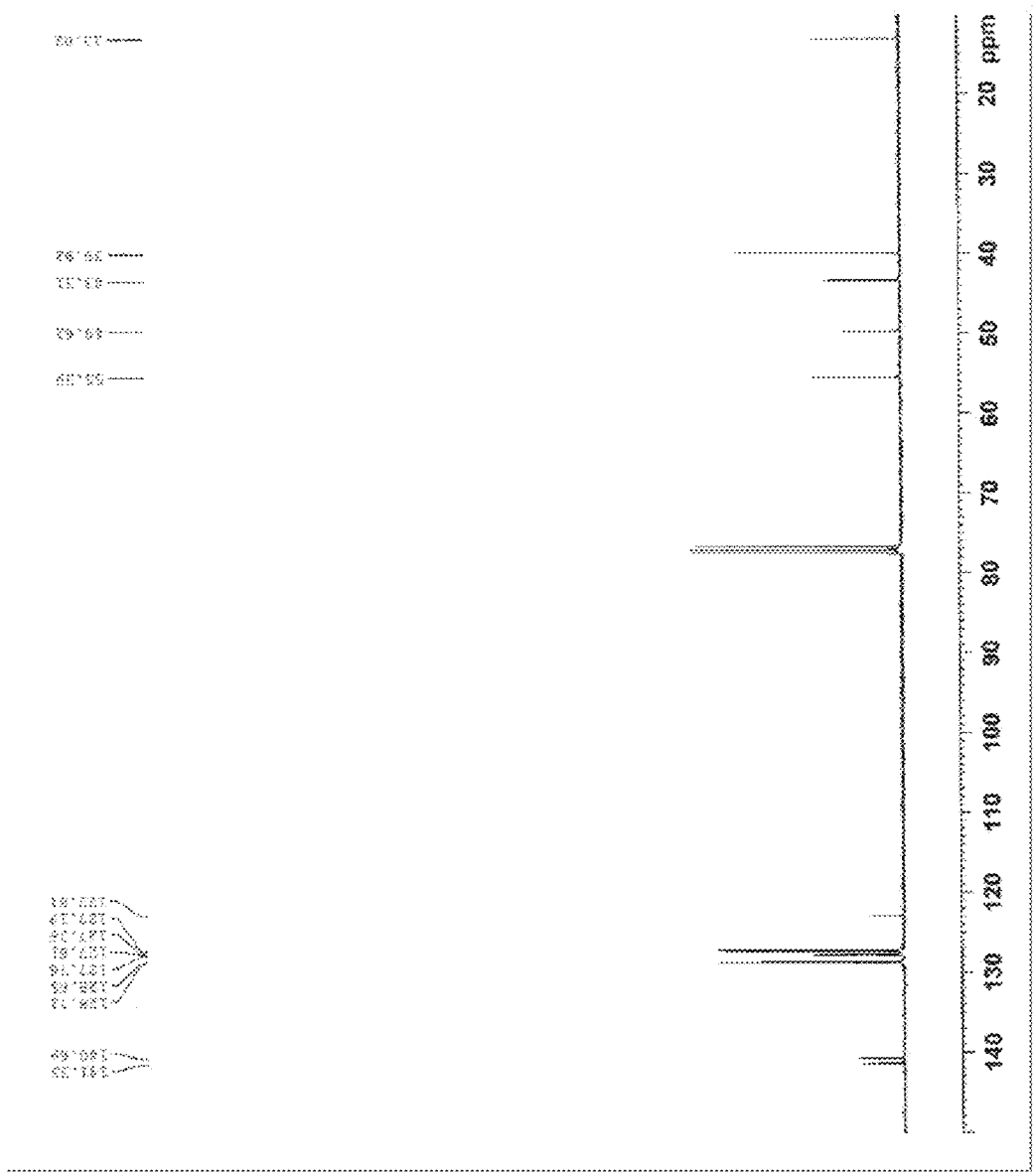

FIG. 15 shows a $^{13}$C-NMR spectrum of levomethadone nitrile, intermediate E, showing the presence of 14 magnetically different C atoms.

Figure 16:
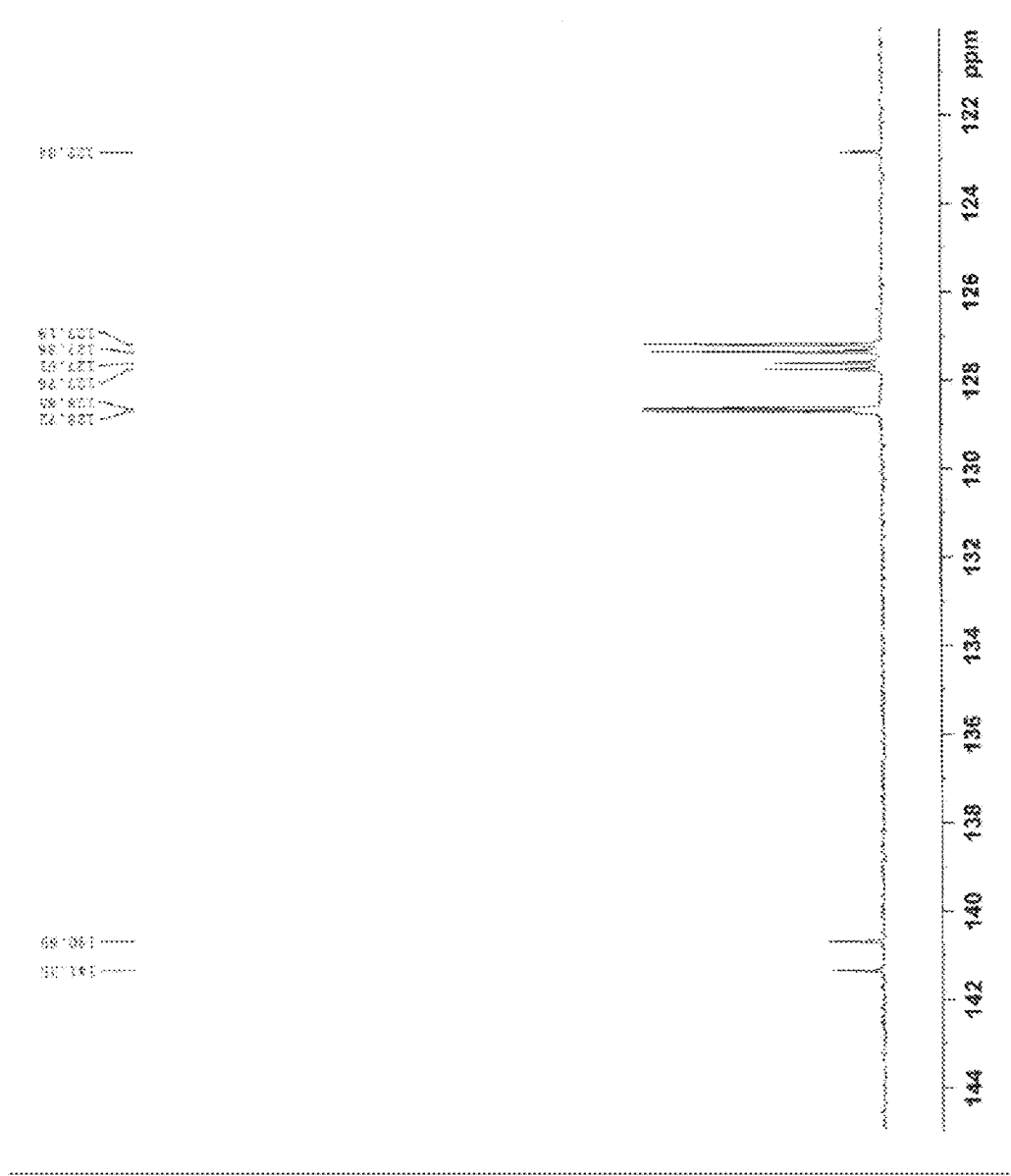

FIG. 16 shows a magnified portion of FIG. 15 $^{13}$C-NMR spectrum of levomethadone nitrile, intermediate E, from about 120-145 ppm.

Figure 17:
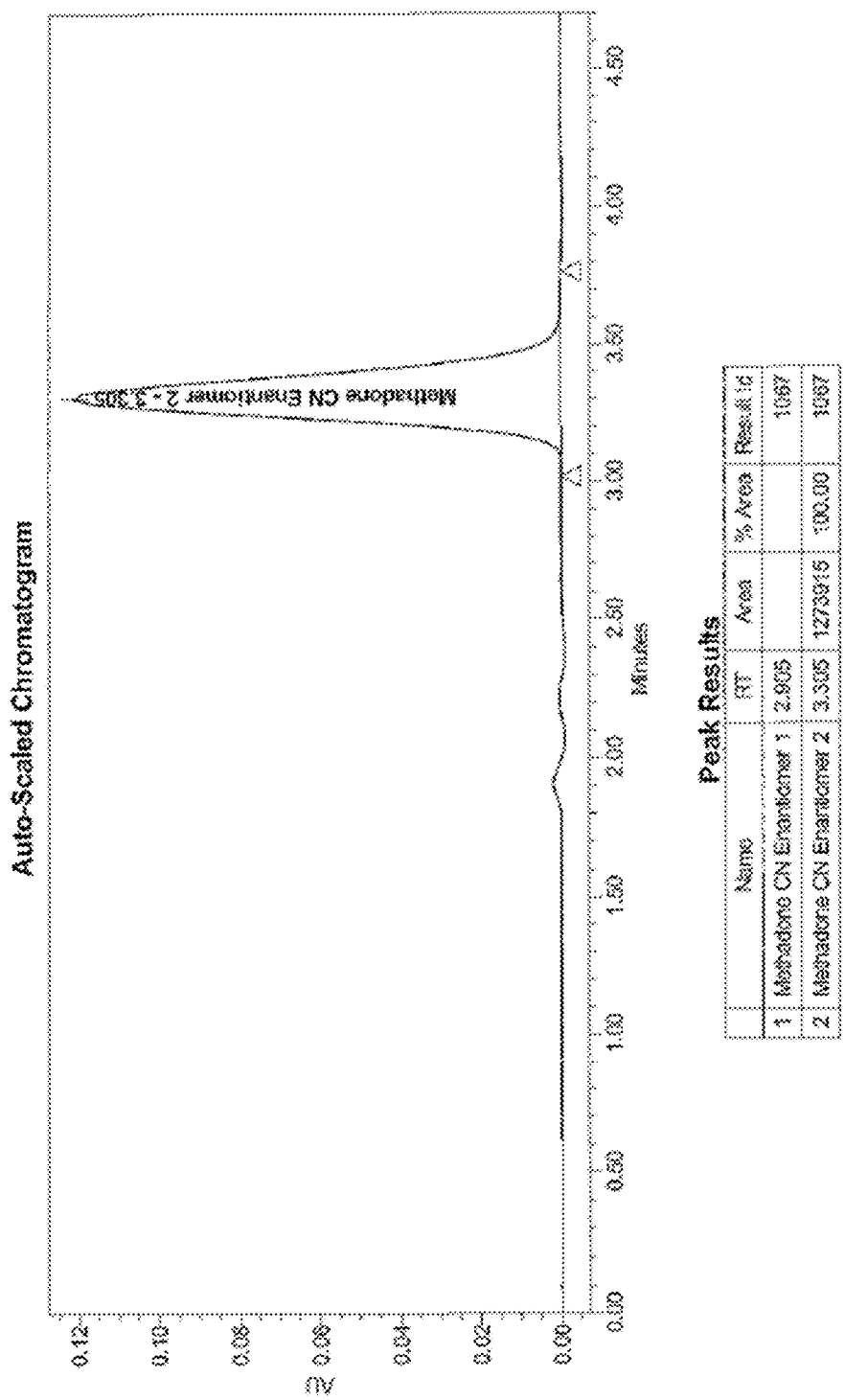

FIG. 17 shows chiral HPLC chromatogram for levomethadone nitrile, intermediate E, of example 3. A single enantiomer with e.e. >99% is shown.

Figure 18:
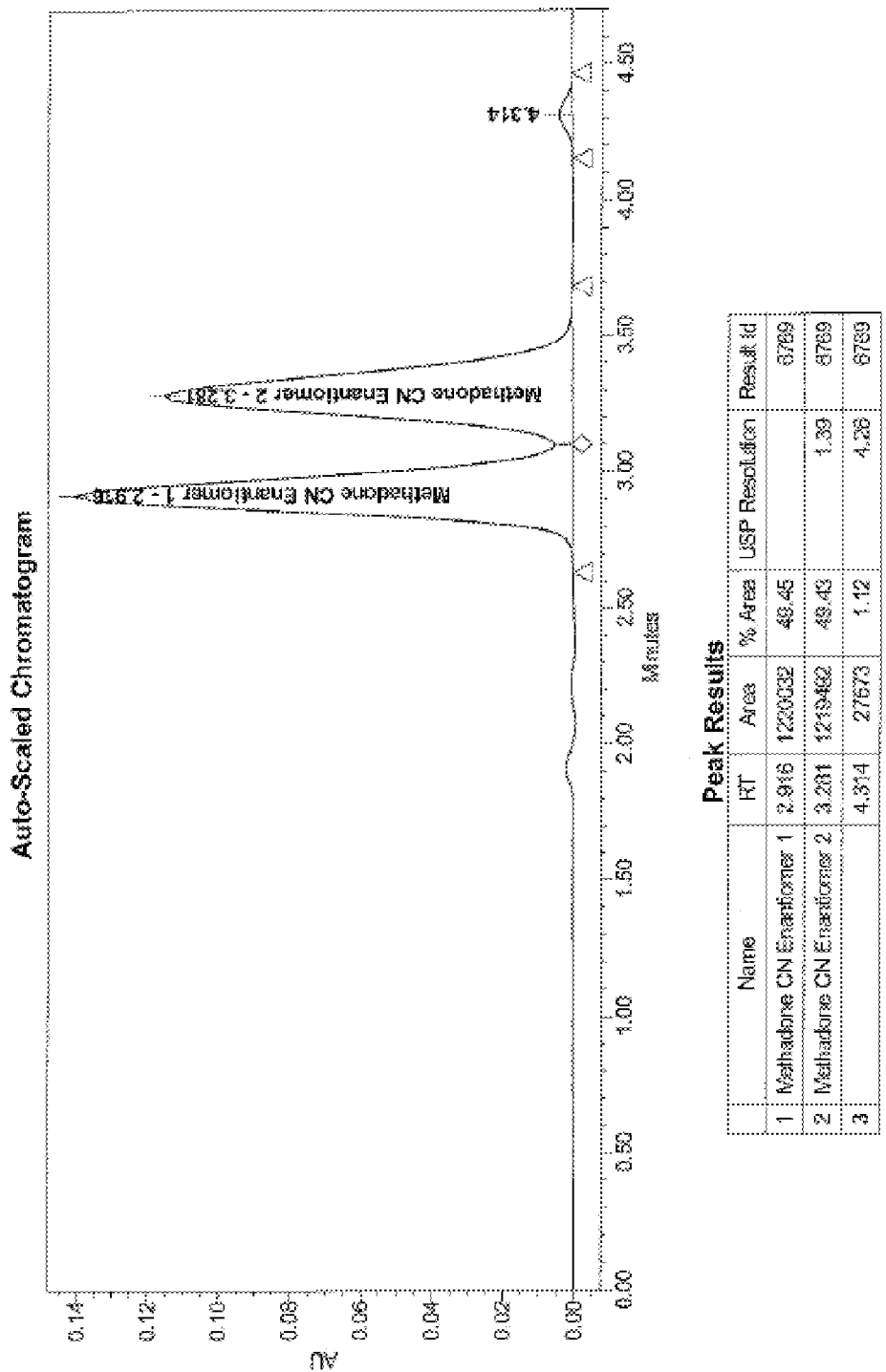

FIG. 18 shows chiral HPLC chromatogram for comparative racemic methadone nitrile. Two enantiomers are seen in about a 1:1 ratio.

Figure 19A:
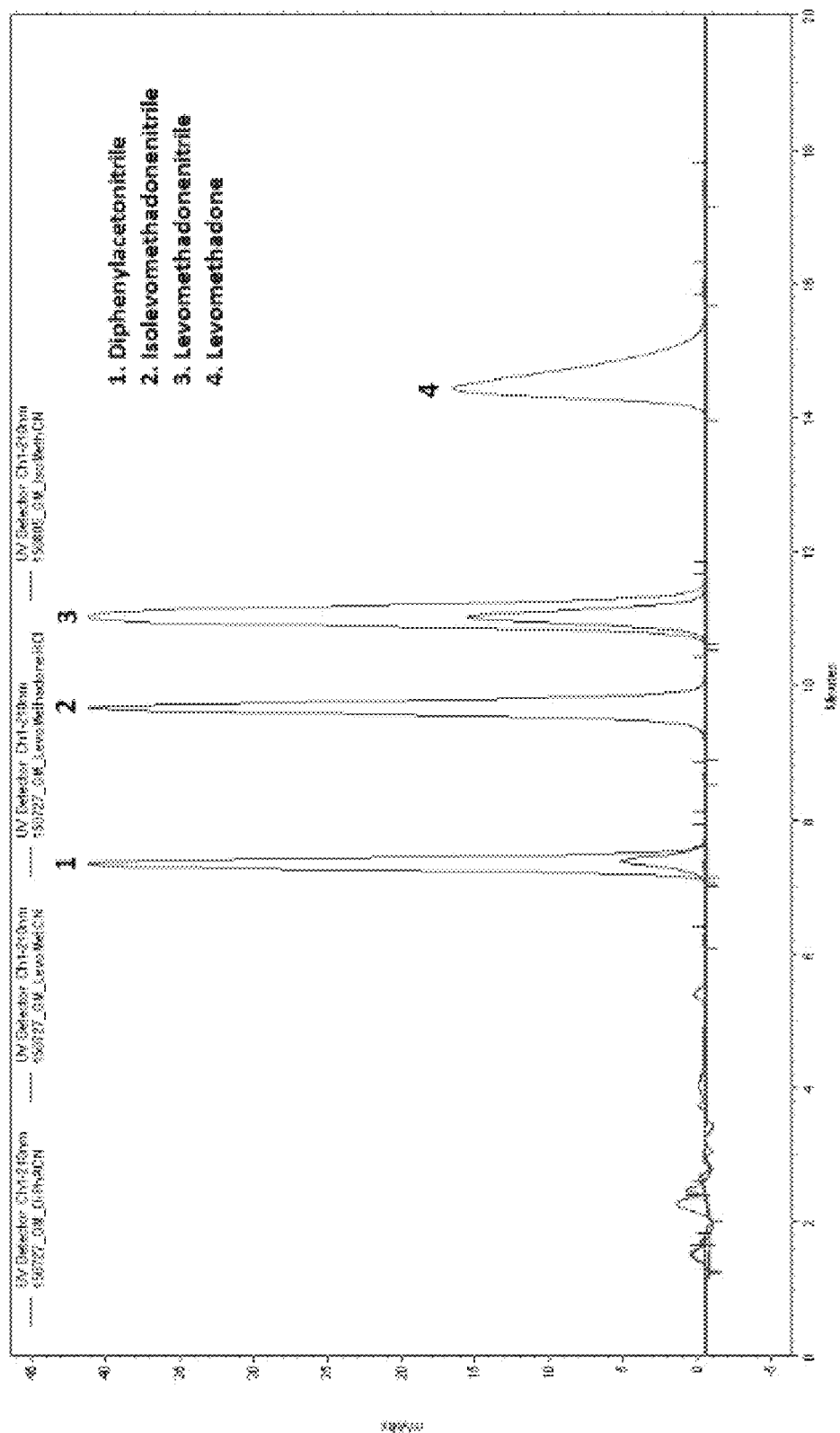

FIG. 19A shows C18 reverse phase HPLC separation of a mixture of (1) diphenylacetonitrile, (2) isolevomethadone nitrile, (3) levomethadone nitrile, and (4) methadone.

Figure 19B:
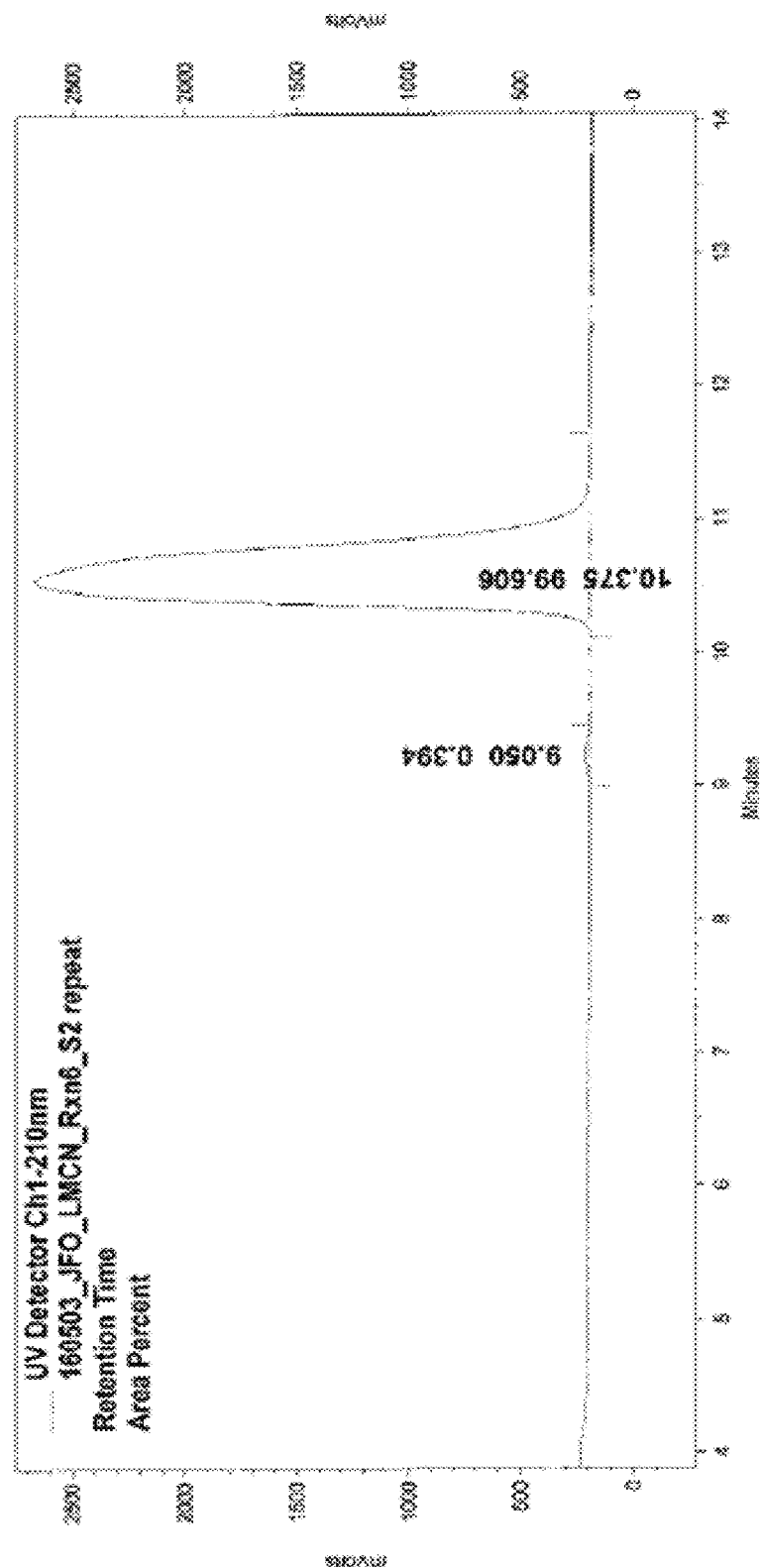

FIG. 19B shows C18 reverse phase HPLC analysis of levomethadone nitrile after first recrystallization with heptane exhibiting 99.6% purity at 210 nm.

Figure 19C:
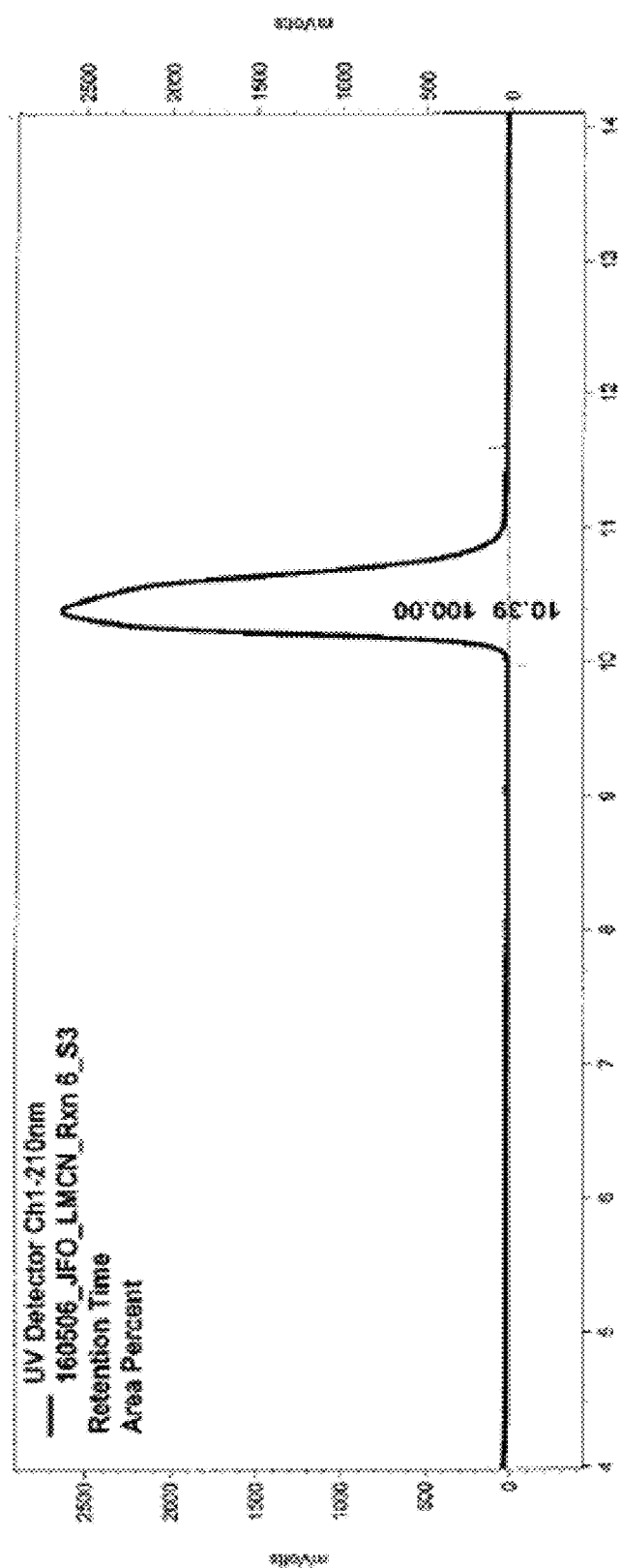

FIG. 19C shows C18 reverse phase HPLC analysis of levomethadone nitrile after second recrystallization with heptane exhibiting 100% purity at 210 nm.

Figure 20:
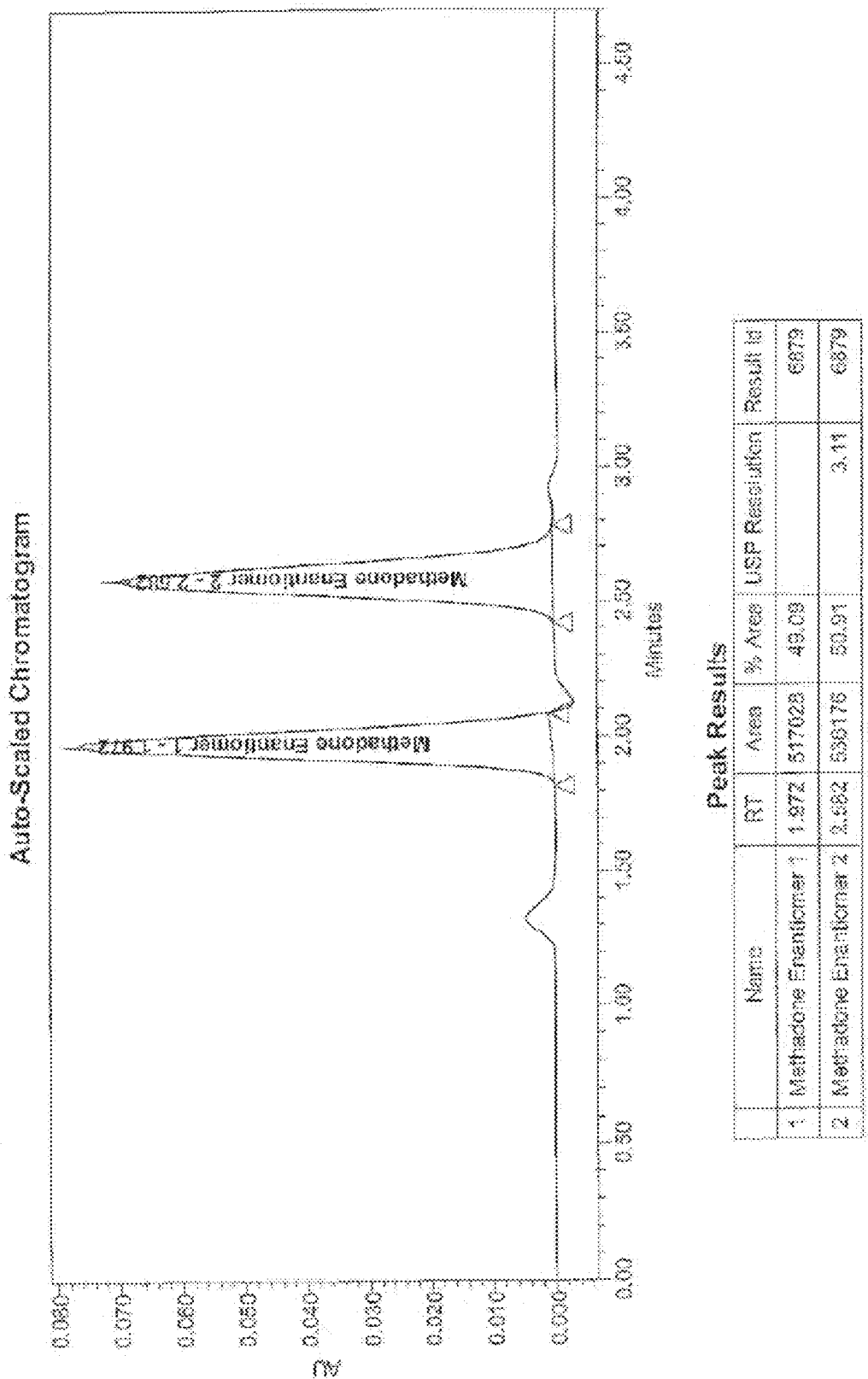

FIG. 20 shows chiral HPLC chromatogram for comparative racemic methadone. Two enantiomers are seen in about a 1:1 ratio.

Figure 21:
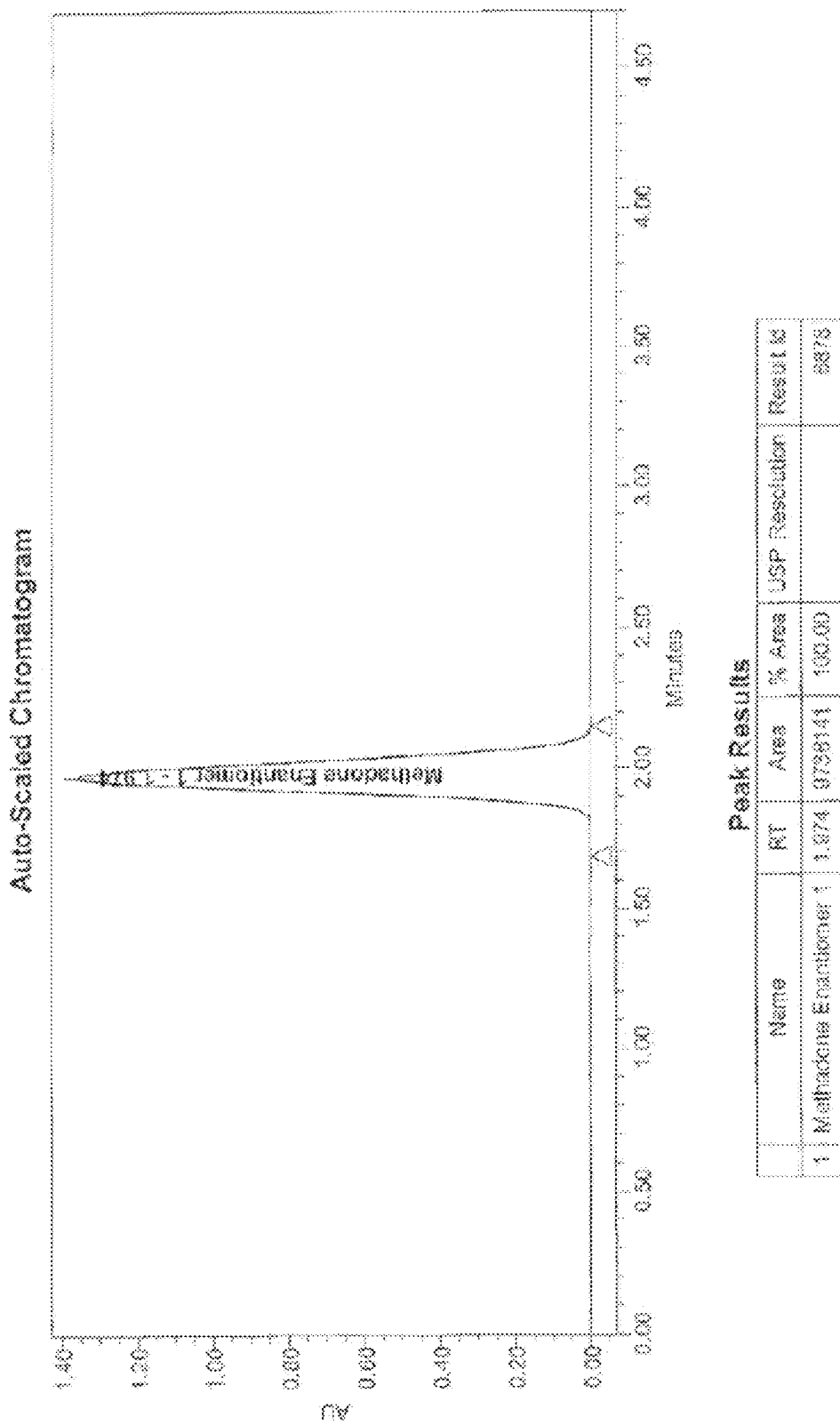

FIG. 21 shows chiral HPLC chromatogram for levomethadone prepared according to the disclosure. A single enantiomer with e.e. >99% is shown.

Figure 22:
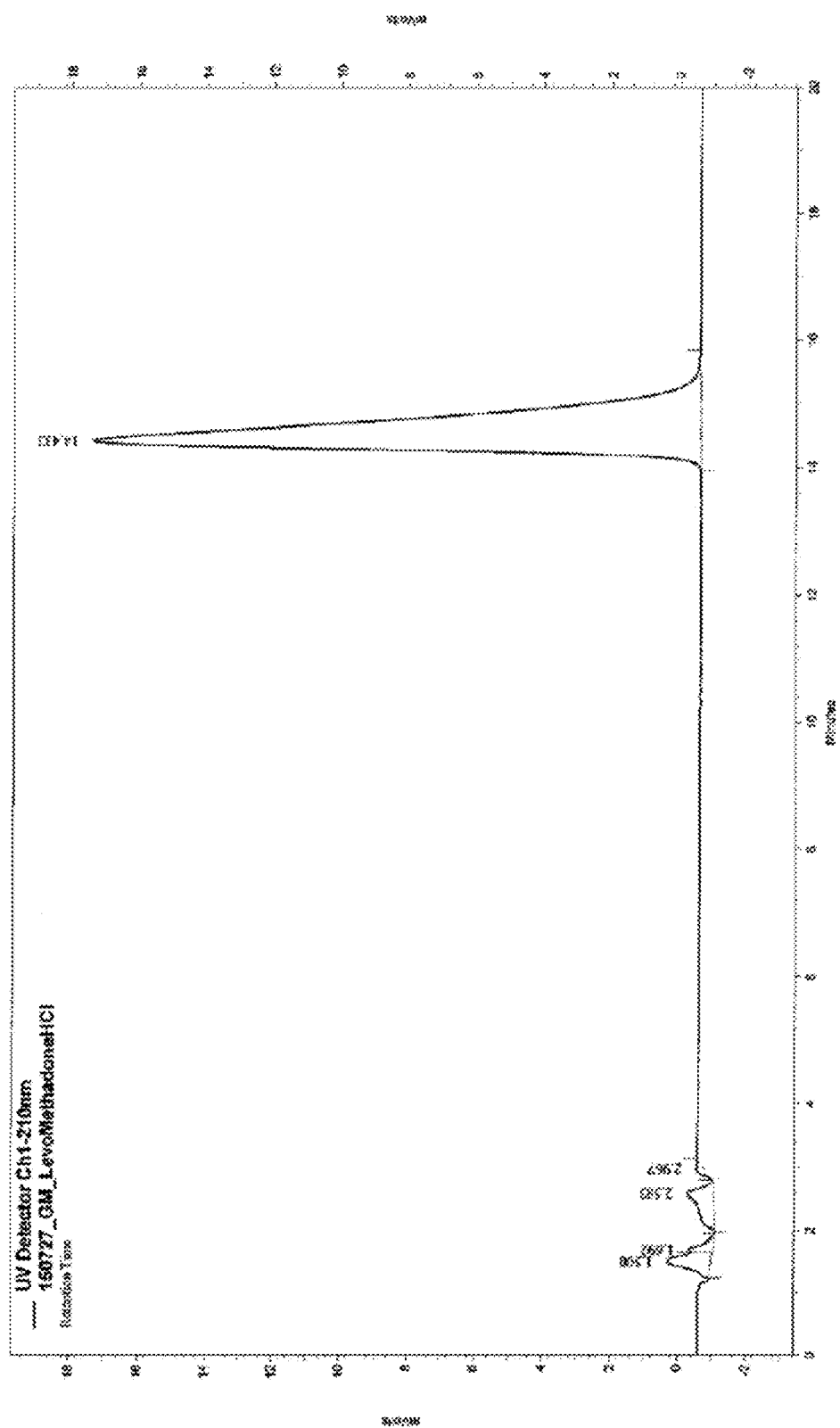

FIG. 22 shows a representative C18 reverse phase HPLC chromatogram of levomethadone hydrochloride. Less than 100 ppm of diphenylacetonitrile, isolevomethadone nitrile, and levomethadone nitrile impurities are detected at 210 nm.

Figure 23:
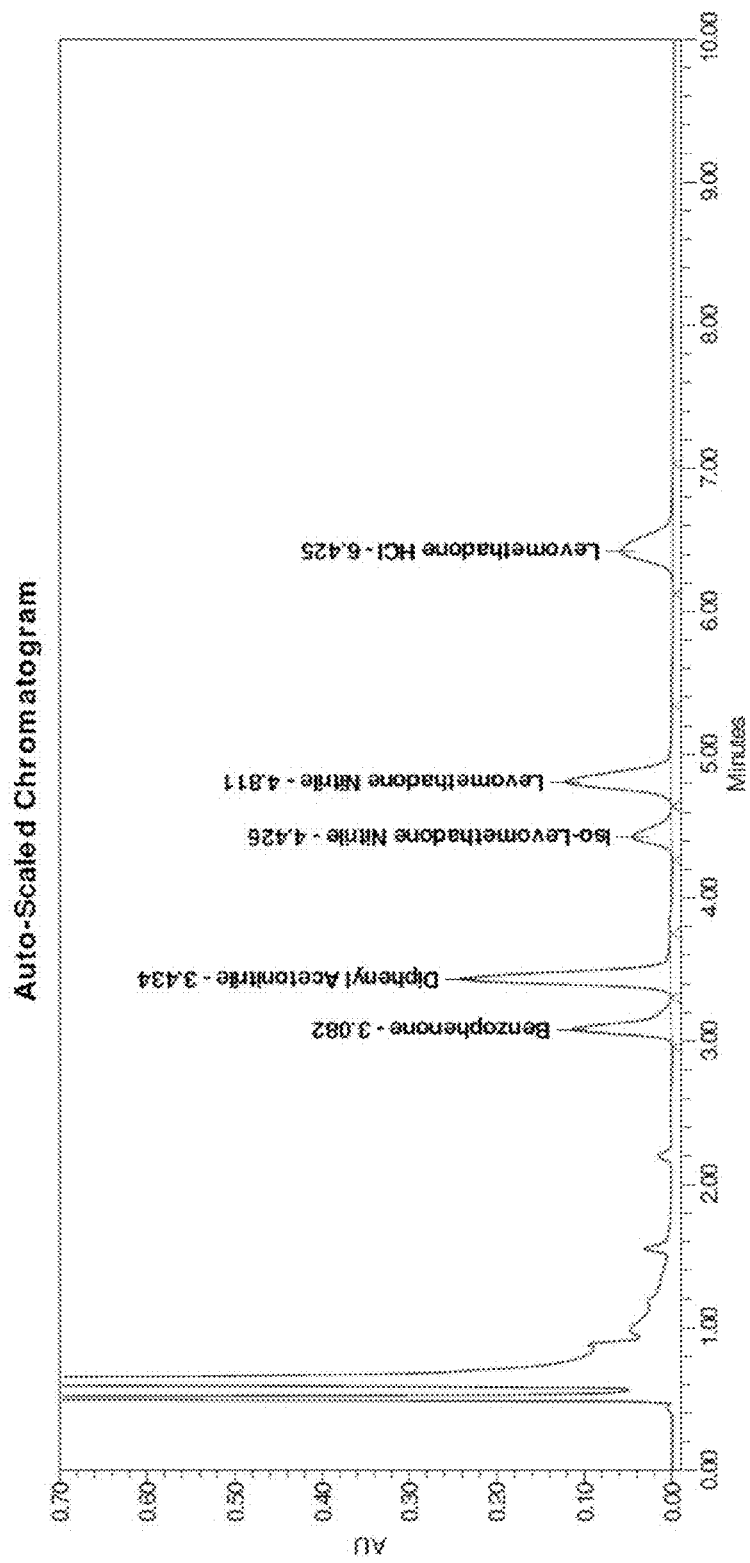

FIG. 23 shows a representative C18 reverse phase UPLC chromatogram with baseline resolution of a mixture of (1) benzophenone, (2) starting material reagent diphenylacetonitrile, (3) impurity isolevomethadone nitrile, (4) intermediate levomethadone nitrile, and (5) product Levomethadone, run according to method of Example 4C.

Figure 24:
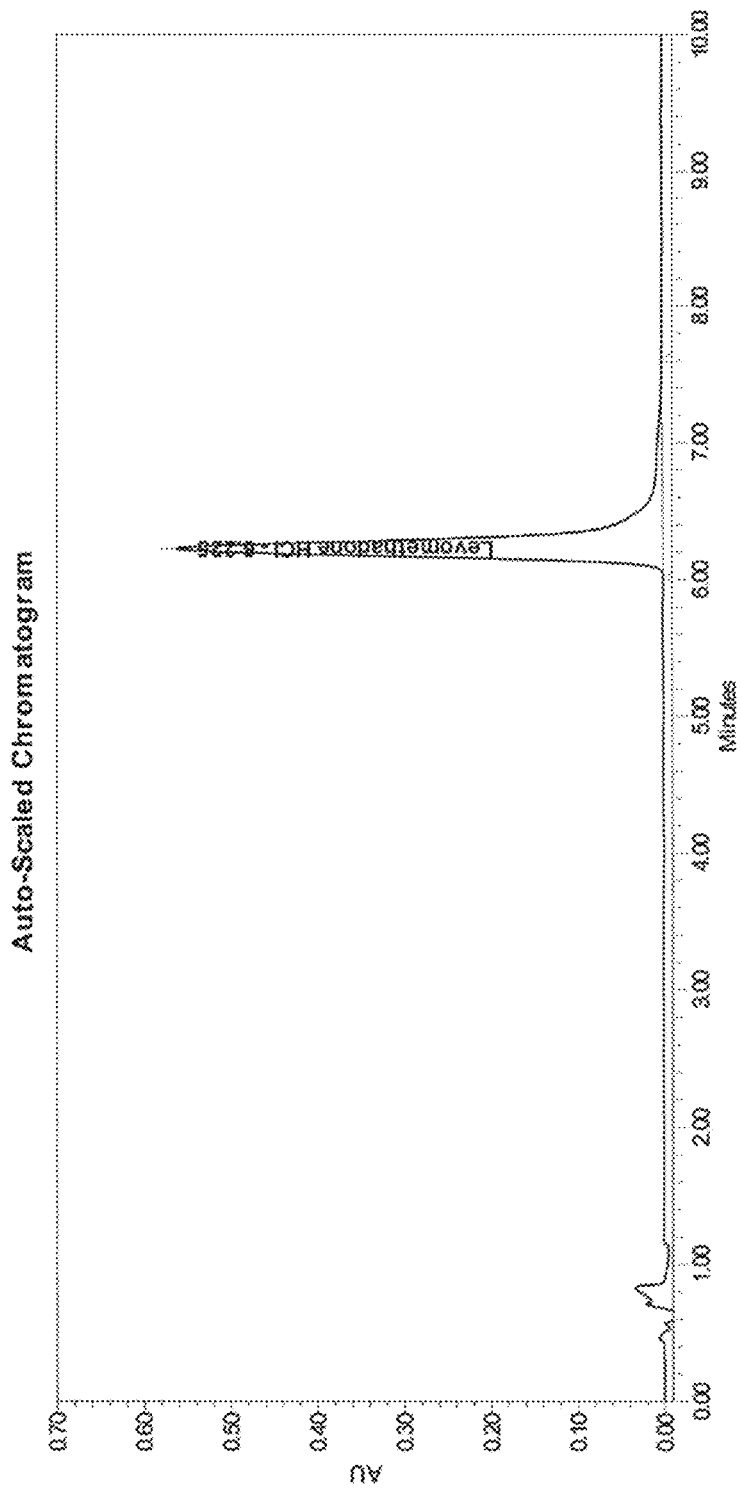

FIG. 24 shows a representative C18 reverse phase UPLC chromatogram of levomethadone hydrochloride prepared according to the disclosure. Less than 100 ppm of diphenylacetonitrile, isolevomethadone nitrile, and levomethadone nitrile impurities are detected at 210 nm.

Figure 25A:
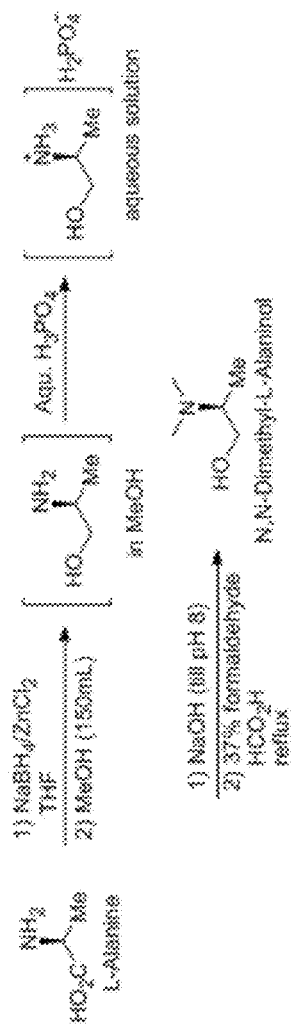

FIG. 25A shows one route for the synthesis of N,N-dimethyl-L-alaninol from L-alanine.

Figure 25B:
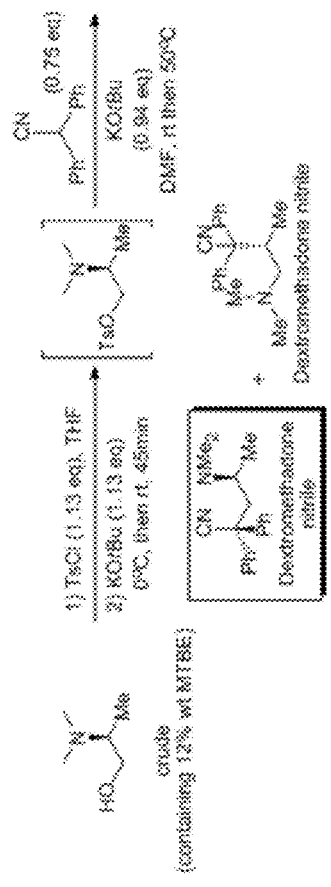

FIG. 25B shows one route for the synthesis of dextromethadone nitrile from N,N-dimethyl-L-alaninol.

Figure 25C:
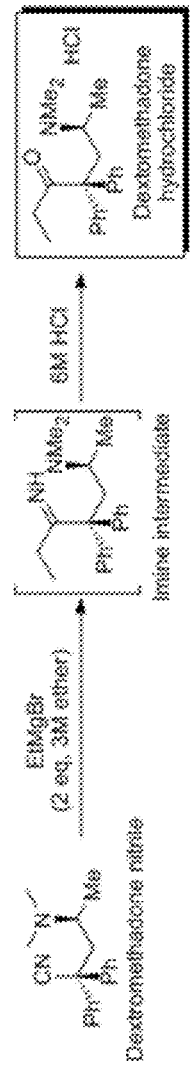

FIG. 25C shows one route for the synthesis of dextromethadone hydrochloride from dextromethadone nitrile.

Figure 26A:
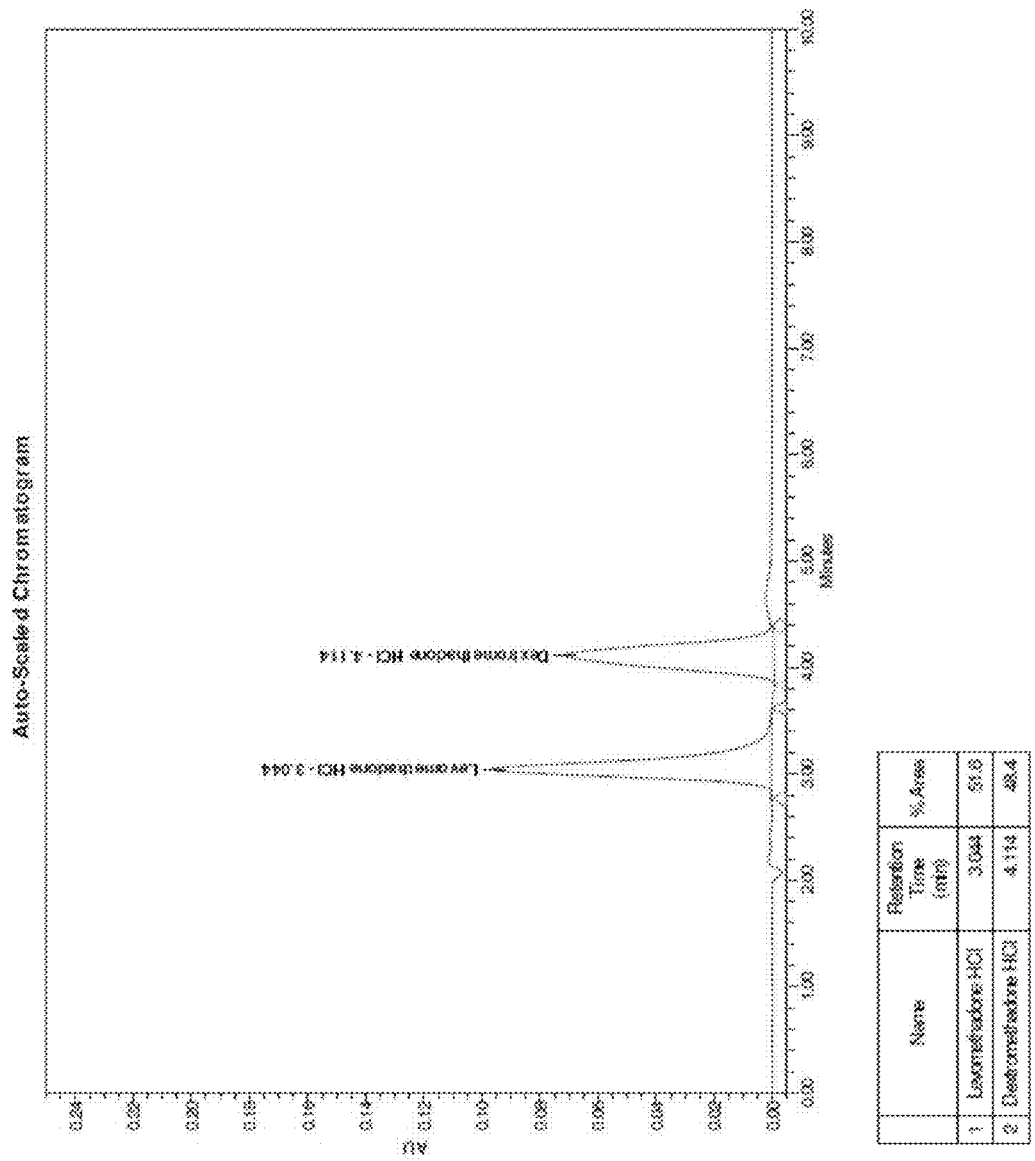

FIG. 26A shows a reference chiral chromatogram of a mixture of levomethadone hydrochloride and dextromethadone hydrochloride.

Figure 26B:
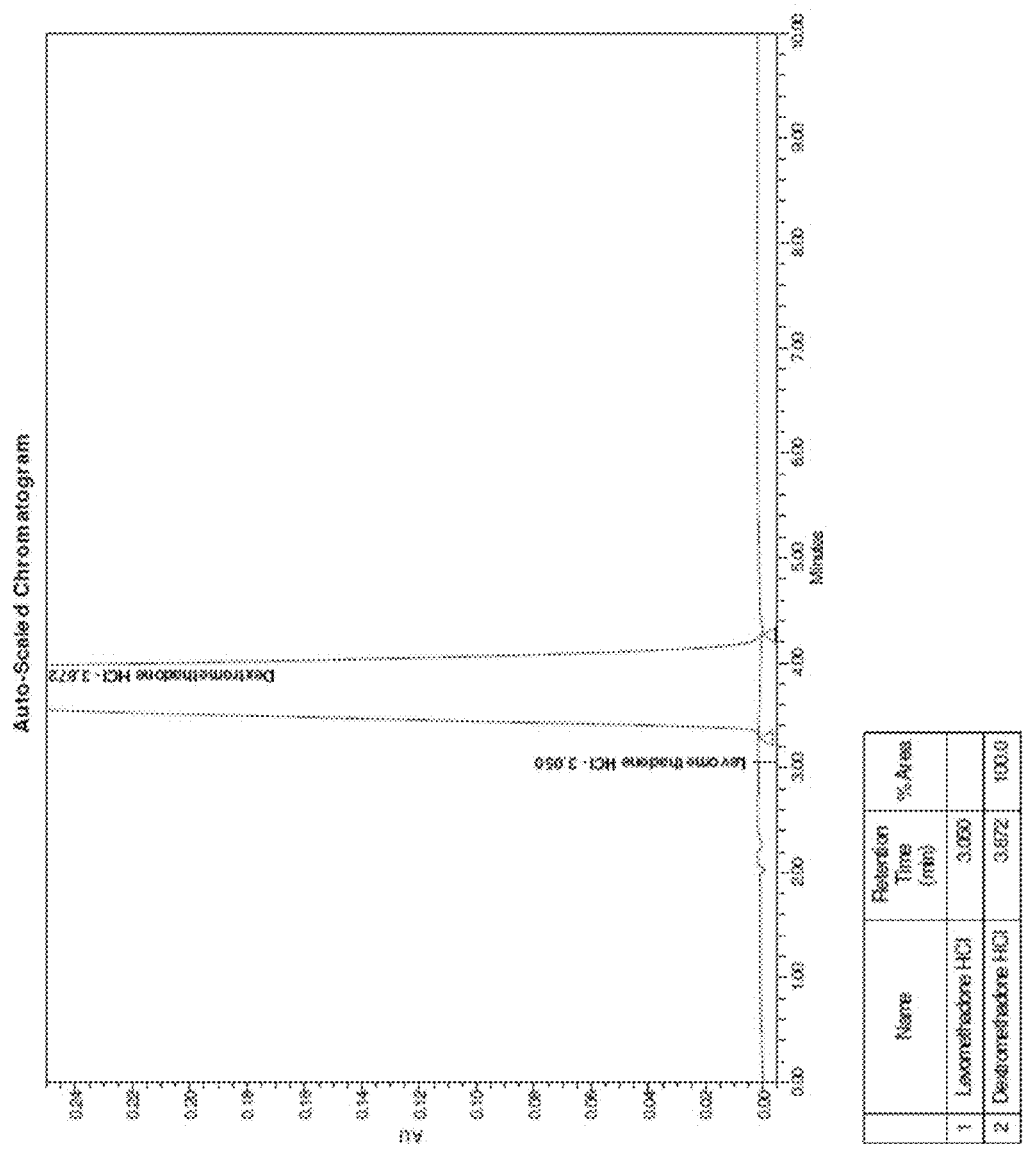

FIG. 26B shows a chiral chromatogram of dextromethadone hydrochloride prepared according to the disclosure.

DETAILED DESCRIPTION

Definitions

As used herein, the terms "administration" and "administering" refer to the act of giving a drug, prodrug, or other agent, or therapeutic treatment (e.g., compositions of the present application) to a subject (e.g., a subject or in vivo, in vitro, or ex vivo cells, tissues, and organs). Exemplary routes of administration to the human body can be through the eyes (ophthalmic), mouth (oral, e.g., immediate release, controlled release, fast melt, etc.), skin (topical or transdermal or sublingual), nose (nasal), lungs (inhalant), oral mucosa (buccal), ear, rectal, vaginal, by injection (e.g., intravenously, subcutaneously, intratumorally, intraperitoneally, intramuscularly, etc.) and the like.

The term "comprising" refers to a composition, compound, formulation or method that is inclusive and does not exclude additional elements or method steps.

The term "consisting of" refers to a compound, composition, formulation, or method that excludes the presence of any additional component or method steps.

The term "consisting essentially of" refers to a composition, compound, formulation or method that is inclusive of additional elements or method steps that do not materially affect the characteristic(s) of the composition, compound, formulation or method.

The term "compound(s)" refers to any one or more chemical entity, pharmaceutical, drug, and the like that can be used to treat or prevent a disease, addiction, illness, sickness, or disorder of bodily function. Compounds comprise both known and potential therapeutic compounds. A compound can be determined to be therapeutic by screening using the screening methods of the present application. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease or condition (e.g., chronic pain).

The terms "analog" and "derivative" are interchangeable and refer to a natural or non-natural modification of at least one position of a given molecule. For example, a derivative of a given compound or molecule is modified either by addition of a functional group or atom, removal of a functional group or atom or change of a functional group or atom to a different functional group or atom (including, but not limited to, isotopes).

The term "composition(s)" refers to the combination of one or more compounds with or without another agent, such as but not limited to a carrier agent. (e.g., one or more levomethadone compounds with a carrier, inert or active), making the composition especially suitable for diagnostic or therapeutic use in vitro, in vivo or ex vivo.

The term "component" refers to a constituent part of a compound, or a composition. For example, components of a composition can include a compound, a carrier, and any other agent present in the composition.

The term "effective amount" refers to the amount of a composition or compound sufficient to effect beneficial or desired results. An effective amount can be administered in one or more applications or dosages and is not intended to be limited to a particular formulation or administration route.

Opioid receptor agonists (sometimes abbreviated as opioid agonists, or "opioids") can also be called opiates.

The term "hydrate" refers to a compound disclosed herein which is associated with water in the molecular form, i.e., in which the H—OH bond is not split, and may be represented, for example, by the formula R×H$_2$O, where R is a compound disclosed herein. A given compound may form more than one hydrate including, for example, monohydrates (R×H$_2$O), dihydrates (R$_2$×2 H$_2$O), trihydrates (R$_3$×3 H$_2$O), and the like. The term "inhibitory" or "antagonistic" refers to the property of a compound that decreases, limits, or blocks the action or function of another compound.

The term "modulates" refers to a change in the state (e.g. activity or amount) of a compound from a known or determined state.

"Optional" or "optionally" refers to a circumstance in which the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The terms "patient" or "subject" are used interchangeably and refer to any member of Kingdom Animalia. Preferably a subject is a mammal, such as a human, domesticated mammal or a livestock mammal.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ration.

The phrase "pharmaceutically-acceptable carrier" refers to a pharmaceutically-acceptable material, composition or vehicle, such as a liquid or solid filler, diluent, excipient, solvent or encapsulating material, involved in carrying or transporting the subject selenium containing compound or analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose, microcrystalline ecellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin (glycerol), sorbitol, mannitol and polyethylene glycol; (12) esters, such as ethyl oleate and ethyl laurate; (13) agar; (14) buffering agents, such as magnesium hydroxide and aluminum hydroxide; (15) lubricants, such as magnesium stearate, calcium stearate, zinc stearate, sorbitan monostearate, sucrose monopalmitate, glycerol dibehenate, and stearic acid; (16) alginic acid; (17) pyrogen-free sterile water; (18) isotonic saline; (19) Ringer's solution; (20) ethyl alcohol; (21) phosphate buffer solutions; (22) polymers and time release agents; (23) bioavailability enhancers and bioavailability controllers/inhibitors; and (23) other non-toxic compatible substances employed in pharmaceutical formulations.

The term "ppm" refers to parts per million. For example, as used to refer to an impurity such as dextromethadone, "ppm" means parts per million of dextromethadone in a particular sample.

The term "salts" can include acid addition salts or addition salts of free bases. Preferably, the salts are pharmaceutically acceptable. Examples of acids which may be employed to form pharmaceutically acceptable acid addition salts include, but are not limited to, salts derived from nontoxic inorganic acids such as nitric, phosphoric, sulfuric, or hydroiodic, hydrobromic, hydrochloric, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, trifluoroacetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, et al. "Pharmaceutical Salts," *J. Pharma. Sci.* 1977; 66:1).

The term "pharmaceutically acceptable salts" includes, but is not limited to, salts well known to those skilled in the art, for example, mono-salts (e.g. alkali metal and ammonium salts) and poly salts (e.g. di- or tri-salts,) of the compounds of the invention. Pharmaceutically acceptable salts of compounds of the disclosure are where, for example, an exchangeable group, such as hydrogen in —OH, —NH—, or —P(=O)(OH)—, is replaced with a pharmaceutically acceptable cation (e.g. a sodium, potassium, or ammonium ion) and can be conveniently be prepared from a corresponding compound disclosed herein by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, hydrobromide, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The term "substituted" in connection with a moiety refers to a further substituent which is attached to the moiety at any acceptable location on the moiety. Unless otherwise indicated, moieties can bond through a carbon, nitrogen, oxygen, sulfur, or any other acceptable atom. Examples of substituents include, but are not limited to amines, alcohols, thiols, ethers, alkenes, alkynes, epoxides, aziridines, oxiranes, azetidines, dihydrofurans, pyrrolidines, pyrans, piperidines, aldehydes, ketones, esters, carboxylic acids, carboxylates, imines, imides, azides, azo groups, eneamines, alkyl halides, alkenyl halides, alkynyl halides, aryl halides, phosphines, phosphine oxides, phophinites, phosphonites, phosphites, phohsphonates, phosphates, sulfates, sulfoxides, sulfonyl groups, sulfoxyl groups, sulfonates, nitrates, nitrites, nitriles, nitro groups, nitroso groups, cyanates, thiocyanates, isothiocyanates, carbonates, acyl halides, peroxides, hydroperoxides, hemiacetals, hemiketals, acetals, ketals, orthoesters, orthocarbonate esters, sulfides, disulfides, sulfonic acids, sulfonic acids, thiones, thials, phosphodiesters, boronic acids, and boronic esters.

The terms "treating", "treat" or "treatment" refer to therapeutic treatment where the object is to slow down (e.g., lessen or postpone the onset of) an undesired physiological condition, disorder or disease, or to obtain beneficial or desired results such as partial or total restoration or inhibition in decline of a parameter, value, function or result that had or would become abnormal. Beneficial or desired results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease.

The term "toxic" refers to any detrimental or harmful effects on a subject, a cell, or a tissue as compared to the same cell or tissue prior to the administration of the toxicant.

The term "prodrug" refers to a pharmacologically active or more typically an inactive compound that is converted into a pharmacologically active agent by a metabolic transformation. Prodrugs of a compound of any of the formulae above are prepared by modifying functional groups present in the compound of any of the formulae above in such a way that the modifications may be cleaved in vivo to release the parent compound. In vivo, a prodrug readily undergoes chemical changes under physiological conditions (e.g., are hydrolyzed or acted on by naturally occurring enzyme(s)) resulting in liberation of the pharmacologically active agent. Prodrugs include compounds of any of the formulae above wherein a hydroxy, amino, or carboxy group is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of any of the formulae above or any other derivative which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

The term "purified" or "to purify" or "substantially purified" refers to the removal of inactive or inhibitory components or impurities (e.g., contaminants) from a composition to the extent that 10% or less, e.g., 10%, 9%, 8%, 7%, 6%, 5%, 4%, 3%, 2%, 1%, 0.5%, 0.1%, 0.05%(500 ppm), 0.025%(250 ppm), 0.01%(100 ppm), 0.005%(50 ppm), 0.0025%(25 ppm), 0.001%(10 ppm), 0.0005%(5 ppm), 0.0001%(1 ppm) or less, of the composition is not active compounds or pharmaceutically acceptable carrier.

The term "isolated" refers to the separation of a material or compound from at least one other material or compound in a mixture or from materials or compounds that are naturally associated with the material or compound. For example, a compound synthesized synthetically is separated from a starting material or an intermediate.

The term "alkyl" refers to a branched or unbranched saturated hydrocarbon group of 1 to 24 carbon atoms. Preferred "alkyl" groups herein contain 1 to 16 carbon atoms; i.e. $C_{1-16}$ alkyl. Examples of an alkyl group include, but are not limited to, methyl, ethyl, propyl, iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl. Most preferred are "lower alkyl" which refer to an alkyl group of one to six, more preferably one to four, carbon atoms. The alkyl group may be optionally substituted with an acyl, amino, amido, azido, carboxyl, alkyl, aryl, halo, guanidinyl, oxo, sulfanyl, sulfenyl, sulfonyl, heterocyclyl, heteroaryl, or hydroxyl group.

The term "alkali metal" refers to metallic salts include, but are not limited to, appropriate alkali metal (group la) salts, alkaline earth metal (group IIa) salts, and other physiological acceptable metals. Such salts can be made from aluminum, calcium, lithium, magnesium, potassium, sodium and zinc.

The term "alkenyl" refers to a straight or branched carbon chain containing at least one carbon-carbon double bond. In exemplary embodiments, "alkenyl" refers to a hydrocarbon containing 2, 3, 4, 5, 6, 7, 8, 9 or 10 carbon atoms, i.e. $C_{1-10}$ alkenyl. Examples of an alkenyl group include, but are not limited to, ethene, propene, butene, pentene, hexene, heptene, octene, nonene and decene. In some embodiments, the alkenyl group is a vinyl or allyl group. The alkenyl group may be optionally substituted with an amino, alkyl, halo, or hydroxyl group.

The term "amido" refers to either a C-amido group such as —CONR'R" or an N amido group such as —NR'COR" wherein R' and R" as used in this definition are independently hydrogen, alkyl, alkenyl, alkynyl, alkoxy, carbocyclic, heterocyclic, aryl, or aralkyl. A "sulfoamido" group includes the —NR'—SO$_2$—R". Most preferably, R' and R" are hydrogen, alkyl, aryl, or aralkyl.

The term "alkynyl" refers to a straight or branched carbon chain containing at least one carbon-carbon triple bond. In exemplary embodiments, "alkynyl" refers to a hydrocarbon containing 2, 3, 4, 5, 6, 7, 8, 9 or 10 carbon atoms, i.e., $C_{2-10}$ alkynyl. Examples of an alkynyl group include, but are not limited to, ethyne, propyne, butyne, pentyne, hexyne, heptyne, octyne, nonyne and decyne. The alkynyl group may be optionally substituted with an amino, alkyl, halo, or hydroxyl group.

The term "aryl" refers to a carbocyclic aromatic system containing one, two or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, tetralin, indane, indene, and biphenyl. The aryl group may optionally be substituted with an amino, alkyl, halo, hydroxyl, carbocyclic, heterocyclic, or another aryl group.

The term "cycloalkyl" refers to a monocyclic saturated or partially saturated carbon ring, wherein the number of ring atoms is indicated by a range of numbers. In exemplary embodiments, "cycloalkyl" refers to a carbon ring as defined above containing 3-12 ring atoms (i.e. $C_{3-12}$ cycloalkyl). As used herein, cycloalkyl encompasses monocyclo, bridged, spiro, fused, bicyclo and tricyclo ring structures. Examples of a cycloalkyl group include, but are not limited to, cyclopropyl, cyclobutyl, cyclopentyl, cyclopentenyl, cyclohexyl, cyclohexenyl, cycloheptyl, cycloheptenyl, norbornyl, decalin, adamantyl, and cyclooctyl. The cycloalkyl group may be optionally substituted with an amino, alkyl, halo, or hydroxyl group.

The term "aralkyl" refers to aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" refers to aryl groups, as defined above, attached to an oxygen atom. The aryloxy groups may optionally be substituted with a halo, hydroxyl, or alkyl group. Examples of such groups include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "alkoxy" refers to oxy-containing groups substituted with an alkyl, or cycloalkyl group. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, isopropoxy, and tert-butoxy groups.

The term "aralkoxy" refers to oxy-containing aralkyl groups attached through an oxygen atom to other groups. "Lower aralkoxy" groups are those phenyl groups attached to lower alkoxy group as described above. Examples of such groups include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "acyl" refers to —C(=O)R wherein R used in this definition is hydrogen, alkyl, alkenyl, alkynyl, carbocyclic, heterocyclic, aryl, or aralkyl. Most preferably, R is hydrogen, alkyl, aryl, or aralkyl.

The term "carboxyl" refers to —R'C(=O)OR", wherein R' and R" as used in this definition are independently hydrogen, alkyl, alkenyl, alkynyl, carbocyclic, heterocylic, heterocyloalkyl, aryl, ether, or aralkyl, or R' can additionally be a covalent bond. "Carboxyl" includes both carboxylic acids, and carboxylic acid esters. The term "carboxylic acid" refers to a carboxyl group in which R" is hydrogen, or a salt. Such acids include formic, acetic, propionic, butryic, valeric acid, 2-methyl propionic acid, oxirane-carboxylic acid, and cyclopropane carboxylic acid. The term "carboxylic acid ester" or "ester" refers to a carboxyl group in which R" is alkyl, alkenyl, alkynyl, carbocyclic, heterocyclic, aryl, or aralkyl. Examples of carboxylic acids include, but are not limited to formic acid, acetic acid, propionic acid, butanoic acid, pentanoic acid, hexanoic acid, heptanoic acid, octanoic acid, nonanoic acid, decanoic acid, cyclopropanecarboxylic acid, cyclobutanecarboxylic acid, cyclopentanecarboxylic acid, cyclohexanecarboxylic acid, cycloheptanecarboxylic acid, cyclooctanecarboxylic acid, or cyclononanecarboxylic acid.

The term "carbonyl" refers to refers to a C=O moiety, also known as an "oxo" group.

The term "heterocycle" or "heterocyclyl" or "heterocyclic ring" or "het" refers to an optionally substituted, saturated or unsaturated, aromatic or non-aromatic cyclic hydrocarbon with 3 to 12, or 5 to 6, carbon atoms, wherein at least one of the ring atoms is an O, N, S, P or Se. For example, in some embodiments, a ring N atom from the heterocyclyl is the bonding atom to —C(O) to form an amide, carbamate, or urea. In exemplary embodiments, "heterocyclyl" refers to a cyclic hydrocarbon as described above containing 4, 5, or 6 ring atoms (i.e., $C_{4-6}$ heterocyclyl). Examples of a heterocyclic group include, but are not limited to, aziridine, oxirane, thiirane, azetidine, oxetane, thietane, pyrrolidine, imidazole, tetrahydrofuran, pyran, thiopyran, thiomorpholine, thiomorpholine S-oxide, oxazoline, tetrahydrothiophene, piperidine, tetrahydropyran, thiane, imidazolidine, oxodioxolenyl, oxazolidine, thiazolidine, dioxolane, dithiolane, piperazine, oxazine, dithiane, dioxane, pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrazolyl. Exemplary heterocycles include benzimidazole, dihydrothiophene, dioxin, dioxane, dioxolane, dithiane, dithiazine, dithiazole, dithiolane, furan, indole, 3-H indazole, 3-H- indole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidinyl, pyridazine, pyrrole, pyrrolidine, tetrahydrofuran, tetrazine, thiadiazine, thiadiazole, thiatriazole, thiazine, thiazole, thiophene, triazine, and triazole. The heterocycle may be optionally substituted with an amino, alkyl, alkenyl, alkynyl, halo, hydroxyl, carbocyclic, thio, other heterocyclic, or aryl group. In some embodiments, the heterocyclyl is unsubstituted.

The term "heteroaryl" refers to a cyclic hydrocarbon, where at least one of the ring atoms is an O, N, S, P or Se, the ring is characterized by delocalized [pi] electrons (aromaticity) shared among the ring members, and wherein the number of ring atoms is indicated by a range of numbers. Heteroaryl moieties as defined herein have C, N, S, P or Se bonding hands. For example, in some embodiments, a ring N atom from the heteroaryl is the bonding atom to —C(O) to form an amide, carbamate, or urea. In exemplary embodiments, "heteroaryl" refers to a cyclic hydrocarbon as described above containing 5 or 6 ring atoms (i.e. $C_{5-6}$ heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine. The heteroaryl may be optionally substituted with an amino, alkyl, alkenyl, alkynyl, halo, hydroxyl, carbocyclic, thio, other heterocyclic, or aryl group. In some embodiments, the heteroaryl is substituted or unsubstituted heteroaryl. In some embodiments, the heteroaryl comprises an optionally substituted $C_{5-6}$ heteroaryl comprising one or more N, S, or O ring atoms.

The term "hydroxy" or "hydroxyl" refers to the substituent —OH.

The term "oxo" refers to the substituent ═O.

The term "nitro" refers to $NO_2$.

The term "azido" refers to $N_3$.

The term "sulfur analog(s)" refers to an analogue of a compound of interest in which one or more selenium atoms have been replaced by one or more sulfur atoms, respectively.

The term "sulfanyl" refers to —SR' where R' as used in this definition is hydrogen, alkyl, alkenyl, alkynyl, carbocyclic, heterocyclic, aryl, or aralkyl.

The term "sulfenyl" refers to —SOR' where R' as used is this definition is hydrogen, alkyl, alkenyl, alkynyl, carbocyclic, heterocyclic, aryl, or aralkyl.

The term "sulfonyl" refers to —$SO_2$R' where R' refers to hydrogen, alkyl, alkenyl, alkynyl, carbocyclic, heterocyclic, aryl, or aralkyl. In particular embodiments, R' is methyl, trifluoromethyl, benzyl, or 4-methylbenzyl.

The term "ketone" refers to a moiety containing at least one carbonyl group where the carbonyl carbon is bound to two other carbon atoms. In exemplary embodiments, "ketone" refers to a carbonyl-containing moiety as described above containing 3, 4, 5, 6, 7, 8, 9 or 10 carbon atoms (i.e. $C_{3-10}$ ketone). Examples of a ketone group include, but are not limited to, acetone, butanone, pentanone, hexanone, heptanone, octanone, nonanone, decanone, cyclobutanone, cyclopentanone, cyclohexanone, cycloheptanone, cyclooctanone, cyclononanone and cyclodecanone.

The term "amino" refers to a primary, secondary or tertiary amino group of the formula —NR'R" wherein R' and R" as used in this definition are independently hydrogen, acyl, alkyl, alkyenyl, alkynyl, aralkyl, aryl, carboxyl, cycloalkyl, heterocyclic, or other amino (in the case of hydrazide) or R' and R" together with the nitrogen atom to which they are attached, form a ring having 4-8 atoms. Thus, the term "amino", includes unsubstituted, monosubstituted (e.g., monoalkylamino or monoarylamino), and disubstituted (e.g., dialkylamino or aralkylamino) amino groups. Amino groups include —$NH_2$, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "amine" refers to a primary, secondary or tertiary amino group of the formula —NR'R" wherein R' and R" as used in this definition are independently hydrogen, acyl, alkyl, alkyenyl, alkynyl, aralkyl, aryl, carboxyl, cycloalkyl, heterocyclic, or other amino (in the case of hydrazide) or R' and R" together with the nitrogen atom to which they are attached, form a ring having 4-8 atoms. Thus, the term "amino", as used herein, includes unsubstituted, monosubstituted (e.g., monoalkylamino or monoarylamino), and disubstituted (e.g., dialkylamino or aralkylamino) amino groups. Amino groups include —$NH_2$, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alcohol" refers to "hydroxy" or "hydroxyl" refers to the substituent —OH.

The term "amino alcohol" refers to a functional group containing both an alcohol and an amine group. As used herein, "amino alcohols" also refers to amino acids as defined above having a carbon bound to an alcohol in place of the carboxylic acid group. In exemplary embodiments, the term "amino alcohol" refers to an amino alcohol as defined above wherein the amine is bound to the carbon adjacent to the alcohol-bearing carbon. In exemplary embodiments, "amino alcohol" refers to an amine and alcohol-containing moiety as described above containing 1, 2, 3, 4, 5, 6, 7, 8, 9, 10, 11 or 12 carbon atoms (i.e., $C_{1-12}$ amino alcohol). Examples of amino alcohols include, but are not limited to, ethanolamine, heptaminol, isoetarine, norepinephrine, propanolamine, sphingosine, methanolamine, 2-amino-4-mercaptobutan-1-ol, 2-amino-4-(methylthio)butan-1-ol, cysteinol, phenylglycinol, prolinol, 2-amino-3-phenyl-1-propanol, 2-amino-1-propanol, cyclohexylglycinol, 4-hydroxy-prolinol, leucinol, tert-leucinol, phenylalaninol, a-phenylglycinol, 2-pyrrolidinemethanol, tyrosinol, valinol, serinol, 2-dimethylaminoethanol, histidinol, isoleucinol, leucinol, methioninol, 1-methyl-2-pyrrolidinemethanol, threoninol, tryptophanol, alaninol, argininol, glycinol, glutaminol, 4-amino-5-hydroxypentanamide, 4-amino-5-hydroxypentanoic acid, 3-amino-4-hydroxybutanoic acid, lysinol, 3-amino-4-hydroxybutanamide, and 4-hydroxy-prolinol.

The term "amino acid" refers to a group containing a carboxylic acid and an amine bound to the carbon atom immediately adjacent to the carboxylate group, and includes both natural and synthetic amino acids. Examples of amino acids include, but are not limited to, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan. The carboxyl is substituted with H, a salt, ester, alkyl, or aralkyl. The amino group is substituted with H, acyl, alkyl, alkenyl, alkynyl, carboxyl, cycloalkyl, aralkyl, or heterocyclyl.

The term "ether" refers to the group —R'—O—R" wherein R' and R" as used in this definition are independently hydrogen, alkyl, alkenyl, alkynyl, carbocyclic, heterocylic, aryl, or aralkyl, and R' can additionally be a covalent bond attached to a carbon.

The term "halogen" refers to a fluorine, chlorine, bromine or iodine atom.

The term "halide" or "halo" refers to a functional group containing an atom bond to a fluorine, chlorine, bromine or iodine atom. Exemplary embodiments disclosed herein may include "alkyl halide," "alkenyl halide," "alkynyl halide," "cycloalkyl halide," "heterocyclyl halide," or "heteroaryl halide" groups. In exemplary embodiments, "alkyl halide" refers to a moiety containing a carbon-halogen bond containing 1, 2, 3, 4, 5, 6, 7, 8, 9 or 10 carbon atoms (i.e., $C_{1-10}$ alkyl halide). Examples of an alkyl halide group include, but are not limited to, fluoromethyl, fluoroethyl, chloromethyl, chloroethyl, bromomethyl, bromoethyl, iodomethyl and iodoethyl groups. Unless otherwise indicated, any carbon-containing group referred to herein can contain one or more carbon-halogen bonds. By way of non-limiting example, a $C_1$ alkyl group can be, but is not limited to, methyl, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, chlorofluoromethyl, dichlorofluoromethyl, and difluorochloromethyl.

In the compounds described herein, heteroatoms are capable of bearing multiple different valencies. By way of non-limiting example, S, Se and N can be neutral or hold a positive charge, and O can be neutral or hold a positive or negative charge.

Regioisomers or regio-isomers are structural isomers that are positional isomers consisting of different compounds with the same molecular formula comprising one or more functional group(s) or other substituent(s) that change(s) position on a parent structure.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties.

Unless otherwise specified, when a compound having "not more than x %" or "not more than y ppm" of an impurity is disclosed, the x % or y ppm refers to the area of the principle peak in a chromatogram obtained with the reference compound. Unless otherwise specified, the chromatogram is an HPLC chromatogram.

The term "levomethadone" refers to (6R)-6-(dimethylamino)-4,4-diphenylheptan-3-one.

The term "dextromethadone" refers to (6S)-6-(dimethylamino)-4,4-diphenylheptan-3-one.

The term "levomethadone hydrochloride" refers to (6R)-6-(dimethylamino)-4,4-diphenylheptan-3-one hydrochloride; also known as (−)-(R)-6-(dimethylamino)-4,4-diphenyl-3-heptanone.

The term "dextromethadone hydrochloride" refers to (6S)-6-(dimethylamino)-4,4-diphenylheptan-3-one hydrochloride; also known as (+)-(S)-6-(dimethylamino)-4,4-diphenyl-3-heptanone.

The term "levomethadone nitrile" refers to (4R)-4-(dimethylamino)-2,2-diphenylpentanenitrile.

The term "dextromethadone nitrile" refers to (4S)-4-(dimethylamino)2,2-diphenylpentanenitrile.

The term "N,N-dimethyl D-alaninol" refers to (R)-2-(dimethylamino)propan-1-ol.

The term "N,N-dimethyl L-alaninol" refers to (S)-2-(dimethylamino)propan-1-ol.

The term "isolevomethadone nitrile" refers to (3R)-isomethadone nitrile, to (3R)-4-(dimethylamino)-3-methyl-2,2-diphenylbutanenitrile.

The term "isodextromethadone nitrile" refers to (3S)-isomethadone nitrile, or (3S)-4-(dimethylamino)-3-methyl-2,2-diphenylbutanenitrile.

The term "isolevomethadone" refers to (5R)-isomethadone, (5R)-6-(dimethylamino)-5-methyl-4,4-diphenylhexan-3-one.

The term "isodextromethadone" refers to (5S)-6-(dimethylamino)-4,4-diphenylheptan-3-one.

The term "diphenylacetonitrile refers to 2,2-diphenylacetonitrile.

The term "catalyst" or "cat." refers to a substance that speeds up a chemical reaction, but is not consumed by the reaction. As used herein, unless otherwise specified, examples of a catalyst include palladium on active carbon (Pd/C), Pd/C/FeCl$_3$, Pd/C/Fe(III) hydroxide or oxide, Pd/Al$_2$O$_3$, Pt/C, Pt/Al$_2$O$_3$, Pd/BaSO$_4$, Raney Ni-catalyst, Urushibara Ni-catalyst, rhodium on active carbon, Raney nickel, ruthenium black, PtO$_2$, Pt/C and platinum black, ZnCl$_2$, and Zn. In specific embodiments, the catalyst is a palladium on carbon Pd/C catalyst selected from 2% Pd/C, 2.5% Pd/C, 3% Pd/C, 5% Pd/C, 10% Pd/C, or 5% Pd/BaSO$_4$. In a specific embodiment, the catalyst is palladium on charcoal (Pd/C) wet catalyst (for example, 10% catalyst, LOD 50%).

The term "reducing agent" refers to a reducing agent selected from the group consisting of lithium aluminum hydride (LiAlH$_4$), borane tetrahydrofuran complex solution (BH$_3$/THF), borane diethyl ether complex solution (BH$_3$/Et$_2$O), borane/boron trifluoride diethyl etherate (BH$_3$/BF$_3$ Et$_2$O), borane dimethyl sulfide complex (BH$_3$/Me$_2$S), sodium borohydride and iodine (NaBH$_4$/I$_2$), sodium borohydride and sulfuric acid (NaBH$_4$/H$_2$SO$_4$), NaBH$_4$/cyanuric chloride, sodium cyanoborohydride and zinc chloride (NaBH$_3$CN/ZnCl$_2$), sodium borohydride and zinc chloride (NaBH$_4$/ZnCl$_2$), zinc borohydride (Zn(BH$_4$)$_2$), and sodium borohydride boron trifluoride etherate (NaBH$_4$/BF$_3$.EtO).

The term "alcoholic solvent" refers to a solvent comprising a hydroxyl group attached to a carbon atom. In some embodiments, the alcoholic solvent is selected from methanol, ethanol, isopropyl alcohol, tert-amyl alcohol, benzyl alcohol, isobutanol, 2-butanol, n-butanol, and tert-butanol.

The term "polar aprotic solvent" is used to refer to any known polar aprotic solvent. In some embodiments, the polar aprotic solvent is selected from 1,4-dioxane, tetrahydrofuran, ethyl acetate, acetone, N,N-dimethylformamide, N-methylformamide, dimethylacetamide, N-methylpyrrolidone, acetonitrile, and dimethylsulfoxide.

The term "hydrocarbon solvent" refers to any known hydrocarbon solvent. In some embodiments, the hydrocarbon solvent is selected from benzene, cyclohexane, hexane, ligroin, pentane, heptane, petroleum ether, toluene, or xylene.

The term "halogenated solvent" refers to any known halogenated solvent. In some embodiments, the halogenated solvent is selected from dichloromethane, chloroform, 1,2-dichloroethane and benzotrifluoride (α,α,α-trifluorotoluene).

The term "ether solvent" refers to a solvent comprising an ether moiety (C—O—C bonds). In some embodiments, the ether solvent is selected from diethyl ether, diisopropyl ether, THF, DME, dioxane, and MTBE.

The term "acid" refers to a Bronsted-Lowry acid that is capable of releasing a proton, H+ ion. In some embodiments, the acid is an organic acid that is an organic compound with acidic properties comprising one or more carbon atoms, for example, formic acid, acetic acid, trifluoroacetic acid, propionic acid, butyric acid, valeric acid, caproic acid, oxalic acid, lactic acid, malic acid, citric acid, benzoic acid, carbonic acid, phenol, uric acid, taurine, trifluoromethanesulfonic acid, and aminomethylphosphonic acid. In some embodiments, the acid is an organic carboxylic acid. In some embodiments, the organic carboxylic acid is selected from formic acid, acetic acid, trifluoroacetic acid, propionic acid, butyric acid, valeric acid, caproic acid, oxalic acid, lactic acid, malic acid, citric acid, and benzoic acid. In some embodiments, the acid is an inorganic acid or mineral acid, for example, sulfuric acid, hydrochloric acid, nitric acid, phosphoric acid, boric acid, hydrofluoric acid, hydrobromic acid, and perchloric acid.

The term "base" refers to a Bronsted-Lowry base that is capable of accepting H+ ions. In some embodiments, a base is selected from sodium hydroxide (NaOH), potassium hydroxide (KOH), calcium hydroxide (Ca(OH)$_2$), sodium carbonate (Na$_2$CO$_3$), potassium carbonate (K$_2$CO$_3$), sodium bicarbonate (NaHCO$_3$), potassium bicarbonate (KHCO$_3$), trisodium phosphate (Na$_3$PO$_4$), tripotassium phosphate (K$_3$PO$_4$), disodium phosphate (Na$_2$HPO$_4$), dipotassium phosphate (K$_2$HPO$_4$), sodium acetate (NaOAc), potassium acetate (KOAc), potassium tert-butoxide (KOtBu), sodium tert-butoxide (NaOtBu), other potassium and sodium alkoxides such as sodium methoxide, potassium methoxide, sodium ethoxide, potassium ethoxide, sodium isopropoxide, sodium tert-pentoxide (sodium tert-amoxide), potassium tert-pentoxide (potassium tert-amoxide), and potassium isopropoxide; or lithium alkoxides such as lithium methoxide, or lithium tert-butoxide; or organolithium compounds such as methyllithium, n-butyllithium, sec-butyllithium, isopropyllithium, tert-butyllithium, or phenyllithium; or a lithium amide. In some embodiments, a weak base is selected from TEA and DIEA.

The term "Grignard reagent" as used herein refers to a reagent which may be generated by any known method, generated in situ, or a commercial reagent of formula RMgX where R is an alkyl, alkenyl, or aryl group, and X is I, Br, or Cl. In some embodiments, the Grignard reagent is made in situ, for example, with magnesium shavings and an alkyl halide, or the Grignard reagent may be purchased as a reagent. In some embodiments, the Grignard reagent is used in a Grignard reaction under anhydrous conditions, for example in an ether solvent, with a nitrile intermediate according to the disclosure, followed by treatment with an acid to form a compound according to the disclosure. In some embodiments, the Grignard reaction is performed with a copper activating compound such as CuBr/H$_3$O+, by the method of Weiberth et al., J Org Chem 52, 3901 (1987), which is incorporated herein by reference. In some embodiments, the Grignard reagent is selected from methylmagnesium bromide, methylmagnesium chloride, ethylmagnesium bromide, ethylmagnesium chloride, phenylmagnesium bromide, and allylmagnesium bromide. In a preferred embodiment, the Grignard reagent is ethyl magnesium bromide (EtMgBr).

As used herein, and unless otherwise specified, "Ac" means acetyl, "aq" means aqueous, "Ar" means argon, "cat." means catalytic, "DCE" means 1,2-dichloroethane, "DCM" means dichloromethane, "DIEA" means diisopropylethylamine, "DME" means 1,2-dimethoxyethane, "DMF" means dimethylformamide, "DMF-DMA" means N,N-dimethylformamide dimethylacetal, "e.e." means enantiomeric excess, "equiv" means equivalent(s), "Et" means ethyl, "EtOAc" means ethyl acetate, "EtOH" means ethanol, "h" or "hr" means hour(s), "KOtBu" or "t-BuOK" means potassium tert-butoxide, "KOH" means potassium hydroxide, "MTBE" means methyl tert-butyl ether, "Me" means methyl, "MeCN" means acetonitrile, "MeOH" means methanol, "min" means minute(s), "Ms" means mesyl (CH$_3$SO$_2$—), "NaOH" means sodium hydroxide, "PE" means petroleum ether, "PPA" means polyphosphoric acid, "RT" or "rt" means room temperature, "t-BuOH" means tert-butanol, "t-BuONa" or "NaOtBu" means sodium tert-butoxide, "TEA" means triethylamine, "TFA" means trifluoroacetic acid, "THF" means tetrahydrofuran, "o-Tol" means o-tolyl (2-CH$_3$C$_6$H$_4$), "p-Tol" means p-tolyl (4-CH$_3$C$_6$H$_4$), and "Ts" means tosyl (p-CH$_3$C$_6$H$_4$SO$_2$—).

The term "NMDA" or "NMDAR" refers to N-methyl-D-aspartate receptor, which is a glutamate receptor subtype. An NMDA receptor antagonist, or NMDA antagonist, is a compound that inhibits the action of the NMDA receptor. NMDA antagonists have been investigated for treatment of anxiety disorders, Alzheimer's disease, chronic pain, dementia, depression, neuropathic pain, anti-NMDA receptor encephalitis, opioid analgesic tolerance, schizophrenia, stroke, and traumatic brain injury.

A chemical term that is not otherwise defined herein is understood as being defined in Hawley's Condensed Chemical Dictionary, 15$^{th}$ Ed. Wiley-Interscience, 2007.

Methods

Highly efficient methods for synthesis of levomethadone hydrochloride or dextromethadone hydrochloride are provided starting from D-alanine, or L-alanine, respectively, with retention of configuration. Methods for treating a subject are provided comprising administering a composition comprising an effective amount of levomethadone hydrochloride having not more than 10 ppm dextromethadone.

Production of Levomethadone Hydrochloride from D-Alanine

Figure 1A:
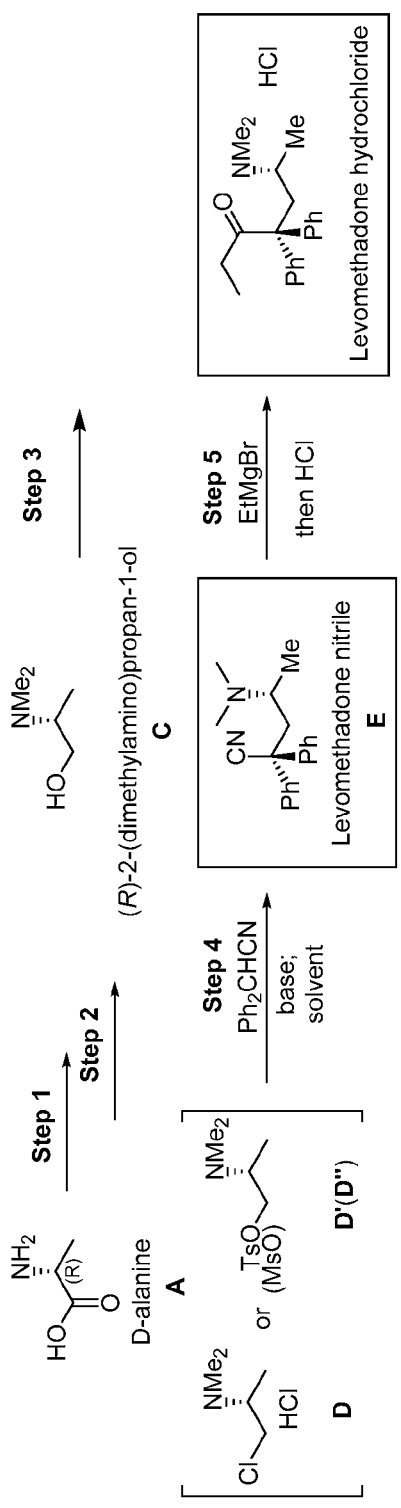
FIG. 1A shows a general synthetic route provided for preparation of levomethadone hydrochloride. (R)-2-N,N-dimethyl alaninol (C) is prepared from D-alanine. An activated intermediate (D, D' or D") of the N,N-dimethyl alaninol is prepared and treated with diphenylacetonitrile to form levomethadone nitrile (E) which is treated with a Grignard reagent, then HCl to form levomethadone hydrochloride.

In one embodiment, a method for preparing levomethadone hydrochloride, or an analog or prodrug thereof, is provided with retention of configuration. FIG. 1A depicts a general synthetic scheme provided for preparation of levomethadone hydrochloride. In the first steps D-alanine (A) is converted to N,N-dimethyl D-alaninol (C). Step 3 comprises activation of N,N-dimethyl D-alaninol (C), by chlorination or formation of a sulfonate ester, and exposing the resultant active intermediate (D or D') to a base and diphenylacetonitrile to form levomethadone nitrile (E). The levomethadone nitrile (E) is treated with a Grignard reagent, then HCl to form levomethadone hydrochloride.

In one embodiment, a highly efficient asymmetric synthesis of levomethadone hydrochloride is provided starting from D-alanine, and resulting in levomethadone hydrochloride in greater than 20%, greater than 30%, or preferably greater than 40% overall yield using readily available chemicals. In some embodiments, a process is provided for the production of levomethadone hydrochloride in 25-60%, 30-50% or 35-45% overall yield from D-alanine, wherein the levomethadone hydrochloride is provided in greater than 95%, 97%, 99% 99.5%, or 99.9% e.e.

In some embodiments, a process is provided for the production of levomethadone hydrochloride in greater than 20%, greater than 30%, or preferably greater than 40% from D-alanine, wherein the levomethadone hydrochloride comprises not more than 0.5%, 0.25%, 0.1%, 0.05%, 0.025%, 0.01%. 0.005%, 0.001%, 0.0005%, or 0.0001% of an impurity selected from dextromethadone, isodextromethadone, isolevomethadone, levomethadone nitrile, dextromethadone nitrile, isolevomethadone nitrile, isodextromethadone nitrile, diphenylacetonitrile, 2(S)-2-[[(4-methylphenyl)sulphonyl] amino]pentanedioic acid (N-tosyl-L-glutamic acid); a tartaric acid, or a bromocamphor sulfonic acid, such as a 3-bromocamphor-10-sulfonic acid.

In some embodiments, a process is provided for the production of levomethadone hydrochloride in greater than 20%, greater than 30%, or preferably greater than 40% from D-alanine, wherein the levomethadone hydrochloride comprises not more than 0.5%, 0.25%, 0.1%, 0.05%, 0.025%, 0.01%. 0.005%, 0.001%, 0.0005%, or 0.0001% of dextromethadone or dextromethadone hydrochloride.

In some embodiments, a process is provided for the production of levomethadone hydrochloride in greater than 95%, 97.5%, or 99% e.e., wherein the levomethadone hydrochloride comprises not more than 10 ppm, 5 ppm, 1 ppm, 0.5 ppm, or no detectable impurity selected from (2S)-2-[[(4-methylphenyl)sulphonyl] amino]pentanedioic acid (N-tosyl-L-glutamic acid); a tartaric acid, or a bromocamphor sulfonic acid, such as a 3-bromocamphor-10-sulfonic acid.

In one embodiment, a preferred chiral route of synthesis to levomethadone hydrochloride from D-alanine is provided, as shown in FIG. 2A, resulting in better than 40% overall yield in >99% e.e.

Synthesis of N,N-Dimethyl-D-Alaninol from D-Alanine

In some embodiments, D-alanine is converted to N,N-dimethyl-D-alaninol in two steps, as shown in FIG. 2B. In one embodiment, D-alanine is treated with zinc borohydride, which is generated in situ by the reaction of sodium borohydride and zinc chloride in THF, to give D-alaninol intermediate which is converted to N,N-dimethyl D-alaninol with formaldehyde and formic acid. In another embodiment, as shown in FIG. 2A, conversion of D-alanine (A) to N,N-dimethyl D-alanine (B) is performed via hydrogenation in the presence of formaldehyde and Pd/C, then reduced to form N,N-dimethyl-D-alaninol. In some embodiments, N,N-dimethyl-D-alaninol is provided in >90% yield, for example, as shown in Example 1.

Figure 1B:
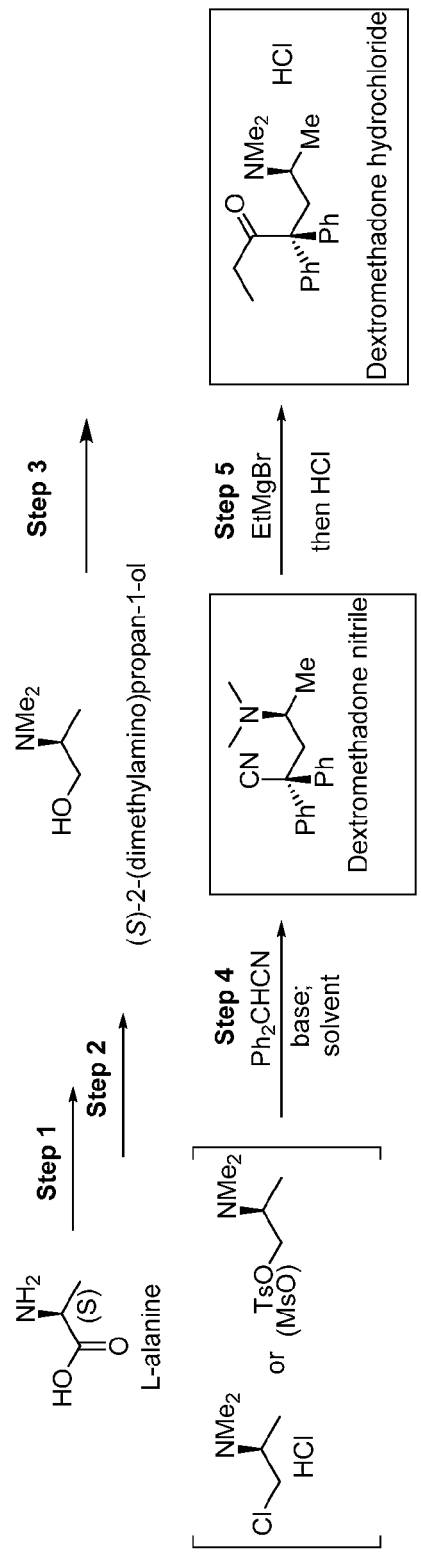
FIG. 1B shows a general synthetic route provided for preparation of dextromethadone hydrochloride. (S)-2-N,N-dimethyl alaninol (C) is prepared from L-alanine. An activated intermediate of the N,N-dimethyl alaninol is prepared and treated with diphenylacetonitrile to form dextromethadone nitrile which is treated with a Grignard reagent, then HCl to form dextromethadone hydrochloride.
Figure 1C:
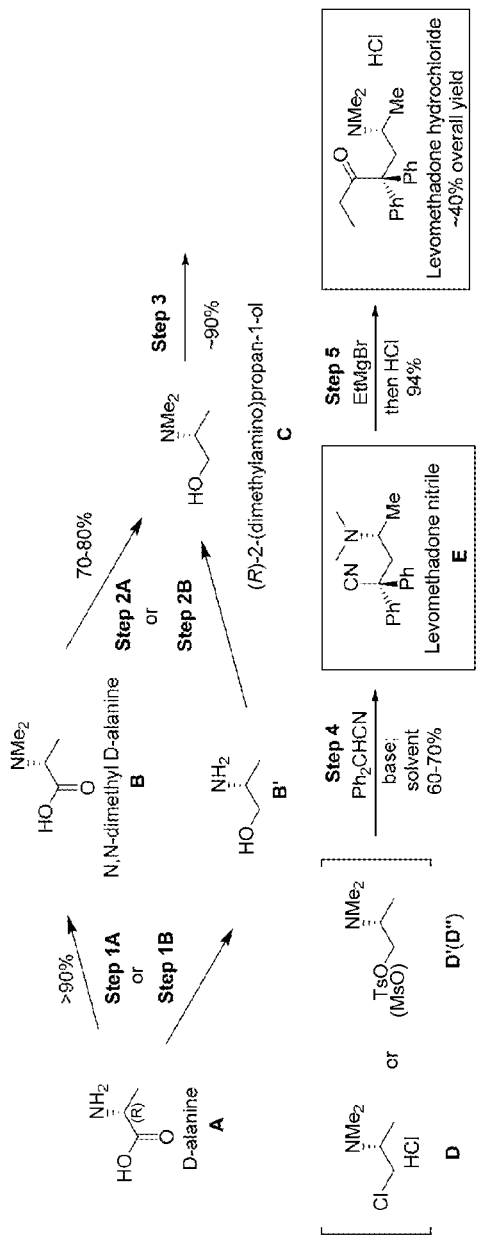
FIG. 1C shows two alternative routes for preparation of levomethadone hydrochloride from D-alanine with retention of configuration.

In some embodiments, as shown in FIG. 1C, D-alanine (A) is converted to dimethyl-D-alanine (B) in step 1A, then reduced to (R)-2-(dimethylamino)propan-1-ol (C) in step 2A. Alternatively, D-alanine (A) is reduced to form D-alaninol in step 1B, then dimethylated to form (R)-2-(dimethylamino)propan-1-ol (C) in step 2B. The (R)-alcohol (C) is activated by chlorination to form intermediate (D), or (C) is converted to a sulfonate ester (e.g., D' or D"). The activated intermediate D, D' or D" is treated with a base and diphenylacetonitrile to form levomethadone nitrile (E; (R)-4-(dimethylamino)-2,2-diphenylpentanenitrile). The nitrile (E) is converted to levomethadone by a Grignard reaction with ethyl magnesium bromide. Levomethadone hydrochloride is produced following exposure to HCl.

In one embodiment, D-alanine (A) is dimethylated to form N,N-dimethyl D-alanine (B) by a modification of any known method, for example, see, WO 2012/162635; and Paterson et al., Org Lett 2013, 15, 3118-3121; each of which is incorporated by reference. In one specific embodiment, D-alanine A is converted to N,N-dimethyl D-alanine B via hydrogenation in the presence of formaldehyde and Pd/C, as shown in FIG. 3 and Example 1. In another embodiment, D-alanine A is converted to N,N-dimethyl D-alanine B with formaldehyde/Zn by a modification of a literature method (Tetrahedron Lett. 2007, 48, 7680-7682). In a further embodiment, D-alanine A is converted to N,N-dimethyl D-alanine B with formaldehyde, $NaBH_4/ZnCl_2$ by a modification of a literature method (Synth. Commun. 1995, 25, 2061-2069). In another embodiment, D-alanine A is converted to N,N-dimethyl D-alanine B with paraformaldehyde, $NaBH_4$ in 2,2,2-trifluoroethanol by a modification of a literature method (Synthesis, 2011, 490-496). In some embodiments, D-alanine (A) is dimethylated to form N,N-dimethyl (D)-alanine (B) in water in the presence of formaldehyde and $H_2$, Pd/C at a temperature of 30-90° C., 40-80° C., or 45-60° C., for example, as shown in Example 1.

In some embodiments, intermediate compound N,N-dimethyl D-alanine (B), is isolated and purified by any known means, including recrystallization and/or chromatography, before employing in the next step. In other embodiments, intermediate compound N,N-dimethyl (D)-alanine (B), is employed in the next step without further purification. In some embodiments, intermediate compound N,N-dimethyl D-alanine (B), is isolated and recrystallized from an alcoholic solvent, a polar aprotic solvent, hydrocarbon solvent, or a mixture of two or more thereof. In some embodiments, compound N,N-dimethyl D-alanine (B) is recrystallized from a mixture of an alcoholic solvent and a polar aprotic solvent. In some embodiments, intermediate compound N,N-dimethyl D-alanine (B) is recrystallized from a mixture of an alcoholic solvent and a polar aprotic solvent in a ratio selected from 1:10 to 10:1, 1:10 to 1:1, 1:2 to 1:8, or 1:5 v/v. In some embodiments, intermediate B is recrystallized from a mixture of an alcoholic solvent and a polar aprotic solvent wherein the alcoholic solvent is selected from methanol, ethanol, isopropyl alcohol, and a mixture thereof; and wherein the polar aprotic solvent is selected from acetone, ethyl acetate, and a mixture thereof. In some embodiments, the crude intermediate B is recrystallized by warming to 30-70° C., 40-60° C., or 50-60° C. in a solvent or solvent mixture and allowed to cool, followed by isolation of crystalline intermediate B.

In some embodiments, N,N-dimethyl D-alanine B, or its acid chloride or alkyl ester derivatives B', is treated with a reducing agent in an ether solvent and or hydrocarbon solvent to form (R)-2-(dimethylamino)propan-1-ol, C, as outlined in FIG. 4. In a specific embodiment, N,N-dimethyl D-alanine B is treated with lithium aluminum hydride, $LiAlH_4$, in a solvent selected from diethyl ether, THF, DME, dioxane, MTBE, or toluene to form (R)-2-(dimethylamino)propan-1-ol, C, for example, as described in Example 2. In some embodiments, (R)-2-(dimethylamino)propan-1-ol, C, is provided by treating N,N-dimethyl D-alanine B with a reducing agent selected from $BH_3$/THF, $BH_3$/$Et_2O$, $BH_3$/$BF_3$ $Et_2O$, or $BH_3$/$Me_2S$ in an ether or hydrocarbon solvent. In some embodiments, (R)-2-(dimethylamino)propan-1-ol, C, is provided by treating N,N-dimethyl D-alanine B with NaBH4/cyanuric chloride in an ether solvent. In some embodiments, (R)-2-(dimethylamino)propan-1-ol, C, is provided by treating N,N-dimethyl D-alanine B with $NaBH_3CN/ZnCl_2$ in an ether solvent and/or an alcoholic solvent. In some embodiments, (R)-2-(dimethylamino)propan-1-ol, C, is provided by treating N,N-dimethyl D-alanine B with $NaBH_4/BF_3.Et_2O$ in an ether solvent, for example by a modification of Organic Chemistry: An Indian Journal, 2012, 8, 1-4. In a specific embodiment, N,N-dimethyl D-alanine B is treated with lithium aluminum hydride, LiAlH$_4$ in THF at 0° C., then heated to reflux for 16 h to form (R)-2-(dimethylamino)propan-1-ol, C, as described in Example 2. In some embodiments, intermediate (R)-2-(dimethylamino)propan-1-ol, C, is isolated as an oil and used directly in the next step.

In another embodiment, as shown in FIGS. 1C and 2B, D-alanine is reduced to D-alaninol with Zn(BH$_4$)$_2$, which can be conveniently prepared from NaBH$_4$ and ZnCl$_2$. The crude D-alaninol obtained in an aqueous media from this reduction process is subjected to an Eschweiler-Clarke Reaction with formaldehyde and formic acid to produce the desired N,N-dimethyl D-alaninol. This synthetic sequence was found to be simple and readily scalable.

In some embodiments, the reduction is run under anhydrous conditions. In other embodiments, the reduction is performed under an inert atmosphere. In a particular aspect, the reaction is run in anhydrous THF. In some aspects, after completion of the reaction, excess borohydride is quenched with methanol and the product, D-alaninol, is liberated as a salt in aqueous medium by treatment with phosphoric acid. In another aspect, the phosphoric acid aids the precipitation of zinc salts such as zinc phosphate. In further aspects, the D-alaninol in aqueous medium is used in the next step without isolation. In another aspect, the method comprises filtration of inorganic salts, and/or precipitation of inorganic salts.

In the second step, D-alaninol is converted to N,N-dimethyl D-alaninol. In some aspects, the conversion comprises reductive alkylation with formaldehyde and formic acid in water as solvent by heating at 110° C. In some aspects, in order to isolate the product, water, formaldehyde and formic acid were removed by evaporation in vacuo, with the product, N,N-dimethyl D-alaninol, maintained in salt form. Residual formaldehyde was optionally further removed by treatment with sodium bisulfite to form a water soluble bisulfite adduct. The product was then extracted with MTBE by evaporating the reaction mixture to a minimal volume of water and basifying to generate the free amino alcohol with a 50% aqueous sodium hydroxide solution.

In a specific embodiment, N,N-dimethyl D-alaninol is prepared from D-alanine in a two-step process. A first step comprises reduction of D-alanine to D-alaninol with Zn(BH$_4$)$_2$ generated in-situ from the reaction of NaBH$_4$ with ZnCl$_2$. In some aspects, the generation of Zn(BH$_4$)$_2$ is run in a solvent selected from diethyl ether, THF, DME, dioxane, MTBE, or toluene for 0.5-24 h, 1-12, 3-6 h at a temperature from 20-50, or 30-45° C. In some aspects, following generation of the Zn(BH$_4$)$_2$, the D-alanine is added to the Zn(BH$_4$)$_2$ at a temperature of not more than about 25° C., then temperature is gradually increased to reflux with evolution of H$_2$. The reaction is allowed to reflux from about 2-16, 3-8 or 4-6 hr, then cooled to 0-25, 4-15 or 5-10° C. prior to quench with methanol. In some aspects, after stirring and dilution with water, phosphoric acid is added to a pH of 3.5-4.0. This aids in precipitating zinc phosphate and keeping D-alaninol in solution as a salt. Following filtration to remove zinc phosphate, the filtrate is neutralized by addition of NaOH to pH 8.5-9.5 to form free amine. The crude D-alaninol is treated with formaldehyde and formic acid and heated to reflux for 6-16 h to form N,N-dimethyl-D-alaninol as a formate salt. Sodium bisulfite is added and reaction stirred for 1-16 h, 2-10, or 3-6 h to ensure removal of formaldehyde. The reaction mixture is concentrated, basified with NaOH, and extracted with MTBE, then dried to form N,N-dimethyl-D-alaninol as an oil.

Preparation of Levomethadone Nitrile from N,N-Dimethyl-D-Alaninol Via Activated Intermediate.

In some embodiments, (R)-2-(dimethylamino) propan-1-ol, C, is converted to levomethadone nitrile E via an activated intermediate, D, or D'(D"), as shown in FIG. 5. In some embodiments, (R)-2-(dimethylamino) propan-1-ol, C, is treated with thionyl chloride, SOCl$_2$, to form the chloro intermediate D, or treated with a sulfonyl chloride to form sulfonyl intermediate D'. The activated intermediate, selected from D or D'(D"), is treated with diphenylacetonitrile and a base to form levomethadone nitrile E.

In some embodiments, the chiral amino alcohol C is converted to chloride D by dissolving in a halogenated solvent, cooling to below room temperature, e.g., from 0-5° C., then adding SOCl$_2$ and heating to 30-70° C., 35-60° C., or to reflux temperature to form chloro intermediate D. In some embodiments, the halogenated solvent is DCM, or CHCl$_3$, or alternatives to chlorinated solvents, for example PhCF$_3$. In some embodiments, the reaction mixture is evaporated and intermediate D is isolated, but not purified prior to performing the next step. In some embodiments, the chiral amino alcohol C is converted to chloride D by treating with SOCl$_2$ at −10-5° C., then heating to 30-70° C., 35-60° C., or to reflux temperature. In some embodiments, chloro intermediate D is treated with diphenyl acetonitrile to give optically pure levomethadone nitrile E in the presence of a suitable base and appropriate solvent(s). In some embodiments, the base is selected from one or more of KOtBu, NaOtBu, other K or Na alkoxides such as methoxide, ethoxide, isopropoxide, tert-pentoxide, KOH, and NaOH. In some embodiments, the solvent is selected from a polar aprotic solvent, an ether solvent, water, or any combination thereof. In some embodiments, the polar aprotic solvent is DMF, DMA, or DMSO. In some embodiments, the ether solvent is THF or dioxane. In a specific embodiment, intermediate D is dissolved in DMF, and treated with KOtBu under Ar to prepare a first reaction mixture, and a separate second reaction mixture of diphenylacetonitrile is prepared in DMF with KOtBu. In some embodiments, the reaction is performed in the presence of a dibenzo 18-crown-6 phase transfer reagent in DMSO/aq NaOH. The second reaction mixture is transferred to the first reaction mixture and allowed to stir at ambient r.t., then heated for 2-24, 4-20, or 5-15 h at a temp of from 30-120° C., 35-75° C., or 40-50° C. to form levomethadone nitrile, E. In some embodiments, the levomethadone nitrile is purified prior to carrying to the next reaction step. In some embodiments, the levomethadone nitrile is purified by chromatography or recrystallization. In some embodiments, the levomethadone nitrile is purified by recrystallization from a hydrocarbon solvent. In some embodiments, the levomethadone nitrile is recrystallized from heptane.

In some embodiments, the levomethadone nitrile, intermediate E, is characterized by one or more of RP-HPLC, chiral HPLC, elemental analysis, specific optical rotation, $^1$H-NMR, and $^{13}$C-NMR. In some embodiments, the levomethadone nitrile prepared by the methods provided herein comprises a single enantiomer (E) in >99% e.e. by chiral HPLC. See intermediate E in FIG. 17, compared to methadone nitrile, shown in FIG. 18. $^1$H-NMR for intermediate E is shown in FIGS. 13 and 14. 13C-NMR of intermediate E is shown in FIGS. 15-16.

In some embodiments, the chiral alcohol C is treated with a sulfonyl chloride, for example para-toluene sulfonyl chloride (TsCl) or methanesulfonyl chloride (MsCl), para-toluene sulfonyl anhydride (Ts anhydride) or methanesulfonyl anhydride (Ms anhydride), to form the activated sulfonyl intermediate D' or D", for example, (R)-2-(dimethylamino) propyl 4-methylbenzenesulfonate, D' or (R)-2-(dimethylamino)propyl methanesulfonate, D". Intermediate D' or D" is treated with diphenyl acetonitrile in the presence of a suitable base in (an) appropriate solvent(s) to give optically pure levomethadone nitrile E. In some embodiments, the solvent is selected from THF, DMF or a mixture thereof. In some embodiments, the ratio of THF:DMF is varied from 1:10 to 10:1 v/v. In specific embodiments, the ratio of THF:DMF is selected from 4:1, 3:1, 2:1, 1:1, 1:2, 1:3 or 1:4. In some embodiments, the base is selected from one or more of KOtBu, NaOtBu, other K or Na alkoxides such as methoxide, ethoxide, isopropoxide, t-pentoxide, KOH, and NaOH. In some embodiments, the solvent is selected from a polar aprotic solvent, an ether solvent, water, or any combination thereof. In some embodiments, the polar aprotic solvent is DMF, DMA, or DMSO. In some embodiments, the ether solvent is THF or dioxane.

In some embodiments, intermediate C, (R)-2-(dimethylamino)propan-1-ol, is activated by treating with a sulfonyl chloride, or sulfonyl anhydride, and a base to form intermediate D', (R)-2-(dimethylamino)propyl 4-methylbenzenesulfonate, or intermediate D", (R)-2-(dimethylamino)propyl methanesulfonate, by as shown in FIG. 5, by methods known in the art. In some embodiments, the sulfonyl chloride is selected from methanesulfonyl chloride or p-tolueneulfonyl chloride.

In some embodiments, N,N-dimethyl D-alaninol is treated with p-toluenesulfonyl chloride (tosyl chloride or TsCl) in the presence of potassium tert-butoxide and the resulting tosylate intermediate is subjected to alkylation with diphenylacetonitrile using potassium tert-butoxide as the base to give levomethadone nitrile along with isolevomethadone nitrile. The undesired isomer, isolevomethadone nitrile, can be removed by recrystallization with an organic solvent such as heptane to give the desired pure levomethadone nitrile.

In another aspect, a "one-pot" procedure for the alcohol activation/alkylation process is performed by pre-mixing of N,N-dimethyl D-alaninol with tosyl chloride in anhydrous THF and subsequent treatment with potassium tert-butoxide to produce a tosylated activated intermediate. The in situ generated tosylate of the amino alcohol is subjected to alkylation with diphenylacetonitrile using potassium tert-butoxide as the base in dimethylformamide (DMF) to give a mixture of levomethadone nitrile and isolevomethadone nitrile in a ratio of approximately 75:25. Pure levomethadone nitrile is obtained by recrystallization from heptane.

In specific embodiments, the N,N-dimethyl-D-alaninol is converted to levomethadone nitrile by first preparing an activated intermediate, then alkylating with diphenylacetonitrile. In some aspects, the N,N-dimethyl-D-alaninol is dissolved in a polar aprotic solvent. In some embodiments, the polar aprotic solvent is selected from THF or DMF. After stirring and cooling to a temperature of from 0-15° C., or not more than 10° C., tosyl chloride is added, then a base is added, for example, potassium t-butoxide. The solution is allowed to come to ambient temperature and stirred for 30-90 minutes. Then diphenylacetonitrile is added. In some embodiments a second polar aprotic solvent, for example DMF, is added prior to the diphenylacetonitrile to enhance solubility. The mixture is stirred and cooled to 0-15° C., or not more than 10° C. Potassium t-butoxide is added, and the reaction mixture is gradually heated to an elevated temperature of from 35-70, 40-60, or about 50° C. for from 2-16, or 2-4 hrs at the elevated temperature. The reaction mixture is cooled to from 0-15, or not more than 10° C., then quenched with dilute HCl, and extracted with an organic solvent, e.g., toluene. The aqueous phase is treated with aq. NaOH at pH≥10 to form the free base and extracted with MTBE, and dried over sodium sulfate, then concentrated. The crude solid product is suspended and or dissolved in one or more solvents, heated, and cooled to provide a needle-like crystalline product levomethadone nitrile.

Preparation of Levomethadone Hydrochloride from Levomethadone Nitrile

In some embodiments, levomethadone nitrile is converted to levomethadone hydrochloride by use of a Grignard addition with ethyl magnesium bromide. In the final step, levomethadone nitrile reacts with Grignard reagent ethyl magnesium bromide to give an imine intermediate which upon acid hydrolysis yields levomethadone hydrochloride. Levomethadone free base is obtained after basification of the reaction mixture with NaOH and extraction with an organic solvent such as MTBE. Treatment of the crude levomethadone base with aqueous HCl produces the levomethadone hydrochloride final product.

In some embodiments, levomethadone nitrile is converted to levomethadone hydrochloride by treating with ethyl magnesium bromide, as shown in FIG. 6. In some embodiments, the ethyl magnesium bromide is made in situ, for example with magnesium shavings and ethyl bromide, or the ethyl magnesium bromide may be purchased as a reagent. In some embodiments, the ethyl magnesium bromide is performed with $CuBr/H^3O+$, by the method of Weiberth et al., J Org Chem 52, 3901 (1987), which is incorporated herein by reference. In one embodiment, the levomethadone nitrile is dissolved in an anhydrous hydrocarbon solvent to form a reaction mixture. In some embodiments, the hydrocarbon solvent is selected from xylene or toluene. Ethyl magnesium bromide in an ether solvent is added slowly under Ar to the reaction mixture and the reaction mixture is warmed to remove the ether solvent and heated for between 0.5-18 h at an elevated temperature between 30-125° C., 50-110°, or 80-100° C. After cooling to ambient temperature and aqueous HCl is added with optional external cooling. After HCl is added, the reaction mixture is heated to facilitate the hydrolysis of the imine intermediate to form levomethadone hydrochloride. After basification with NaOH, levomethadone free base is extracted, dried and treated with an HCl solution to form the levomethadone hydrochloride final product. After removal of water, the crude product is recrystallized from an alcohol solvent, hydrocarbon solvent, and/or a polar aprotic solvent to form crystalline levomethadone hydrochloride. In some embodiments, the product is recrystallized from methanol, ethanol, and/or acetone, or a mixture thereof to produce the product levomethadone hydrochloride.

The process according to FIG. 1C, via steps 1B and 2B, was performed three times to provide three lots of levomethadone hydrochloride from D-alanine. Test results are shown in Table 1.

TABLE 1

Test results from three Levomethadone HCl lots

| Characteristic* | Specification | Lot #1 | Lot #2 | Lot #3 |
|---|---|---|---|---|
| Appearance | White or almost crystalline powder | White, crystalline powder | White, crystalline powder | White, crystalline powder |
| Assay (Potentiometric Titration) | 99.0% to 101.0% (dried basis) | 99.4% | 99.5% | 99.4% |
| Identification A (Specific Optical Rotation) | −125° to −135° (dried substance) | −130° | −130° | −130° |
| Identification B (Melting Point) | 239° C.-242° C. | Not tested | Not tested | Not tested |
| Identification C (IR) | Matches EP reference spectrum reference of methadone hydrochloride | Meets requirements | Meets requirements | Meets requirements |
| Identification D (Chlorides) | Meets EP Requirement | Not tested | Not tested | Not tested |
| Loss on Drying | NMT 0.5% | 0.20% | 0.20% | 0.10% |
| Sulfated Ash | NMT 0.1% | 0.10% | 0.0% | 0.0% |
| Appearance of Solution | Clear (EP 2.2.1) and Colorless (EP 2.2.2, Method II) | Clear and Colorless | Clear and Colorless | Clear and Colorless |
| Acidity and Alkalinity | See the TEST section | Meets requirements | Meets requirements | Meets requirements |
| Related substances by HPLC: Dextromethadone | NMT 0.5% | Not Detected | Not Detected | Not Detected |
| Related substances by HPLC: Any impurities | NMT 0.1% | Not Detected | Not Detected | Not Detected |
| Related substances by HPLC: Total Impurities | NMT 0.5% | Not Detected | Not Detected | Not Detected |
| Residual Solvents | Conforms to USP <467> | Conforms MTBE: 4 ppm Acetone: 107 ppm Methanol: 42 ppm Toluene: 39 ppm | Conforms MTBE: 5 ppm Acetone: 175 ppm Methanol: 26 ppm Toluene: 24 ppm | Conforms MTBE: 2 ppm Acetone: 70 ppm Methanol: 36 ppm Toluene: 24 ppm |
| Heavy Metals | Conforms to USP <232> | Conforms | Conforms | Conforms |
| Heavy Metals: Zinc | Report results | 3 ppm | 5 ppm | 14 ppm |

*per European Pharmacopoeia 8.0, Levomethadone hydrochloride Monograph of 01/2008: 1787 corrected 6.5. pp. 2614-2615.

In some embodiments, the levomethadone hydrochloride is characterized by one or more of chiral HPLC, RP-HPLC, IR, $^{13}$C-NMR, and $^1$H-NMR. In some embodiments, levomethadone hydrochloride is provided comprising not more than 100 ppm, 50 ppm, or 10 ppm of dextromethadone, as detected by the chiral HPLC; and not more than 100 ppm, 50 ppm, or 10 ppm of an impurity selected from diphenylacetonitrile, levomethadone nitrile, isolevomethadone nitrile, and isolevomethadone as detected by reverse phase HPLC.

In some embodiments, a compound according to Formula (I) or pharmaceutically acceptable salt thereof, is provided, wherein the substituents are as provided herein. In some embodiments, an isolated and/or purified compound according to Formula (I) or pharmaceutically acceptable salt thereof, is provided, wherein the substituents are as provided herein. In some embodiments, an isolated and/or purified compound according to formula (I) is provided, wherein Y=—C(O)R$_{14}$; R$_1$, R$_2$, R$_3$, R$_4$, R$_5$, R$_6$, R$_7$, R$_8$, R$_9$, R$_{10}$ are independently H; R$_{11}$ is —CH$_3$, —CH(CH$_3$)$_2$, —CH$_2$CH(CH$_3$)$_2$, —CH(CH$_3$)CH$_2$CH$_3$, -or-CH$_2$Ph; R$_{12}$ and R$_{13}$ are independently C$_{1-6}$ alkyl; R$_{14}$ is alkyl, alkenyl or aryl; n=1; and * is in the R configuration in greater than 99% e.e.

Preparation of Dextromethadone Hydrochloride from L-Alanine

A process for preparation of dextromethadone hydrochloride from L-alanine is shown in FIG. 1B. In some embodiments, as shown in FIG. 1D, a process for preparing dextromethadone hydrochloride is provided comprising converting L-alanine to N,N-dimethyl-L-alanine; reducing the N,N-dimethyl-L-alanine to form N,N-dimethyl-L-alaninol; combining the N,N-dimethyl-L-alaninol with an activating reagent to form an activated intermediate; mixing the activated intermediate and a base with diphenylacetonitrile to provide dextromethadone nitrile; and exposing the dextromethadone nitrile to ethyl magnesium bromide, and hydrochloric acid, to provide dextromethadone hydrochloride.

Figure 1D:
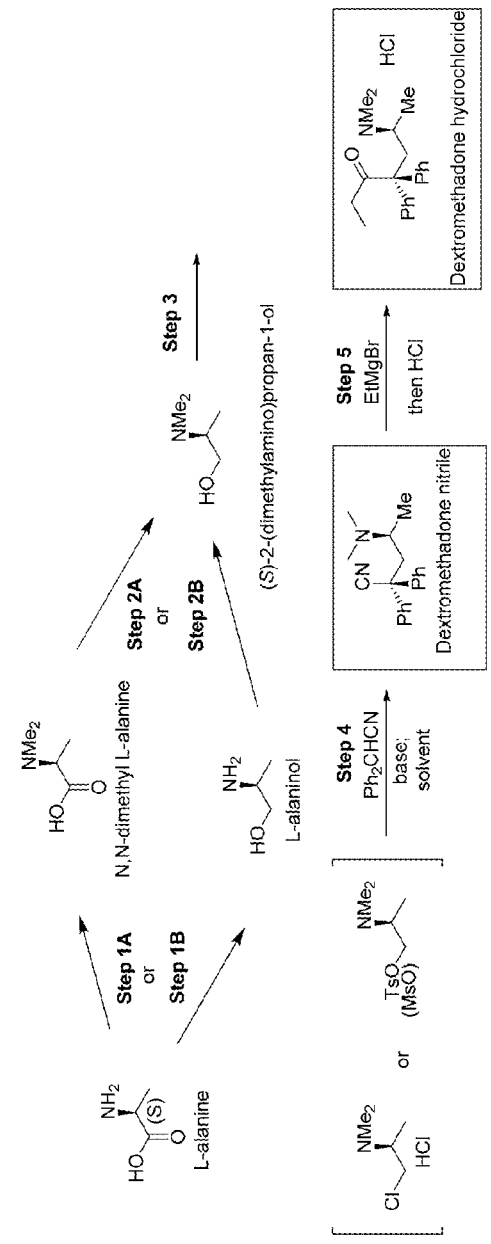
FIG. 1D shows two alternative routes for preparation of dextromethadone hydrochloride from L-alanine with retention of configuration.

In other embodiments, as shown in FIG. 1D, a process for preparing dextromethadone hydrochloride is provided comprising converting L-alanine to L-alaninol; converting the L-alaninol to N,N-dimethyl-L-alaninol; combining the N,N-dimethyl-L-alaninol with an activating reagent to form an activated intermediate; mixing the activated intermediate and a base with diphenylacetonitrile to provide dextromethadone nitrile; and exposing the dextromethadone nitrile to ethyl magnesium bromide, and hydrochloric acid, to provide dextromethadone hydrochloride. A specific embodiment is shown in FIGS. 25A-25C.

In another embodiment, a highly efficient asymmetric synthesis of dextromethadone hydrochloride is provided starting from L-alanine, and resulting in dextromethadone hydrochloride in greater than 95%, 97%, 99% 99.5%, or 99.9% e.e.

In some embodiments, a process is provided for the production of dextromethadone hydrochloride comprising not more than 0.5%, 0.25%, 0.1%, 0.05%, 0.025%, 0.01%. 0.005%, 0.001%, 0.0005%, or 0.0001% of an impurity selected from levomethadone, isolevomethadone, isodextromethadone, dextromethadone nitrile, levomethadone nitrile, isodextromethadone nitrile, isolevomethadone nitrile, diphenylacetonitrile, 2(R)-2-[[(4-methylphenyl)sulphonyl] amino]pentanedioic acid (N-tosyl-L-glutamic acid); a tartaric acid, or a bromocamphor sulfonic acid, such as a 3-bromocamphor-10-sulfonic acid.

In some embodiments, a process is provided for the production of dextromethadone hydrochloride comprising not more than 0.5%, 0.25%, 0.1%, 0.05%, 0.025%, 0.01%. 0.005%, 0.001%, 0.0005%, or 0.0001% of levomethadone or levomethadone hydrochloride.

Synthesis of N,N-Dimethyl-L-Alaninol

In some embodiments, a process for preparing dextromethadone hydrochloride is provided comprising converting L-alanine to N,N-dimethyl-L-alanine, wherein the converting comprises hydrogenating the L-alanine with formaldehyde and/or paraformaldehyde with a catalyst to form N,N-dimethyl-L-alanine.

In some embodiments, a process for preparing dextromethadone hydrochloride is provided comprising reducing the N,N-dimethyl-L-alanine to form N,N-dimethyl-D-alaninol, wherein the reducing comprises exposing the N,N-dimethyl-D-alanine to one or more reducing agents selected from $LiAlH_4$, $BH_3$/THF, $BH_3/Et_2O$, $BH_3/BF_3$ $Et_2O$, $BH_3/Me_2S$, $NaBH_4/I_2$, $BH_4$/cyanuric chloride, $NaBH_3CN/ZnCl_2$, $NaBH_4/ZnCl_2$, $Zn(BH_4)_2$, or $NaBH_4/BF_3.Et_2O$. In a specific aspect, the reducing agent is $LiAlH_4$.

In some embodiments, a process for preparing dextromethadone hydrochloride is provided comprising reducing L-alanine to form L-alaninol, wherein the reducing comprises exposing the L-alanine to one or more reducing agents selected from $LiAlH_4$, $BH_3$/THF, $BH_3/Et_2O$, $BH_3/BF_3$ $Et_2O$, $BH_3/Me_2S$, $NaBH_4/I_2$, $BH_4$/cyanuric chloride, $NaBH_3CN/ZnCl_2$, $NaBH_4/ZnCl_2$, $Zn(BH_4)_2$, or $NaBH_4/BF_3.Et_2O$. In a specific aspect, the reducing agent is $Zn(BH_4)_2$.

In some embodiments, the L-alaninol is dimethylated by any known means to form N,N-dimethyl-D-alaninol. In one embodiment, L-alaninol is treated with formaldehyde and formic acid and heated to provide N,N-dimethyl-L-alaninol. A specific embodiment is shown in FIG. 25A.

Preparation of Dextromethadone Nitrile from N,N-Dimethyl-L-Alaninol Via Activated Intermediate In some embodiments, a process for preparing dextromethadone hydrochloride is provided comprising combining N,N-dimethyl-L-alaninol with an activating reagent to form an activated intermediate, wherein the activating reagent is selected from thionyl chloride, methanesulfonyl chloride, p-toluenesulfonyl chloride, trifluoromethanesulfonyl chloride, methanesulfonic anhydride, trifluoromethanesulfonic anhydride, or p-toluenesulfonic anhydride.

In some embodiments, the activated intermediate is selected from (S)-1-chloro-N,N-dimethylpropan-2-amine HCl, (S)-1-chloro-N,N-dimethylpropan-2-amine, (S)-2-(dimethylamino)propyl 4-methylbenzenesulfonate, or (S)-2-(dimethylamino)propyl methanesulfonate. In a specific aspect, the activated intermediate is (S)-1-tosyl-N,N-dimethylpropan-2-amine HCl. In another aspect, the activated intermediate is isolated before being used in the next step, or is prepared and used in the next step without isolation.

In some embodiments, a process for preparing dextromethadone hydrochloride is provided comprising mixing an activated intermediate and a base with diphenylacetonitrile to provide dextromethadone nitrile, wherein the mixing comprises exposing the activated intermediate to a base and diphenylacetonitrile in a solvent to form the dextromethadone nitrile. One specific embodiment, where the activated intermediate is (S)-1-tosyl-N,N-dimethylpropan-2-amine, is shown in FIG. 25B. In some embodiments, the activated intermediate is mixed with diphenylacetonitrile, then a base is added, selected from the group consisting of sodium hydroxide, potassium hydroxide, potassium t-butoxide, sodium t-butoxide, sodium methoxide, potassium methoxide, sodium ethoxide, potassium ethoxide, sodium isopropoxide, and potassium isopropoxide. In a specific aspect, the base is potassium t-butoxide. In some embodiments, the solvent is selected from dimethylformamide, dimethylacetamide, tetrahydrofuran, dimethyl sulfoxide, N-methyl-2-pyrrolidone, dioxane, water, or a combination thereof. In specific aspects, dextromethadone nitrile is formed in >95%, >97%, >99%, >99.5%, or >99.9% enantiomeric excess (e.e.). In a specific aspect, dextromethadone nitrile is formed in >99% enantiomeric excess (e.e.).

Preparation of Dextromethadone Hydrochloride from Dextromethadone Nitrile

In some embodiments, dextromethadone nitrile is treated with a Grignard reagent such as ethyl magnesium bromide, and hydrochloric acid, to provide dextromethadone hydrochloride, wherein the exposing comprises adding ethyl magnesium bromide to a stirred solution of dextromethadone nitrile in an anhydrous solvent to form a reaction mixture; heating the reaction mixture; cooling the reaction mixture to ambient temperature; adding hydrochloric acid to the reaction mixture with external cooling such that the reaction temperature does not exceed 50° C.; and isolating the levomethadone hydrochloride. In some embodiments, the reaction mixture of dextromethadone nitrile and about 2 equivalents of ethyl magnesium bromide is heated to 100° C. for 1-6 hrs, then cooled prior to treating with HCl. One specific embodiment is shown in FIG. 25C.

In some embodiments, dextromethadone hydrochloride is provided comprising not more than 0.05%(500 ppm), 0.025%(250 ppm), or 0.01%(100 ppm) of an impurity selected from levomethadone hydrochloride, levomethadone, isolevomethadone, isolevomethadone hydrochloride, isosextromethadone, isodextromethadone hydrochloride, dextromethadone nitrile, levomethadone nitrile, isodextromethadone nitrile, isolevomethadone nitrile, diphenylacetonitrile, 2R)-2-[[(4-methylphenyl)sulphonyl] amino]pentanedioic acid (N-tosyl-L-glutamic acid); a tartaric acid, or a bromocamphor sulfonic acid, such as a 3-bromocamphor-10-sulfonic acid.

In some embodiments, a process for preparing dextromethadone hydrochloride is provided herein, wherein the dextromethadone hydrochloride comprises not more than 100 ppm of an impurity selected from the group consisting of levomethadone, diphenylacetonitrile, dextromethadone nitrile, isodextromethadone nitrile, and isodextromethadone.

In some embodiments, a pharmaceutical composition is provided comprising an effective amount of dextromethadone hydrochloride having not more than 100 ppm of an impurity selected from the group consisting of levomethadone, diphenylacetonitrile, dextromethadone nitrile, isodextromethadone nitrile, and isodextromethadone; and a pharmaceutically-acceptable carrier. In one aspect, a pharmaceutical composition is provided comprising an effective amount of dextromethadone hydrochloride having not more than 50 ppm of levomethadone. In another aspect, a pharmaceutical composition is provided comprising an effective amount of dextromethadone hydrochloride having not more than 25 ppm of levomethadone. In another aspect, a pharmaceutical composition is provided comprising an effective amount of dextromethadone hydrochloride having not more than 10 ppm of levomethadone.

In some embodiments, a method for preparing a compound according to Formula (I) or pharmaceutically acceptable salt thereof, is provided,

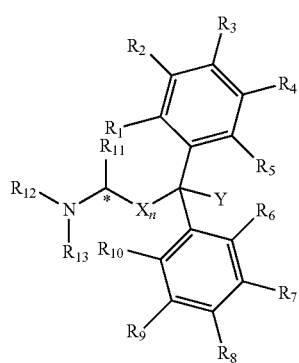

(I)

wherein $R_1$, $R_2$, $R_3$, $R_4$, $R_5$, $R_6$, $R_7$, $R_8$, $R_9$, $R_{10}$ are independently H, amino, C1-6 alkyl, alkenyl, alkynyl, halo, hydroxyl, carbocyclic, heterocyclic, or aryl;
$R_{11}$ is H, acyl, amino, amido, azido, carboxyl, alkyl, aryl, aralkyl, halo, guanidinyl, oxo, sulfanyl, sulfenyl, sulfonyl, heterocyclyl, heteroaryl, or hydroxyl;
$R_{12}$, $R_{13}$ are independently H, acyl, alkyl, alkyenyl, alkynyl, aralkyl, aryl, carboxyl, cycloalkyl, heterocyclic, or other amino (in the case of hydrazide) or $R_{12}$ and $R_{13}$ together with the nitrogen atom to which they are attached, form a ring having 4-8 atoms.
X is $(CH_2)_n$, where n=1-6;
Y is —CN or —C(O)$R_{14}$;
$R_{14}$ is alkyl, alkanyl, alkynyl, cycloalkyl, heterocyclyl, aryl, heteroaryl, alkoxy, aryloxy, aralkyl, or amino; and
*is a stereocenter selected from R or S configuration.

In some embodiments, a method for preparing a compound according to formula (I) is provided, comprising converting a chiral amino acid selected from a D-amino acid or an L-amino acid, to a dialkyl amino acid; treating the dialkyl amino acid with a reducing agent to convert the carboxyl group to a hydroxyl group and form a dialkyl aminoalcohol; converting the dialkyl aminoalcohol hydroxyl group to a halo group or a sulfonyl group to form an activated intermediate; mixing the activated intermediate with a base and a diarylacetonitrile to provide a nitrile intermediate of formula (I) wherein Y is —CN; and exposing the nitrile intermediate to a Grignard reagent and an acid to form the compound of formula (I) wherein Y is —C(O)$R_{14}$.

In some embodiments, the alkyl groups of the dialkyl amino acid are selected from $C_{1-6}$ alkyl groups. In some embodiments, the Grignard reagent is selected from RMgX where R is $C_{1-6}$ alkyl and X is I, Br, or Cl. In some embodiments, the Grignard reagent is ethyl magnesium bromide. In some embodiments, the chiral amino acid is a D-amino acid. In some embodiments, the reducing agent is selected from one or more of $LiAlH_4$, $BH_3$/THF, $BH_3$/$Et_2O$, $BH_3$/$BF_3\cdot Et_2O$, $BH_3$/$Me_2S$, $NaBH_4$/$I_2$, $BH_4$/cyanuric chloride, $NaBH_3CN$/$ZnCl_2$, or $NaBH_4$/$BF_3\cdot Et_2O$. In some embodiments, the activated intermediate is formed by exposing the dialkylamino alcohol to thionyl chloride and the halo group is a chloro group. In some embodiments, the sulfonyl group is selected from a mesyl group or a tosyl group.

In some embodiments, an isolated compound is provided according to Formula (I), or pharmaceutically acceptable salt thereof, wherein the stereocenter *is an R configuration, in greater than 90%, 95%, 97%, 99%, 99.5%, or 99.9% e.e compared to the S isomer.

In some embodiments, a compound is provided according to Formula (I), or pharmaceutically acceptable salt thereof, wherein the stereocenter *is an S configuration in greater than 90%, 95%, 97%, 99%, 99.5%, or 99.9% e.e compared to the *R isomer.

In some embodiments, a method for preparing a compound according to Formula (I), or pharmaceutically acceptable salt thereof, is provided comprising isolating or purifying the compound according to Formula (I), or pharmaceutically acceptable salt thereof. In some embodiments, the isolating and or purifying comprises recrystallization, or chromatographic purification of the compound according to Formula (I), or pharmaceutically acceptable salts thereof. In some embodiments, the compound or salt is recrystallized from an alcohol solvent, hydrocarbon solvent, and/or a polar aprotic solvent to form crystalline compound of Formula (I), or pharmaceutically acceptable salt thereof.

In some embodiments, $R_1$, $R_2$, $R_3$, $R_4$, $R_5$, $R_6$, $R_7$, $R_8$, $R_9$, $R_{10}$ are independently H, $C_{1-6}$ alkyl, or halo. In some embodiments, $R_1$, $R_2$, $R_3$, $R_4$, $R_5$, $R_6$, $R_7$, $R_8$, $R_9$, $R_{10}$ are independently H and Y is —C(O)$R_{14}$.

In some embodiments, $R_{11}$ is selected from H, —$CH_3$, —$CH(CH_3)_2$, —$CH_2CH(CH_3)_2$, —$CH(CH_3)CH_2CH_3$, —$CH_2$-pyrrolidinyl, —$CH_2CH_2SCH_3$, —$CH_2Ph$, —$CH_2$-indol-3-yl, —$CH_2OH$, —$CH(OH)CH_3$, —$CH_2SH$, $CH_2Ph$-OH, —$CH_2C(\!\!=\!\!O)NH_2$, —$CH_2CH_2C(\!\!=\!\!O)NH_2$, —$CH_2CO_2H$, —$CH_2CH_2CO_2H$, —$(CH_2)_4NH_2$, —$(CH_2)_3NHC(\!\!=\!\!NH_2)NH_2$, or —$CH_2$-imidazol-4-yl.

In some embodiments, n=1, 2, 3, 4, 5 or 6. In specific embodiments, n=1.

In some embodiments, $R_{12}$ and $R_{13}$ are independently C1-6 alkyl. In specific embodiments, $R_{12}$ and $R_{13}$ are independently methyl, ethyl, n-propyl, i-propyl, n-butyl, i-butyl, sec-butyl, or t-butyl. In some embodiments, $R_{12}$ and $R_{13}$ are independently methyl or ethyl. In some embodiments, $R_{12}$ and $R_{13}$ are independently methyl.

In some embodiments, $R_{11}$, $R_{12}$, $R_{13}$ are each independently methyl.

In some embodiments, Y is —C(O)R14 where $R_{14}$ is $C_{1-6}$ alkyl. In some embodiments, $R_{14}$ is —$CH_3$, —$CH_2CH_3$, $CH(CH_3)_2$, —$CH_2CH(CH_3)_2$, —$CH(CH_3)CH_2CH_3$, —$C(CH_3)_3$, or —$(CH_2)_mCH_3$ where m=1, 2, 3, 4, 5 or 6. In a specific embodiment, $R_{14}$ is —$CH_2CH_3$, In some embodiments, a compound according to formula (I) or pharmaceutically acceptable salt thereof, is provided wherein $R_1$, $R_2$, $R_3$, $R_4$, $R_5$, $R_6$, $R_7$, $R_8$, $R_9$, $R_{10}$ are independently H, $R_{11}$ is Me, $R_{12}$ and $R_{13}$ are independently Me, $R_{14}$ is Et, and n=11, and * is in the R configuration in greater than 97%, 99%, 99.5% or 99.9% e.e.

In other embodiments, a compound according to formula (I) or pharmaceutically acceptable salt thereof, is provided wherein $R_1$, $R_2$, $R_3$, $R_4$, $R_5$, $R_6$, $R_7$, $R_8$, $R_9$, $R_{10}$ are independently H, $R_{11}$ is Me, $R_{12}$ and $R_{13}$ are independently Me, $R_{14}$ is Et, and n=1, and * is in the S configuration in greater than 97%, 99%, 99.5% or 99.9% e.e.

In some embodiments, a compound is provided according to Formula (I) or pharmaceutically acceptable salt thereof, that is not methadone. In some embodiments, a compound is provided according to Formula (I) that is not p-hydroxy methadone. In some embodiments, a compound is provided according to Formula (I) that is not levomethadone.

In some embodiments, a compound is provided according to formula (I) that is an isolated compound.

In some embodiments, a compound is provided according to formula (I) that is a purified compound.

In some embodiments, an intermediate or final compound is provided comprising one or more "protecting groups" (-PG), as described in Greene and Wuts, "Protective Groups in Organic Synthesis", $2^{nd}$ Ed., John Wiley & Sons, Inc., New York, 1991, which is incorporated herein by reference.

As used herein, the term "chiral chromatography" or "chiral HPLC" refers to a chromatographic technique employing a chiral stationary phase (CSP). For example, the chiral stationary phase may be selected from Pirkle-type CSP, a cyclodextrin-type CSP, a protein-bound CSP, or a cellulose-derived CSP. See Porter, Pure & Appl Chem 63(8):1119-1122, 1991, which is incorporated herein by reference. In some embodiments, the chiral HPLC is performed with a cellulose-derived CSP. In some embodiments, the cellulose derived CSP is a cellulose-based HPLC column.

In some embodiments, an isolated compound according to Formula (I) is provided by variations of the methods provided herein, wherein the substituents are as defined herein, wherein the stereocenter* is in the R or S configuration; and wherein the compound according to Formula (I) is an isolated compound in greater than 90%, 97%, 95%, 99%, 99.5%, or 99.9% enantiomeric excess, as determined by chiral HPLC.

In some embodiments, methods are provided for preparation of a compound according to Formula (I), or pharmaceutically acceptable salt thereof, wherein the substituents are as defined herein, wherein the stereocenter* is in the R or S configuration; and wherein the compound according to Formula (I) is an isolated compound in greater than 90%, 97%, 95%, 99%, 99.5%, or 99.9% enantiomeric excess, as determined by chiral HPLC.

In some embodiments, pharmaceutical compositions are provided comprising a compound according to Formula (I), or pharmaceutically acceptable salt thereof, wherein the substituents are as defined herein, wherein the stereocenter* is in the R or S configuration; and wherein the compound according to Formula (I) is an isolated compound in greater than 90%, 97%, 95%, 99%, 99.5%, or 99.9% enantiomeric excess, as determined by chiral HPLC, and a pharmaceutically acceptable carrier.

In some embodiments, a method of treating chronic pain, or of opioid detoxification, is provided, comprising administering a pharmaceutical composition to a subject in need thereof, wherein the composition comprises (a) a compound according to Formula (I), or pharmaceutically acceptable salt thereof, wherein the substituents are as defined herein, wherein the stereocenter* is in the R or S configuration; and wherein the compound according to Formula (I) or pharmaceutically acceptable salt thereof, is an isolated compound in greater than 90%, 97%, 95%, 99%, 99.5%, or 99.9% enantiomeric excess, as determined by chiral HPLC; and (b) a pharmaceutically acceptable carrier.

Compositions

In some embodiments the disclosure provides a pharmaceutical composition comprising a pharmaceutically effective amount of levomethadone hydrochloride having not more than 0.05%(500 ppm), 0.025%(250 ppm), 0.01%(100 ppm), 0.005%(50 ppm), 0.0025%(25 ppm), or 0.001%(10 ppm), of an impurity selected from the group consisting of dextromethadone, diphenylacetonitrile, levomethadone nitrile, isolevomethadone nitrile, and isolevomethadone.

In some embodiments the disclosure provides a pharmaceutical composition comprising a pharmaceutically effective amount of dextromethadone hydrochloride having not more than 0.05%(500 ppm), 0.025%(250 ppm), 0.01%(100 ppm), 0.005%(50 ppm), 0.0025%(25 ppm), or 0.001%(10 ppm), of an impurity selected from the group consisting of levomethadone, diphenylacetonitrile, dextromethadone nitrile, isodextromethadone nitrile, and isodextromethadone.

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier.

Pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose, microcrystalline ecellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) lubricants, such as magnesium stearate, calcium stearate, zinc stearate, sorbitan monostearate, sucrose monopalmitate, glycerol dibehenate, and stearic acid; (16) alginic acid; (17) pyrogen-free sterile water; (18) isotonic saline; (19) Ringer's solution; (20) ethyl alcohol; (21) phosphate buffer solutions; (22) polymers and time release agents; (23) bioavailability enhancers and bioavailability controllers/inhibitors; and (23) other non-toxic compatible substances employed in pharmaceutical formulations.

Other non-toxic compatible substances include optional flavorings and/or sweeteners.

In another embodiment, compositions of the disclosure can optionally further comprise one or more flavoring agents. The optional flavoring agent is added to increase patient acceptability and compliance with the recommended dosing schedule. The flavoring agents that may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, *eucalyptus* oil, thyme oil, cedar leaf oil, oil of nutmeg, allspice, oil of sage, mace, oil of bitter almonds, and *cassia* oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. In a specific aspect, the flavoring is selected from a cherry or orange flavoring.

Various sweeteners can be optionally used in the tablet, liquid, capsule, lozenge or troche formulations of the disclosure. Examples of carbohydrates and sweeteners include monosaccharides such as glucose and fructose, disaccharides such as maltose, sucrose, other ordinary sugars, sugar alcohols such as xylitol, sorbitol, glycerin and erythritol, polysaccharides such as dextrin and cyclodextrin, and oligosaccharides such as fructo-oligosaccharide, galacto-oligosaccharide and lacto-sucrose. Other sweeteners include natural sweeteners such as thaumatin, stevia extract, Luo Han Guo (Lo Han fruit), rebaudioside A, glycyrrhizinic acid, etc. and synthetic sweeteners such as saccharin, aspartame, azesulfame potassium, etc.

Optionally various FD& C dyes or opacifiers can be employed in the compositions. In various aspects, the FD&C dye is selected from one or more of FD&C Red No. 3, Red No. 40, Red No. 33, Yellow No. 6, Yellow No. 6 lake, Yellow No. 5 lake, Yellow No. 5, Green No. 3, Blue No. 1 and Blue No. 2. In one aspect, the opacifier is titanium dioxide. In one specific aspect, a composition is provided comprising FD&C Red No. 40 and FD&C Red No. 33. In another specific aspect, a composition according to the disclosure is provided comprising FD&C Yellow No. 6, Yellow No. 6 lake, and Yellow No. 5 lake.

The compositions may be formulated for any route of administration, in particular for oral, rectal, transdermal, subcutaneous, intravenous, intramuscular or intranasal administration.

The compositions may be formulated in any conventional form, for example, as oral tablets, dispersible tablets, tablets for oral suspension, disket dispersible tablets, capsules, caplets, solution, oral solution, oral concentrate, suspensions, dispersions, troche, syrups, sprays, gels, suppositories, patches and emulsions. In specific embodiments, the composition is in the form of oral tablet, oral solution, oral concentrate, or tablet for oral suspension.

As is well known in the medical arts, dosages for any one subject may depend upon many factors, including the patient's size, body surface area, age, the particular compound to be administered, sex, time and route of administration, general health, and interaction with other drugs being concurrently administered. Depending on the target sought to be altered by treatment, pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. In some embodiments, dosage forms for transmucosal administration include, but are not limited to fast melt, buccal or sublingual dosage forms.

Pharmaceutical compositions suitable for use in the present application include compositions wherein the active ingredients (e.g., levomethadone, levomethadone hydrochloride, levomethadone hydrobromide, a compound of formula I, and combinations thereof), comprising not more than 500 ppm, 100 ppm, 50 ppm, 10 ppm, or 1 ppm of an impurity selected from the group consisting of dextromethadone, diphenylacetonitrile, levomethadone nitrile, isolevomethadone nitrile, and isolevomethadone, is contained in an effective amount to achieve the intended purpose. For example, in a preferred embodiment, an effective amount of a pharmaceutical composition comprises an amount of levomethadone hydrochloride comprising not more than 500 ppm, 100 ppm, 50 ppm, 10 ppm, or 1 ppm of an impurity selected from the group consisting of dextromethadone, diphenylacetonitrile, levomethadone nitrile, isolevomethadone nitrile, and isolevomethadone. Determination of effective amounts is well within the capability of those skilled in the art, especially in light of the disclosure provided herein.

Pharmaceutical compositions suitable for use in the present application include compositions wherein the active ingredients (e.g., dextromethadone, dextromethadone hydrochloride, dextromethadone hydrobromide, a compound of formula I, and combinations thereof), comprising not more than 500 ppm, 100 ppm, 50 ppm, 10 ppm, or 1 ppm of an impurity selected from the group consisting of levomethadone, diphenylacetonitrile, dextromethadone nitrile, isodextromethadone nitrile, and isodextromethadone, is contained in an effective amount to achieve the intended purpose. For example, in a preferred embodiment, an effective amount of a pharmaceutical composition comprises an amount of dextromethadone hydrochloride comprising not more than 500 ppm, 100 ppm, 50 ppm, 10 ppm, or 1 ppm of an impurity selected from the group consisting of levomethadone, diphenylacetonitrile, dextromethadone nitrile, isodextromethadone nitrile, and isodextromethadone.

In one embodiment, a levomethadone hydrochloride composition is provided that is an oral concentrate comprising an effective amount of levomethadone hydrochloride, and citric acid, methylparaben, poloxamer 407, propylene glycol, propylparaben, purified water, sodium citrate dihydrate, and sucrose. In some aspects, the composition further comprises cherry flavor and one or more red dyes. In a specific embodiment, a composition is provided that is an oral concentrate comprising 10 mg/mL levomethadone hydrochloride, and citric acid, methylparaben, poloxamer 407, propylene glycol, propylparaben, purified water, sodium citrate dihydrate, and sucrose. In some aspects, the composition further comprises cherry flavor and one or more red dyes.

In one embodiment, a levomethadone hydrochloride composition is provided that is an oral concentrate comprising an effective amount of levomethadone hydrochloride, citric acid, purified water, and sodium benzoate. In a specific embodiment, a composition is provided that is an oral concentrate comprising 10 mg/mL levomethadone hydrochloride, citric acid, purified water, and sodium benzoate.

In one embodiment, a levomethadone hydrochloride composition is provided that is an oral tablet comprising an effective amount of methadone hydrochloride, and magnesium stearate, microcrystalline cellulose, and starch. In specific embodiments, compositions are provided comprising 5 mg or 10 mg levomethadone hydrochloride, and magnesium stearate, microcrystalline cellulose, and starch.

In one embodiment, a levomethadone hydrochloride composition is provided that is a dispersible tablet for oral suspension comprising an effective amount of levomethadone hydrochloride and dibasic calcium phosphate, microcrystalline cellulose, magnesium stearate, colloidal silicon dioxide, pregelatinized starch, and stearic acid. In a specific aspect, a levomethadone hydrochloride composition is provided that is a dispersible tablet comprising 40 mg of levomethadone hydrochloride and dibasic calcium phosphate, microcrystalline cellulose, magnesium stearate, colloidal silicon dioxide, pregelatinized starch, and stearic acid.

In one embodiment, a levomethadone hydrochloride composition is provided that is a dispersible tablet for oral suspension comprising an effective amount of levomethadone hydrochloride and colloidal silicon dioxide, monobasic potassium phosphate, magnesium stearate, microcrystalline cellulose, pregelatinized starch, and stearic acid. In some aspects, the composition further comprises orange flavor and yellow dye. In a specific aspect, a dispersible tablet composition is provided comprising 40 mg levomethadone hydrochloride, colloidal silicon dioxide, monobasic potassium phosphate, magnesium stearate, microcrystalline cellulose, pregelatinized starch, stearic acid, FD&C Yellow No. 6, Yellow No. 6 lake, and Yellow No. 5 lake, and orange flavor.

In one embodiment, composition is provided that is a levomethadone oral solution comprising an effective amount of levomethadone hydrochloride, alcohol, benzoic acid, citric acid, flavoring, glycerin, sorbitol, and water. In some embodiments, the composition further comprises flavoring (lemon) and coloring FD&C Red No. 40 and FD&C Yellow No. 6, and either 1 mg/mL, or 2 mg/mL levomethadone hydrochloride.

In one embodiment, a levomethadone hydrochloride composition is provided that is an intravenous composition comprising an effective amount of levomethadone hydrochloride and chlorobutanol, and sodium chloride in sterile water. In specific embodiments a composition is provided comprising levomethadone hydrochloride at a concentration of 10 mg/mL with chlorobutanol preservative 0.5%, in sterile saline.

In some specific embodiments, an effective amount of levomethadone hydrochloride is selected from 2.5 mg, 5 mg, 10 mg, 20 mg, 30 mg, or 40 mg.

In one embodiment, a dextromethadone hydrochloride composition is provided that is an oral concentrate comprising an effective amount of dextromethadone hydrochloride, citric acid, purified water, and sodium benzoate. In a specific embodiment, a composition is provided that is an oral concentrate comprising 10 mg/mL dextromethadone hydrochloride, citric acid, purified water, and sodium benzoate.

In one embodiment, a dextromethadone hydrochloride composition is provided that is an oral tablet comprising an effective amount of dextromethadone hydrochloride, and magnesium stearate, microcrystalline cellulose, and starch. In specific embodiments, compositions are provided comprising 5 mg or 10 mg dextromethadone hydrochloride, and magnesium stearate, microcrystalline cellulose, and starch.

In one embodiment, a dextromethadone hydrochloride composition is provided that is a dispersible tablet for oral suspension comprising an effective amount of dextromethadone hydrochloride and dibasic calcium phosphate, microcrystalline cellulose, magnesium stearate, colloidal silicon dioxide, pregelatinized starch, and stearic acid. In a specific aspect, a dextromethadone hydrochloride composition is provided that is a dispersible tablet comprising 40 mg of dextromethadone hydrochloride and dibasic calcium phosphate, microcrystalline cellulose, magnesium stearate, colloidal silicon dioxide, pregelatinized starch, and stearic acid.

In one embodiment, a dextromethadone hydrochloride composition is provided that is a dispersible tablet for oral suspension comprising an effective amount of dextromethadone hydrochloride and colloidal silicon dioxide, monobasic potassium phosphate, magnesium stearate, microcrystalline cellulose, pregelatinized starch, and stearic acid. In some aspects, the composition further comprises orange flavor and yellow dye. In a specific aspect, a dispersible tablet composition is provided comprising 40 mg dextromethadone hydrochloride, colloidal silicon dioxide, monobasic potassium phosphate, magnesium stearate, microcrystalline cellulose, pregelatinized starch, stearic acid, FD&C Yellow No. 6, Yellow No. 6 lake, and Yellow No. 5 lake, and orange flavor.

In one embodiment, composition is provided that is a dextromethadone oral solution comprising an effective amount of dextromethadone hydrochloride, alcohol, benzoic acid, citric acid, flavoring, glycerin, sorbitol, and water. In some embodiments, the composition further comprises flavoring (lemon) and coloring FD&C Red No. 40 and FD&C Yellow No. 6, and either 1 mg/mL, or 2 mg/mL dextromethadone hydrochloride.

In one embodiment, a levomethadone hydrochloride composition is provided that is an intravenous composition comprising an effective amount of dextromethadone hydrochloride and chlorobutanol, and sodium chloride in sterile water. In specific embodiments a composition is provided comprising dextromethadone hydrochloride at a concentration of 10 mg/mL with chlorobutanol preservative 0.5%, in sterile saline.

In some specific embodiments, an effective amount of dextromethadone hydrochloride is selected from 2.5 mg, 5 mg, 10 mg, 20 mg, 30 mg, or 40 mg.

Administration

In some embodiments the disclosure provides a method of treating a subject in need thereof, comprising administering a composition comprising an effective amount of levomethadone hydrochloride having not more than 500 ppm, 100 ppm, 50 ppm, or 10 ppm of an impurity selected from the group consisting of dextromethadone, diphenylacetonitrile, levomethadone nitrile, isolevomethadone nitrile, and isolevomethadone.

Indications for levomethadone hydrochloride compositions provided herein may be selected from management of chronic malignant and non-malignant pain, management of pain severe enough to require daily, around-the-clock, long-term opioid treatment; detoxification treatment of opiate addiction (heroin or other morphine-like drugs); maintenance therapy for opiate addiction; and to facilitate weaning from opiate medications after extended periods in the ICU, on the ward, or as an outpatient. In some embodiments, compositions are provided for short term or long term administration to a subject in need thereof for treatment of pain and/or addiction.

In some embodiments, an effective amount of levomethadone hydrochloride is selected from 0.01-500 mg, 0.05-300 mg, 0.1-250 mg, 1-100 mg, or 2-80 mg per dose. In some specific embodiments, the effective amount is selected from 1 mg, 1.5 mg, 2.5 mg, 5 mg, 10 mg, 20 mg, 30 mg, 40 mg, 50 mg, 60 mg, 70 mg, 80 mg, 90 mg, 100 mg, 125 mg, 150 mg, 175 mg, 200 mg, 225 mg or 250 mg per dose. In some embodiments, the levomethadone hydrochloride is present in 0.1, 0.25, 0.5, 1, 1.5, 2, 2.5, 3, 4, 5, 10, 15, 20, 30, 40, or 50 mg/mL in the composition. In some specific embodiments, the effective amount of the levomethadone hydrochloride is present at a concentration selected from 5 mg/mL, 5 mg/5 mL, or 2.5 mg/5 mL, in the composition.

In some embodiments, the levomethadone hydrochloride composition is administered one per day (q.d.), twice per day (b.i.d.), three times per day (t.i.d.), four times per day (q.i.d.), or more. In some embodiments, the composition is not for administration in an as needed basis.

In some embodiments, methods for treating a subject in need thereof are provided comprising administering a composition comprising an effective amount of dextromethadone hydrochloride, wherein the subject is suffering from a disease or disorder affecting an NMDA receptor. In some embodiments, methods are provided for treating anxiety disorders, Alzheimer's disease, chronic pain, dementia, depression, neuropathic pain, anti-NMDA receptor encephalitis, opioid analgesic tolerance, schizophrenia, stroke, and traumatic brain injury, comprising administering a composition comprising an effective amount of a dextromethadone hydrochloride having not more than 100 ppm, not more than 50 ppm or not more than 10 ppm levomethadone hydrochloride. In some embodiments, the effective amount is selected from an amount of from 0.5 mg to 500 mg, 1.0 mg to 250 mg, or 2 mg to 50 mg dextromethadone hydrochloride having not more than 100 ppm, not more than 50 ppm or not more than 10 ppm levomethadone hydrochloride.

In some specific embodiments, the effective amount of dextromethadone hydrochloride is selected from 1 mg, 1.5 mg, 2.5 mg, 5 mg, 10 mg, 20 mg, 30 mg, 40 mg, 50 mg, 60 mg, 70 mg, 80 mg, 90 mg, 100 mg, 125 mg, 150 mg, 175 mg, 200 mg, 225 mg or 250 mg per dose. In some embodiments, the dextromethadone hydrochloride is present in 0.1, 0.25, 0.5, 1, 1.5, 2, 2.5, 3, 4, 5, 10, 15, 20, 30, 40, or 50 mg/mL in the composition. In some specific embodiments, the effective amount of the dextromethadone hydrochloride is present at a concentration selected from 5 mg/mL, 5 mg/5 mL, or 2.5 mg/5 mL, in the composition.

In some embodiments, the dextromethadone hydrochloride composition is administered one per day (q.d.), twice per day (b.i.d.), three times per day (t.i.d.), four times per day (q.i.d.), or more. In some embodiments, the composition is not for administration in an as needed basis.

EXAMPLES

In the examples below, temperatures are provided in degrees Celsius and all parts and percentages are by weight, unless otherwise specified. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from commercial suppliers, or may be purified using standard methods known to those skilled in the art, unless otherwise indicated.

The compound structures in the examples below were confirmed by one or more of the following methods: proton magnetic resonance spectroscopy, mass spectroscopy, and melting point. Proton magnetic resonance ($^1$H NMR) spectra were determined using an NMR spectrometer operating at 300 MHz field strength. Chemical shifts are reported in the form of delta (δ) values given in parts per million (ppm) relative to an internal standard, such as tetramethylsilane (TMS). Alternatively, $^1$H NMR spectra were referenced to signals from residual protons in deuterated solvents as follows: CDCl$_3$=7.25 ppm; DMSO-d$_6$=2.49 ppm; CD$_3$OD=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data are obtained using a mass spectrometer with MALDI-TOF, APCI or ESI ionization.

Example 1. A. N,N-dimethyl D-alanine (B)

Step 1: Dimethylation of D-alanine (A) by hydrogenation with formaldehyde in the presence of Pd/C to form N,N-dimethyl D-alanine (B).

This step was carried out by following literature procedures with modifications. See WO 2012/162635; and Paterson et al., Org Lett 2013, 15, 3118-3121; each of which is incorporated by reference.

To a solution of D-alanine (A) (50.0 g, 561 mmol) in water (800 mL) was added formaldehyde (37%, 125 mL, 1,680 mmol) and Pd/C (10% Pd, 20 g). After the flask was purged with Ar for 10 min and with H$_2$ three times, the reaction mixture was stirred at 50° C. under H$_2$ (35 psi) for 20 hrs. The reaction mixture was then heated to reflux for 1 h and filtered while hot through a short pad of celite. The filtrate was concentrated under reduced pressure. More water (200 mL each time, 3 times) was added and the reaction concentrated in order to remove the unreacted formaldehyde. Residual water was removed azeotropically with toluene (3×100 mL). $^1$H-NMR analysis revealed complete consumption of the starting material and clean and essentially quantitative production of the N,N-dimethylated product. The crude product was recrystallized with hot EtOH/acetone (50 ml/250 mL) at 55-60° C. to give 41.36 g (63.0%) product as a white solid; another crop (11.38 g, 17.3%) was obtained after the mother liquor was concentrated and the residual recrystallized from the same solvent system; further purification of the remaining product in the mother liquor was not pursued and the material was saved for future use. $^1$H NMR (300 MHz, MeOH-d$_4$) δ 3.65 (q, J=7.1 Hz, 1H), 2.86 (s, 6H), 1.51 (d, J=7.1 Hz, 3H) ppm, as shown in FIG. 7. $^{13}$C NMR (75 MHz, MeOH-d$_4$) δ 172.1, 66.0, 40.1, 11.6 ppm as shown in FIG. 8.

Example 1. B. N,N-dimethyl D-alanine (B)

A larger scale dimethylation was carried out with 100 g D-Ala in 500 mL water with 250 mL formaldehyde, 30 g Pd/C, and 40 psi H$_2$ pressure, and worked up in accordance with Example 1A. Product was recrystallized from 100 mL/500 mL (EtOH:Acetone) to yield 110.5 g N,N-dimethyl D-alanine (B) (85% yield). Product was characterized by $^1$H-NMR as in example 1A.

Example 2. (R)-2-(dimethylamino)propan-1-ol (C)

Step 2: Reduction of N,N-dimethyl D-alanine (B) with lithium aluminum hydride to form (R)-2-(dimethylamino)propan-1-ol (C).

To a stirred solution of N,N-dimethyl D-alanine (B) (2.34 g, 20 mmol) prepared in Step 1 in THF (30 mL) was added LiAlH$_4$ (1.14 g, 30 mmol) in portions at 0° C. and the resulting reaction mixture heated to reflux for 16 h. After cooling to rt, the reaction was carefully quenched with 10 mL sat. NaHCO$_3$ and stirred for 10 min to generate a thick suspension. DCM (50 mL) was then added and the organic layer separated by decantation. To the remaining pasty residual were added DCM (50 mL) and anhydrous Na$_2$SO$_4$ (about 10 g) and mixture vigorously stirred. The DCM layer was then separated. The residual was stirred with another two portions of DCM (50 mL each). The combined DCM layer was dried over $Na_2SO_4$ and concentrated at 35° C. under reduced pressure to give 1.40 g of crude (R)-2-(dimethylamino)propan-1-ol (C) as a volatile oil (yield: 68%) which was used directly in the next step. $^1H$ NMR (300 MHz, $CDCl_3$) δ 3.43 (dd, J=5.0 and 10.5 Hz, 1H), 3.30 (t, q J=10.2 Hz, 1H), 2.79 (m, 1H), 2.25 (s, 6H), 0.87 (d, J=6.6 Hz, 3H) ppm, shown in FIGS. 9 and 10.

Example 3. (R)-4-(dimethylamino)-2,2-diphenyl-pentanenitrile. Step 3: Synthesis of levomethadone nitrile (E) from (R)-2-(dimethylamino)propan-1-ol (C) and diphenylacetonitrile To a solution of the crude amino alcohol C (550 mg, 5.33 mmol) prepared in Step 2 in chloroform (5 mL) was carefully added a solution of 1.0 mL $SOCl_2$ in $CHCl_3$ (5 mL) at 0° C. The reaction mixture was stirred at rt for 10 min and then heated to reflux for 1 h. After cooling to rt, the solvent and volatiles were removed under vacuum to give 781 mg of crude product D, (R)-1-chloro-N,N-dimethylpropan-2-amine HCl, as a solid product (yield: 93%) which was used directly in the following step.

To a stirred solution of the above (R)-1-chloro-N,N-dimethylpropan-2-amine HCl, intermediate D, in DMF (5.0 mL) was added KOtBu (617 mg, 5.5 mmol) under Ar. The resulting mixture was stirred at rt for 10 min. In a separate flask containing diphenylacetonitrile, $Ph_2CHCN$, (773 mg, 4.0 mmol) in DMF (5 mL) was added KOtBu (494 mg, 4.4 mmol) and the reaction mixture was stirred under Ar at rt for 30 min to generate a reddish yellow solution, which was transferred via cannula to the first flask. The resulting reaction mixture was stirred at rt for 150 min and at 45° C. for 15 h. After cooling to rt, the reaction mixture was poured into water (40 mL) and extracted with EtOAc (25 mL×2). The combined organic extracts were washed with water and brine, and dried over $Na_2SO_4$. Removal of solvent gave 1.11 g crude product. $^1H$ NMR analysis revealed that the crude product mixture consists of diphenylacetonitrile, levomethadone nitrile (E), its regio-isomer i.e., 2,2-diphenyl-3-methyl-4-dimethylaminobutyronitrile (stereochemistry un-assigned) in a ratio of 9%:67%:24%, corresponding to a ratio of 74%:26% between levomethadone nitrile (E) and its regio-isomer.

Recrystallization from heptane (10 mL) gave 824 mg of levomethadone nitrile ((R)-4-(dimethylamino)-2,2-diphenylpentanenitrile) (E) which was 89% pure, with impurities being small amounts of diphenylacetonitrile and the regio-isomer of E as revealed by $^1H$ NMR. Pure samples of levomethadone nitrile (E) were obtained by further recrystallization from the same solvent.

For levomethadone nitrile, intermediate E: $^1H$ NMR (300 MHz, $CDCl_3$) δ 7.28-7.41 (m, 10H), 2.69 (dd, J=6.5 and 13.6 Hz, 1H), 2.54 (m. 1H), 2.24 (dd, J=5.9 and 13.7 Hz, 1H). 2.14 (s, 6H), 0.92 (d, J=6.5 Hz, 3H) ppm, shown in FIGS. 13 and 14. $^{13}C$ NMR (75 Hz, MeOH-$d_4$) δ 141.4, 140.7, 128.72, 128.65, 127.8, 127.6, 127.4, 127.2, 122.8, 55.4, 49.6, 43.31, 39.9 ppm, shown in FIGS. 15 and 16. Specific optical rotation: $[α]^{25}_D$ −50.3° (c 0.70, EtOH). Elemental analysis: Calc'd for $C_{19}H_{22}N_2$: C, 81.97%; H, 7.97%; N, 10.06%. Found: C, 81.46%; H, 8.01%; N, 10.00%. Chiral HPLC revealed the presence of a single enantiomer of intermediate (E) (e.e. >99%) under conditions shown in Example 4.A. The optical purity of levomethadone nitrile was further confirmed by its optical rotation, $[c]^{25}_D$ −50.3° (c 0.70, EtOH) (literature value −49-50.2°). Literature Data: −50.2° (c 0.71, EtOH) (U.S. Pat. No. 6,143, 933A); −49° (C. J. Barnett and J. C. Smirz, J Org Chem 1976, 41, 710); and $[α]^{18}_D$ −49°, c 1.3, EtOH (Beckett et al., J Chem Soc, 1957, 858-61).

Example 4.A. Chiral HPLC Method for Levomethadone Nitrile

Analytical Chiral High Pressure Liquid Chromatography (chiral HPLC) of the levomethadone nitrile (E) was performed under the following conditions. For example, chiral HPLC Conditions for comparative rac-Methadone Nitrile and Levomethadone Nitrile (E) of Example 3 were as follows. Chiral HPLC was performed using a chiral stationary phase Column: Phenomenex Lux 3 mm, Cellulose-3, 150×4.6 mm, Part No. 00%-4492-E0, with Mobile Phase 90:10:0.1 n-Hexane:Isopropanol:Diethylamine at Column Temperature of 300° C. with a Flow Rate of 1.0 mL/min, and UV monitoring at Wavelength 254 nm, with Injection Volume of 5 uL, following dissolving the Sample in 200 proof ethanol.

Chiral HPLC chromatogram by this method of levomethadone nitrile intermediate (E) from Example 3 revealed the presence of a single enantiomer (e.e. >99%), as shown in FIG. 17. In comparison, a chiral HPLC chromatogram of racemic Methadone Nitrile performed under the same conditions is shown in FIG. 18, showing presence of two enantiomers in about a 1:1 ratio. The limit of detection (LOD/limit of quantitation (LOQ) for levomethadone nitrile/dextromethadone nitrile by this chiral HPLC method, based on initial evaluation 10/100 ppm (LOD/LOQ). No dextromethadone nitrile was detected by chiral HPLC.

Example 4.B. Reverse-Phase HPLC Method

Analytical Reverse-Phase (RP)-High Pressure Liquid Chromatography (RP-HPLC) of the final product and intermediates disclosed herein was performed under the following conditions. RP-HPLC was performed using a C18 stationary phase with a Gemini® 5 μm C18 110 Å, LC Column 150×4.6 mm, Part: 00F-4435-E0. The method was run under HPLC Conditions: Mobile phase: 100 mL: 900 mL (mobile phase B (pH 9.25): $ACN/H_2O$ (5:4 mixture)); at a Flow rate of 1 mL/min, at 35° C., and with monitoring at 210 nm. Preparation of RP HPLC buffer was as follows.

A: Dissolve 6.9 g of $NaH_2PO_4×H_2O$ in 2000 mL of water. Add 10.8 g of Dodecyl Sulfate, Sodium Salt and mix until well dissolved. Filter. Adjust the pH to 7.9 with triethylamine.

B: Combine 1460 mL of buffer with 300 mL acetonitrile and 240 mL of methanol and mix well. Adjust the apparent pH of mobile phase to a target range of 9.3 with 50% aqueous sodium hydroxide or 85% aqueous phosphoric acid solution.

An RP-HPLC chromatogram of a mixture of relevant intermediates and product is shown at FIG. 19A. As shown in FIG. 19A, this HPLC method results in baseline resolution of a mixture of (1) starting material reagent diphenylacetonitrile, (2) impurity isolevomethadone nitrile, (3) intermediate levomethadone nitrile, and (4) product levomethadone. A representative RP-HPLC chromatogram of levomethadone hydrochloride is shown in FIG. 22; less than 100 ppm of diphenylacetonitrile, isolevomethadone nitrile, and levomethadone nitrile impurities are detected at 210 nm. The RP-HPLC method of example 4B was able to quantify the regioisomer impurities and starting materials with at least 10 ppm accuracy.

Example 4.C. Reverse-Phase UPLC Method

Analytical Reverse-Phase (RP)-Ultra High Pressure Liquid Chromatography (RP-UPLC) of the final product and intermediates disclosed herein was performed under the following conditions. RP-HPLC was performed using a Waters Acquity BEH Shield RP 18, 1.7 um, 2.1×100. The method was run under UPLC Conditions: 85% Mobile phase A (buffer:organic mixture) and 15% Mobile Phase B (50:50 Acetonitrile to water mixture) and at a flow rate of 0.48 mL/min, at 40° C., and with monitoring at 220 nm. Preparation of RP UPLC mobile phase A was as follows.

A: Dissolve 6.9 g of $NaH_2PO_4 \times H_2O$ in 2000 mL of water. Add 10.8 g of Dodecyl Sulfate, Sodium Salt and mix until well dissolved. Filter. Adjust the pH to 7.9 with triethylamine.

B: Combine 1460 mL of buffer with 300 mL acetonitrile and 240 mL of methanol and mix well. Adjust the apparent pH of mobile phase to a target range of 8.8 with 50% aqueous sodium hydroxide or 85% aqueous phosphoric acid solution.

An RP-UPLC chromatogram of a mixture of relevant intermediates and product is shown at FIG. 23. As shown in FIG. 23, this UPLC method results in baseline resolution of a mixture of (1) benzophenone, (2) starting material reagent diphenylacetonitrile, (3) impurity isolevomethadone nitrile, (4) intermediate levomethadone nitrile, and (5) product levomethadone. A representative RP-UPLC chromatogram of levomethadone hydrochloride is shown in FIG. 24; less than 100 ppm of diphenylacetonitrile, isolevomethadone nitrile, and levomethadone nitrile impurities are detected at 210 nm. The RP-UPLC method of example 4C was able to quantify the regioisomer impurities and starting materials with at least 100 ppm accuracy.

Example 5. (−)-(R)-6-(Dimethylamino)-4,4-diphenyl-3-heptanone hydrochloride. Synthesis of Levomethadone Hydrochloride from Levomethadone Nitrile (E)

To a stirred solution of levomethadone nitrile (400 mg, 1.44 mmol) in anhydrous toluene (2 mL) in a 10 mL flask equipped with a condenser, ethyl magnesium bromide (3.0M in ether, 1.0 mL) was added dropwise under Argon. The reaction mixture was heated to remove the ether solvent through the condenser (a slow flow of Ar was applied from top of the condenser to assist the removal of ether). After ether was removed, the reaction was heated to 100° C. for 3.5 hours. The reaction mixture was cooled to ambient temperature and 6M HCl (3 mL) was carefully added (exthothermic, external cooling was necessary when adding HCl). The reaction was then stirred at 50° C. for 20 min before cooling to ambient temperature. The reaction mixture was neutralized with 20 mL 10% $Na_2CO_3$ (rapidly evolves gas) and extracted with EtOAc (2×15 mL). The combined organic extracts were washed with brine and dried over $Na_2SO_4$. After removal of the solvents, a thick oil (470 mg) was obtained.

$^1H$ NMR analysis indicated total consumption of the nitrile starting material and the crude contains a mixture of levomethadone and the imine intermediate. This crude was stirred with 6M HCl solution (3 mL) at 65° C. and concentrated to about one third of the total volume under reduced pressure. Acetone (3 mL) was then added to precipitate the $NH_4Cl$, which was filtered off. The filtrate was concentrated and co-evaporated with toluene (2×2 mL) to azeotropically remove the water. The solid crude was dissolved in a minimum amount of methanol and triturated with acetone. The solid was filtered and dried to give 386 mg of crystalline product levomethadone hydrochloride. An additional 82 mg was obtained from the acetone filtrate after concentration and recrystallization. Yield of levomethadone hydrochloride from intermediate E: 94%.

For levomethadone hydrochloride: Chiral HPLC: one single enantiomer (e.e. >99%), as shown in Example 6 and FIG. 21. Specific optical rotation: $[\alpha]^{25}_D$ −135.4° (c=1.96, EtOH); m.p. ($H_2O$), 240.6-241.3° C. $^1H$ NMR (300 MHz, MeOH-$d_4$) δ 7.38-7.54 (m, 8H), 7.22-7.45 (d, J=7.5 Hz, 2H), 3.10-3.17 (m, 2H), 2.87 (s, 3H), 2.84 (s, 3H), 2.53-2.66 (m, 1H), 2.07-2.20 (m, 2H), 0.89 (t, J=7.2 Hz, 3H), 0.61 (d, J=6.9 Hz) ppm. $^{13}C$ NMR (75 Hz, MeOH-$d_4$) δ 213.4, 140.7, 139.9, 129.2, 128.91, 128.90, 128.6, 127.84, 127.80, 65.7, 60.6, 41.0, 40.1, 37.4, 33.3, 13.5, 8.12 ppm. Elemental analysis: Calc'd for $C_{21}H_{18}ClNO$: C, 72.92%; H, 8.16%; N, 4.05%. Found: C, 72.95%; H, 8.06%; N, 4.13%.

Example 6. Chiral HPLC Method for levomethadone hydrochloride; (−)-(R)-6-(dimethylamino)-4,4-diphenyl-3-heptanone hydrochloride Analytical Chiral High Pressure Liquid Chromatography (chiral HPLC) of the levomethadone hydrochloride from Example 5 was performed under the following conditions.

Column: Phenomenex 5 μm Cellulose-4, 150×4.6 mm, part no. 00F-4491-E0 or a Phenomenex 5 um Cellulose-4, 250×4.6 mm, part no. 00G-4491-E0; Mobile Phase A: n-Hexane+0.1% Diethylamine; Mobile Phase B:Isopropanol+0.1% Diethylamine run at a Gradient of 98:2 mobileA: mobile B at Flow:1.5 mL/minute, with a Column Temperature of 25° C.; and Run Time:>4 minutes; with Sample Preparation:20 mg/mL Levomethadone in Ethanol and monitored at Wavelength:254 nm or 292 nm. (−)-(R)-6-(Dimethylamino)-4,4-diphenyl-3-heptanone hydrochloride (levomethadone hydrochloride) product of Example 5 was characterized by chiral HPLC and RP-HPLC, by the methods of Examples 6 and 4B, respectively.

Chiral HPLC of levomethadone HCl product is shown in FIG. 21, compared to FIG. 20, showing chiral HPLC of comparative racemic methadone HCl. Based on initial screening, the limit of detection (LOD)/limit of quantitation (LOQ) for dextromethadone impurity by this chiral HPLC method is 10/100 ppm (LOD/LOQ). The levomethadone hydrochloride produced by the route shown in Examples 1-3 and 5 comprises not more than 100 ppm, 50 ppm, or 10 ppm of dextromethadone, as detected by the chiral HPLC method this example.

The LOD/LOQ for these impurities by the method of Example 4B was in the 10 ppm range. See FIG. 19A for RP-HPLC of a mixture of diphenylacetonitrile, levomethadone nitrile, isolevomethadone nitrile, and isolevomethadone. The levomethadone hydrochloride produced by the route shown in Examples 1-3 and 5 comprises not more than 100 ppm, 50 ppm, or 10 ppm of an impurity selected from diphenylacetonitrile, levomethadone nitrile, isolevomethadone nitrile, and isolevomethadone as detected by reverse phase HPLC method of Example 4B.

Example 7. Synthesis of N,N-Dimethyl D-Alaninol (C) from D-Alanine (A)

In this example, N-dimethyl D-alaninol (C) is obtained from D-alanine (A) in a single pot representative of Operational Step 1. 5-L RBF was charged with 1.2 L THF and cooled to 0° C. ZnCl$_2$ (166.0 g, 1.2 mol, 1.2 eq) was added in portions under stirring. After stirring for 10 min, ZnCl$_2$ dissolved to give a slightly cloudy solution. NaBH$_4$ (90.8 g, 2.4 mol, 2.4 eq) was added in portions while maintaining the reaction temperature at 0° C. The resulting mixture was heated to 40° C. for 4 h to give a white suspension. The reaction mixture was then cooled to 0° C. and D-alanine (89.1 g, 1 mol, 1 eq) was added in one portion. The ice bath was removed and the reaction mixture warmed to rt and heated to 40° C., at which temperature rapid hydrogen gas evolution started. The reaction mixture was maintained at 40° C. for 1 h until rapid hydrogen gas evolution ceased. The reaction mixture was then heated to gentle reflux (bath T=70° C.) for 5 h. The reaction mixture was cooled to 0° C. and carefully quenched by dropwise addition of 0.5 L MeOH at 0° C. The mixture was left to warm to rt and stirred overnight to give a viscous grey suspension. The reaction mixture was diluted with water (1 L). H$_3$PO$_4$ (75 mL) was then slowly added and the mixture (pH ~4) was thoroughly stirred until a fine white/grey suspension resulted (about 6 h). The resulting mixture was filtered through a short pad of Celite covered with a filter paper and the filter cake was washed with water (200 mL×4). The combined filtrate was concentrated down to about 300 mL in volume on a rotavap. The white solid that precipitated out was again filtered off and washed with 75 mL×2 water to give about 500 mL final solution containing the crude D-alaninol.

The aqueous solution was neutralized with NaOH (40 g) at 0° C. Formaldehyde (37%, 186 mL, 2.5 eq) was added at 0° C. followed by formic acid (189 mL, 5 eq). The resulting reaction mixture was stirred at 110° C. for 12 h. The reaction mixture was evaporated to dryness at 55° C. and co-evaporated with water (200 mL×2). The residue was suspended in 125 mL water and treated with NaHSO$_3$ (60 g). After stirring overnight, a sample of the mixture was analyzed by $^1$H NMR.

The reaction mixture was concentrated down to a volume of about 200-300 mL and cooled to 0° C. Cold 50% NaOH (100 mL) was added at 0° C. to the reaction mixture while stirring, leading to oiling out of the product. The product was extracted by thoroughly mixing with MTBE (300 mL) and decanting into an Erlenmyer flask. The product was further extracted by mixing thoroughly with MTBE (200 mL×4) and decanting into the Erlenmyer flask. The combined MTBE extracts were dried over Na$_2$SO$_4$ (120 g) overnight under stirring. Na$_2$SO$_4$ was filtered off, the residue washed with MTBE (50 mL×2). The combined filtrates were evaporated in vacuo to give 101.0 g of crude product. $^1$H NMR revealed the presence of 5 mol % MTBE corresponding to 96 wt % or 96.7 g (94%) of the crude product.

The N,N-dimethyl D-alaninol was analyzed by HPLC, $^1$H-NMR and Karl Fisher analysis. $^1$H-NMR (300 MHz, MeOH-d$_4$) δ 3.62 (dd, J=6.0 and 11.0 Hz, 1H), 3.44 (dd, J=6.2 and 11.0 Hz, 1H), 2.63 (sext, J=6.4 Hz, 1H), 2.29 (s, 6H), 1.04 (d, J=6.7 Hz, 3H) ppm. Water content was determined by Karl Fisher method to be 1.4% by mass.

The reaction was repeated three other times providing a total of 400 g of crude product as yellow oil. Combined products were dried under molecular sieves before being used in Unit Operation 2 for the synthesis of levomethadone nitrile.

Example 8. Synthesis of Levomethadone Nitrile (E) from N,N-Dimethyl D-Alaninol (C)

Starting crude alcohol N,N-dimethyl D-alaninol prepared by the method of Example 7 was characterized with 0.28% water (Karl Fisher), 5 mol % MTBE (1H-NMR) (4.3 wt %) so the dry material was determined to be 95.7% pure (100 g crude corresponds to 95.4 g or 0.926 mol N,N-dimethyl D-alaninol).

To a solution of the crude alcohol (108.0 g crude, 1.0 mol) in 2.0 L anhydrous THF in a 20 L reactor was added para-toluene sulfonyl chloride (TsCl) (203.4 g, 1.07 mol) portion wise at 0° C. under agitation and the reaction mixture was agitated for 5 min till fully dissolved. Potassium t-butoxide (KOtBu) (125.4 g, 1.12 mol) was added slowly as fine powders at 0° C. A white precipitate started to form immediately after KOtBu was introduced. The reaction was slowly warmed to 25° C. and agitated for 1.0 h. DMF (6.0 L) was added followed by diphenylacetonitrile (155.0 g, 0.800 mol). After the resulting mixture was agitated for 10 min and cooled to 0° C., KOtBu (108.0 g 0.96 mol) was added in small portions at 0° C. The reaction mixture was slowly warmed to rt (30 min), sampled and analyzed by HPLC (49.4% conversion to product) and then warmed to 50° C. and left to run overnight. Samples were taken and analyzed by HPLC at 40 min (64.7% conversion to product) and 16 h (84.2% conversion to product; levomethadone nitrile/isolevomethadone nitrile in 76:24 ratio).

The reaction mixture was cooled to 0° C. and quenched with 4.0 L of 0.5 M HCl to attain a pH ~2 and then washed with PhMe (1.5 L×2). The aqueous phase was basified with a solution of 48 g NaOH in 0.6 L water to attain a pH of ~10 and extracted with MTBE (2.0 L×2). The MTBE extracts were washed with H$_2$O (2.0 L) and 30% brine (0.6 L), dried over Na$_2$SO$_4$ (100 g), filtered and concentrated to give 177.52 g of the crude product as a white solid. The crude product was triturated overnight with petroleum ether (180 mL), and the product was obtained as a white solid (105.05 g) after filtration and drying and analyzed by HPLC (97.4% purity by HPLC). HPLC analysis of the crude product after trituration with pet ether showed the ratio of levomethadone nitrile/isolevomethadone nitrile to be 97.4:2.6).

The product (E) was further purified by a first recrystallization: 105.5 g of product were dissolved in 320 mL of heptane at 80° C. and left to stand at rt overnight. The product was obtained as white solid (90.66 g) and analyzed by HPLC (99.6% purity). HPLC analysis of levomethadone nitrile after first recrystallization with heptane showed levomethadone nitrile purity by HPLC of 99.6%, monitored at 210 nm, as shown in FIG. 19B.

The product was further purified by a second recrystallization: 90.66 g of product were dissolved in 270 mL of heptane at 80° C. and left to stand at rt overnight. The product was obtained as white solid (85.88 g, 38% yield) and analyzed by HPLC. HPLC analysis of levomethadone nitrile after first recrystallization with heptane showed levomethadone nitrile purity by HPLC of 100%, monitored at 210 nm, as shown in FIG. 19C. The product levomethadone nitrile (E) was analyzed by proton NMR. $^1$H-NMR (300 MHz, MeOH-d$_4$) δ 7.27-7.42 (m, 10H), 2.70 (dd, J=6.5 and 13.7 Hz, 1H), 2.55 (sext, J=6.4 Hz, 1H), 2.25 (dd, J=5.8 and 13.7 Hz, 1H), 2.15 (s, 6H), 0.93 (s, J=6.5 Hz) ppm.

Example 9. Synthesis of Levomethadone Hydrochloride from Levomethadone Nitrile (E)

A 2-L three neck flask equipped with a condenser and an Ar inlet/outlet was charged with levomethadone nitrile (125.3 g, 0.450 mol) and anhydrous toluene (450 mL) under Ar. The reaction mixture was cooled to 0° C. with an ice-water bath and ethyl magnesium bromide (3.0M in ether, 300 mL) was added dropwise through an addition funnel over 20 min. After the Grignard reagent was added, the condenser was arranged for distillation. The reaction mixture was slowly heated to 40° C. and then to 60° C. till ether was all distilled off. The reaction was then heated to reflux (bath: 110° C.) for 3 hours. After being cooled to 0° C. (ice-water bath), the Ar lines were removed and the reaction system was opened to the air. The reaction was carefully quenched by dropwise addition of 15 ml of water followed by 6M HCl (750 mL) under cooling (ice-water bath). The reaction mixture was gradually heated to 70° C. and stirred for 3 h at this temperature to ensure the complete hydrolysis of the imine intermediate as revealed by HPLC. The reaction mixture was cooled to ambient temperature and neutralized by dropwise addition of a solution of 215 g NaOH in 540 mL water under cooling (ice-water bath). After warming to ambient temperature, the resulting mixture (pH ~10) was extracted with MTBE (1.0 L×4). The combined organic extracts were washed with water (1 L) and brine (1 L) and dried over $Na_2SO_4$ (200 g). After concentrating under reduced pressure to about 250-300 mL of total volume (total mass ~260 g), the crude levomethadone free base was treated with 6M HCl (100 mL) under cooling (ice-water bath). After stirring at rt for 15 min, solvents and volatiles were removed under reduced pressure at 50° C. and then 60° C. Residual water was removed by co-evaporation with toluene (150 mL×2). The resulting reaction crude was further co-evaporated with acetone (150 mL×2) to give the crude product as a free flow solid.

Purification: the solid crude was taken up with hot methanol (80 mL) and triturated with acetone (240 mL) at gentle reflux for 15 min. The resulting mixture was gradually cooled to ambient temperature. After stirring overnight, the solid precipitate was filtered, washed with cooled acetone (50 mL×2) and dried in a vacuum oven at 65° C. for 8 h to give 114.8 g of levomethadone hydrochloride as white crystalline powders. The mother liquor was concentrated to dryness and triturated with 100 mL acetone under gentle reflux. After cooling to rt and stirring overnight, a second crop of the product (28.3 g) was obtained after filtration and washing with cooled acetone (20 ml×2). Total yield: 143.1 g (92%). The final mother liquor was concentrated and the residue saved for further purification. Characterization of levomethadone hydrochloride prepared in Example 9. Chiral HPLC: one single enantiomer (e.e. >99%). Specific optical rotation: $[\alpha]^{25}_D$ –130° (c=5.0%, water). $^1$H-NMR (300 MHz, MeOH-$d_4$) δ 7.38-7.49 (m, 8H), 7.23 (d, J=7.5 Hz, 2H), 3.07-3.16 (m, 2H), 2.85 (s, 6H), 2.53-2.66 (m, 1H), 2.07-2.20 (m, 2H), 0.89 (t, J=7.2 Hz, 3H), 0.60 (d, J=6.7 Hz, 3H) ppm. $^{13}$C-NMR (75 MHz, D2O) δ 216.75, 140.20, 139.50, 129.23, 129.10, 129.80, 129.11, 65.68, 60.35, 40.75, 40.57, 33.65, 13.63, 8.53 ppm.

Example 10. Synthesis of N,N-Dimethyl L-Alaninol from L-Alanine

A synthetic route for preparation of N,N-Dimethyl L-Alaninol from L-alanine is shown in FIG. 25A. A 1 L-RBF was charged with $ZnCl_2$ (33 g, 240 mmol) and THF (240 mL) under Ar. After stirring for 10 min, $NaBH_4$ (18.2 g, 480 mmol) was added in portions and the resulting mixture stirred at rt for 16 h. After cooling to 0° C., L-alanine (17.8 g, 200 mmol) was added portionwise at 0° C. The reaction mixture was warmed to rt over 30 min and heated to reflux (bath T=70° C.) for 5 h. Formation of grey particles, presumably metallic Zn, was noticed. After cooling to rt, the reaction was carefully quenched by dropwise addition of 150 mL MeOH at 0° C. over 30 min. The reaction mixture was slowly warmed to rt and stirred for 30 min till gas evolution ceased before heated to reflux for 16 h. The reaction mixture was then cooled to rt and diluted with 200 mL of water. $H_3PO_4$ (~21 mL) was added dropwise and the resulting white suspension was stirred at rt for 2 h to cause precipitation of inorganic salts. The resulting mixture (pH ~3.4) was filtered through a short pad of Celite. The filter cake was washed sequentially with water (50 mL×2) and MeOH (25 mL×2). The combined filtrate (pH 3.4) was concentrated to about 150-200 mL of total volume. The precipitated inorganic salt in the concentrated filtrate was filtered and washed with a small amount of water. The combined filtrate (pH ~2.6) was saved for use in the next step for the synthesis of N,N-dimethyl-L-alaninol. The crude L-alaninol was characterized in aqueous solution by $^1$H-NMR at pH 2.6. $^1$H-NMR (300 MHz, $D_2O$) δ 3.68 (dd, J=3.7 and 12.1 Hz, 1H), 3.47 (dd, J=7.1 and 12.1 Hz, 1H), 3.31-3.41 (m, 1H), 1.17 (d, J=6.7 Hz, 3H).

The acidic aqueous solution (pH 2.6) containing the crude L-alaninol was neutralized with NaOH (8.1 g) at 0° C. to pH 8.0. Formaldehyde (37 mL, 2.5 eq) was added at 0° C. followed by formic acid (38 mL, 5 eq). The resulting reaction mixture (pH 2.5) was heated to reflux (bath T 110° C.) and the progress of the reaction was monitored by H-NMR in $D_2O$. After the dimethylation reaction went to completion as judged by H-NMR, the reaction mixture was cooled to rt and evaporated at 55° C. till about 100 mL of total volume and co-evaporated co-evaporated with water (200 mL×2) to ~100 ml in volume. Sat. $NaHSO_3$ (20 mL) was added to the concentrated reaction mixture and the resulting mixture stirred at rt for 3.5 h. The solid precipitate was filtered and washed with water (10 mL×3). The combined clear filtrate (pH ~3.0) was treated with solid NaOH (15 g) at 0° C. to give a free flow pasty liquid (pH ~10) which was extracted with MTBE (200 mL×4). The aqueous layer was analyzed by H-NMR which revealed that significant amount of the product was still in the aqueous phase. Four more extractions with MTBE (200 mL each) were performed. The combined MTBE extracts were dried over $MgSO_4$ (30 g) and concentrated at 20-25° C. under reduced pressure to give 9.49 g of crude product as an oil. H NMR showed a 1:6.4 molar ratio between residual MTBE and the product, corresponding to a 88% content or 8.35 g of N,N-dimethyl D-alaninol (40.5% yield). The product N,N-dimethyl D-alaninol was characterized by $^1$H-NMR and $^{13}$C-NMR. $^1$H-NMR (300 MHz, MeOH-$d_4$) δ 3.62 (dd, J=6.0 and 11.0 Hz, 1H), 3.44 (dd, J=6.2 and 11.0 Hz, 1H), 2.63 (sext, J=6.4 Hz, 1H), 2.29 (s, 6H), 1.04 (d, J=6.6 Hz, 3H) ppm. $^{13}$C-NMR (75 MHz, MeOD) δ 63.15, 60.63, 39.96, 10.18 ppm.

Example 11. Synthesis of Dextromethadone Nitrile from N,N-Dimethyl L-Alaninol Synthesis of dextromethadone nitrile from N,N-Dimethyl L-Alaninol was performed by the route shown in FIG. 25B. To a stirred solution of N, N-dimethyl L-alaninol (9.49 g crude containing 12% MTBE, ~80 mmol) in 100 mL anhydrous THF was added para-toluene sulfonyl chloride (TsCl) (17.2 g, 90 mmol) portion wise at 0° C. Potassium t-butoxide (KOtBu) (10.1 g, 90 mmol) was added in portions as fine powders at 0° C. White precipitate started to form immediately after KOtBu was added. The reaction mixture was slowly warmed to rt and stirred for 45 min to give the tosylate crude. DMF (300 mL) was then added followed by diphenyacetonitrile (12.6 g, 65 mmol). After the resulting mixture was degassed for 10 min and cooled with ice water bath, KOtBu (8.4 g, 75 mmol) was added in small portions at 0° C. The reaction mixture was slowly warmed to rt and then to 50° C. and the reaction mixture was stirred at this temperature for 15 h. After cooled to rt, the reaction mixture was poured into 400 mL 0.3M HCl at 0° C. and the resulting mixture (pH ~2.2) was washed with PhMe (200 mL×2). The aqueous phase was basified with a solution of 5 g NaOH in 15 mL water and the resulting mixture (pH ~10) and extracted with MTBE (150 mL, then 100 mL×2). The MTBE extracts were washed with water (100 mL) and brine (100 mL) and dried over $Na_2SO_4$ (20 g). After concentration at 55-60° C. on under reduced pressure, the semisolid crude (12.7 g) was triturated with 30 mL pet ether at reflux. After standing overnight at rt, the solid precipitate was filtered and washed with pet ether (3 mL×2) to give 5.70 g of crude dextromethadone nitrile as an off white solid. The solid crude was dissolved in 20 mL heptane at 80-85° C. After cooling to rt and stirring overnight, the solid was filtered and washed with heptane (3 mL×2). After drying under vacuum at 50° C. for 2 h, pure dextromethadone nitrile (3.5 g, 29.6% based on diphenylacetonitrile) was obtained as white powders. HPLC revealed a purity of 99.8% of the final dextromethadone nitrile product. The dextromethadone nitrile was characterized by $^1$H-NMR and $^{13}$C-NMR. $^1$H-NMR (300 MHz, MeOH-$d_4$) δ 7.31-7.45 (m, 10H), 2.70 (dd, J=4.4 and 13.6 Hz, 1H), 2.58 (sext, J=6.2 Hz, 1H), 2.41 (dd, J=7.1 and 13.8 Hz, 1H), 2.15 (s, 6H), 0.91 (s, J=6.5 Hz) ppm. $^{13}$C-NMR (75 MHz, MeOD) δ 141.03, 140.56, 128.51, 128.47, 127.63, 127.56, 126.90, 126.81, 122.44, 55.77, 49.62, 41.55, 38.78, 13.11 ppm.

Example 12. Synthesis of Dextromethadone Hydrochloride from Dextromethadone Nitrile Synthesis of dextromethadone hydrochloride was performed by the route illustrated in FIG. 25C. A 100-mL three neck flask equipped with a condenser, an Ar inlet and an outlet was charged with dextromethadone nitrile (4.18 g, 15 mmol) and anhydrous toluene (20 mL). The reaction mixture was cooled to 0° C. with an ice water bath and ethyl magnesium bromide (3.0 M in ether, 10 mL) was added dropwise via syringe to an addition funnel over 2 min under Argon. After the Grignard reagent was added, the condenser was arranged for distillation. The reaction mixture was slowly heated to 40° C. and then to 60° C. till ether was all distilled off. The reaction was then heated to reflux (bath: 110° C.) for 3 h. After being cooled to 0° C. (ice water bath), the Ar lines were removed and the reaction system was opened to the air. The reaction was carefully quenched by dropwise addition of 1 mL water followed by 6M HCl (25 mL) under cooling (ice water bath). The reaction mixture was then stirred at 75° C. for 3 h to ensure complete hydrolysis of the imine intermediate as revealed by HPLC analysis. The reaction mixture was cooled to ambient temperature and neutralized by dropwise addition of a solution of 7.4 g NaOH in 20 mL water under cooling. The resulting mixture (pH ~10) was then extracted with MTBE (50 mL×3). The combined organic extracts were washed with water (100 mL) and brine (100 mL) and dried over $Na_2SO_4$ (10 g). After concentrated under reduced pressure to about 10 mL of total volume (mass ~13 g), the crude product was treated with 6 M HCl (3 mL) at under cooling (ice water bath) and stirred at rt for 15 min. Solvents and volatiles were removed under reduced pressure at 50-60° C. Residual water was removed by co-evaporation with toluene (10 mL×2). The resulting reaction crude was further co-evaporated with methanol (10 mL) and acetone (10 mL) to give the crude dextomethadone hydrochloride. The solid crude was triturated with acetone (10 mL) under gentle reflux for 15 min. The resulting mixture was slowly cooled to rt and the solid precipitate was filtered, washed with acetone (5 mL×2) and dried in a vacuum oven at 65° C. for 4 h to give 3.83 g of dextomethadone hydrochloride as white crystalline powders. The mother liquor was concentrated to dryness and triturated with 5 mL acetone under gentle reflux. After cooling to rt, a second crop of the product (0.75 g) was obtained after filtration and washing with cooled acetone (2 ml×2). Total yield: 4.58 g (88%). Enantiomeric purity, e.e >99% (Chiral HPLC, one single enantiomer). Chiral chromatogram of dextromethadone hydrochloride is shown at FIG. 26B. Specific optical rotation: $[α]_D$: +127.4° (c=5.0%, $H_2O$, 25° C.). The product dextromethadone hydrochloride was further characterized by $^1$H- and $^{13}$C-NMR. H-NMR (300 MHz, MeOH-$d_4$) δ 7.36-7.49 (m, 8H), 7.23 (d, J=7.7 Hz, 2H), 3.07-3.16 (m, 2H), 2.85 (s, 6H), 2.53-2.66 (m, 1H), 2.07-2.20 (m, 2H), 0.88 (t, J=7.2 Hz, 3H), 0.59 (d, J=6.7 Hz, 3H) ppm. $^{13}$C-NMR (75 MHz, MeOH-$d_4$) δ 213.68, 140.67, 139.82, 129.20, 128.88, 128.84, 128.56, 127.84, 127.80, 65.69, 60.60, 41.19, 40.22, 37.14, 33.29, 13.29, 8.04.

REFERENCES CITED

Amani et al.; Zeitschrift fuer Kristallographie—New Crystal Structures (2005), 220(4), 549-550; Crystal structure of 2,2-diphenyl-4-dimethylaminopentanenitrile, C19H22N2.

Ansermot et al., Arch Intern Med 170(6), 529-536, Mar. 22, 2010; Substitution of (R,S)-Methadone by (R)-Methadone Attenburrow et al., Journal of the Chemical Society (1949) 510-18; Analgesics. II. The synthesis of amidone and some of its analogs Barnett et al., Journal of Organic Chemistry (1976), 41(4), 710-11; Stereochemistry of Bockmuehl's synthesis of methadone Beckett et al., J Chem Soc, 1957, 858-861; Configurational studies in synthetic analgesics. Synthesis of (−)-methadone from D (−)-alanine.

Berge, et al. "Pharmaceutical Salts," J. Pharma. Sci. 1977; 66:1

Bhattacharyya, Synth. Commun. 1995, 25, 2061-2069; Borohydride reductions in dichloromethane: a convenient, environmentally compatable procedure for the methylation of amines.

Bracher et al., Scientia Pharmaceutica (Sci. Pharrn.) 64, 271-278 (1996); Ein neuer Zugang zu isomerenreinem (±)-Methadon (A Novel Approach to Isomeric Pure (±)-Methadone)

Brode and Hill, Journal of the American Chemical Society (1947), 69, 724; Rearrangement of the isomeric 1,2-(dimethylamino)-chloropropanes. The synthesis of amidone.

European Pharmacopoeia 8.0, Levomethadone hydrochloride Monograph of 01/2008:1787 corrected 6.5. pp. 2614-2615.

Moryl et al., Journal of Opioid Management 12:1, January/February 2016, 47-55; A phase I study of D-methadone in patients with chronic pain Paterson et al., Org Lett 2013, 15, 3118-3121; Total synthesis of Aplyronine C Porter, Pure & Appl Chem 63(8):1119-1122, 1991, Resolution of chiral drugs Poupaert, Journal of Chemical Research, Synopses (1981), (7), 192; Dibenzo-18-crown-6 as phase transfer catalyst in Bockmuehl's synthesis of methadone Schultz et al., Journal of the American Chemical Society (1948), 70, 48-52; Preparation and rearrangements of 1(or 2)-dimethylamino 2(or 1)-chloropropanes Tajbakhsh et al., Synthesis, 2011, 490-496; Catalyst-free one-pot reductive alkylation of primary and secondary amines and N,N-dimethylation of amino acids using sodium borohydride in 2,2,2-trifluoroethanol Weiberth et al., Journal of Organic Chemistry (1987) 52, 3901-3904, Copper(I)-activated addition of Grignard reagents to nitriles. Synthesis of ketimines, ketones and amines.

U.S. Pat. No. 2,497,739
U.S. Pat. No. 2,540,636
U.S. Pat. No. 2,601,323
U.S. Pat. No. 4,048,211
U.S. Pat. No. 4,242,274
U.S. Pat. No. 6,143,933
U.S. Publication US2014/0088155
U.S. Publication US2014/0350302
WO 2012/162635
SK 287446 B6

We claim:

1. A process for preparing levomethadone hydrochloride from D-alanine or dextromethadone hydrochloride from L-alanine, the process comprising:
    reducing the D-alanine to form D-alaninol or reducing the L-alanine to form L-alaninol; and
    converting the D-alaninol to form the N,N-dimethyl-D-alaninol or converting the L-alaninol to N,N-dimethyl-L-alaninol;
    combining the N,N-dimethyl-D-alaninol or the N,N-dimethyl-L-alaninol with an activating reagent to form a R-activated intermediate or an S-activated intermediate, respectively;
    mixing the R- or S-activated intermediate and a base with diphenylacetonitrile to provide levomethadone nitrile or dextromethadone nitrile, respectively; and
    exposing the levomethadone nitrile or dextromethadone nitrile to a Grignard reagent of formula RMgX, where R is ethyl and X=Cl, Br, or I, to form a reaction mixture; and
    adding hydrochloric acid to the reaction mixture to provide levomethadone hydrochloride or dextromethadone hydrochloride, respectively.

2. The process for preparing levomethadone hydrochloride according to claim 1, wherein the converting step comprises:
    reducing the D-alanine to form D-alaninol; and
    converting the D-alaninol to form the N,N-dimethyl-D-alaninol.

3. The process of claim 1 or claim 2, wherein the reducing comprises exposing the D-alanine or L-alanine to one or more reducing agents selected from the group consisting of LiAlH$_4$, BH$_3$/THF, BH$_3$/Et$_2$O, BH$_3$/BF$_3$ Et$_2$O, BH$_3$/Me$_2$S, NaBH$_4$/I$_2$, BH$_4$/cyanuric chloride, NaBH$_3$CN/ZnCl$_2$, NaBH$_4$/ZnCl$_2$, Zn(BH$_4$)$_2$, and NaBH$_4$/BF$_3$.Et$_2$O.

4. The process of claim 3, wherein the reducing agent is LiAlH$_4$ or Zn(BH$_4$)$_2$.

5. The process of claim 1, wherein the activating reagent is selected from the group consisting of thionyl chloride, methanesulfonyl chloride, p-toluenesulfonyl chloride, trifluoromethanesulfonyl chloride, methanesulfonic anhydride, trifluoromethanesulfonic anhydride, and p-toluenesulfonic anhydride.

6. The process of claim 5, wherein the R-activated intermediate is selected from the group consisting of (R)-1-chloro-N,N-dimethylpropan-2-amine HCl, (R)-1-chloro-N,N-dimethylpropan-2-amine, (R)-2-(dimethylamino)propyl 4-methylbenzenesulfonate, and (R)-2-(dimethylamino)propyl methanesulfonate.

7. The process of claim 5, wherein the S-activated intermediate is selected from the group consisting of (S)-1-chloro-N,N-dimethylpropan-2-amine HCl, (S)-1-chloro-N,N-dimethylpropan-2-amine, (S)-2-(dimethylamino)propyl 4-methylbenzenesulfonate, and (S)-2-(dimethylamino)propyl methanesulfonate.

8. The process of claim 6 or claim 7, wherein the R-activated intermediate or the S-activated intermediate is isolated and used in the reacting step; or the R-activated intermediate or the S-activated intermediate is used directly in the next reacting step without isolation after the activated intermediate is formed.

9. The process of claim 6 or claim 7, wherein the mixing comprises exposing the R- or S-activated intermediate to a base and diphenylacetonitrile in a solvent to form the levomethadone nitrile or dextromethadone nitrile, respectively.

10. The process of claim 9, wherein the levomethadone nitrile or dextromethadone nitrile is formed in >99% enantiomeric excess (e.e.).

11. The process of claim 9, wherein the base is selected from the group consisting of sodium hydroxide, potassium hydroxide, potassium t-butoxide, sodium t-butoxide, sodium methoxide, potassium methoxide, sodium ethoxide, potassium ethoxide, sodium tert-pentoxide, potassium tert-pentoxide sodium isopropoxide, and potassium isopropoxide.

12. The process according to claim 11, wherein the base is potassium t-butoxide.

13. The process of claim 9, wherein the solvent is selected from the group consisting of dimethylformamide, dimethylacetamide, tetrahydrofuran, dimethyl sulfoxide, N-methyl-2-pyrrolidone, dioxane, and water, or a combination thereof.

14. The process of claim 1, wherein the exposing comprises
    adding the Grignard reagent having formula RMgX, where R is ethyl and X=Br, to a stirred solution of levomethadone nitrile or dextromethadone nitrile in an anhydrous solvent to form the reaction mixture;
    heating the reaction mixture to a temperature above ambient temperature;
    cooling the reaction mixture;
    adding hydrochloric acid to the reaction mixture; and
    isolating the levomethadone hydrochloride or the dextromethadone hydrochloride from the reaction mixture, respectively.

15. The process of claim 1, wherein the levomethadone hydrochloride or the dextromethadone hydrochloride is produced in >99% enantiomeric excess (e.e.).

16. The process of claim 1, wherein the levomethadone hydrochloride comprises not more than 0.05%(500 ppm), 0.025%(250 ppm), or 0.01%(100 ppm) of an impurity selected from the group consisting of dextromethadone hydrochloride, dextromethadone, isodextromethadone, isodextromethadone hydrochloride, isolevomethadone, isolevomethadone hydrochloride, levomethadone nitrile, dextromethadone nitrile, isolevomethadone nitrile, isodextromethadone nitrile, diphenylacetonitrile, 2(S)-2-[[(4-methylphenyl)sulphonyl]amino]pentanedioic acid (N-tosyl-L-glutamic acid), a tartaric acid, and a bromocamphor sulfonic acid.

17. The process of claim 1, wherein the dextromethadone hydrochloride comprises not more than 0.05%(500 ppm), 0.025%(250 ppm), or 0.01%(100 ppm) of an impurity selected from the group consisting of levomethadone hydrochloride, levomethadone, isolevomethadone, isolevomethadone hydrochloride, isodextromethadone, isodextromethadone hydrochloride, dextromethadone nitrile, levomethadone nitrile, isodextromethadone nitrile, isolevomethadone nitrile, diphenylacetonitrile, 2(R)-2-[[(4-methylphenyl)sulphonyl] amino]pentanedioic acid (N-tosyl-L-glutamic acid), a tartaric acid, and a bromocamphor sulfonic acid.

18. The process of claim 1, wherein the levomethadone hydrochloride comprises not more than 100 ppm of an impurity selected from the group consisting of dextromethadone, diphenylacetonitrile, levomethadone nitrile, isolevomethadone nitrile, and isolevomethadone.

19. The process of claim 1, wherein the dextromethadone hydrochloride comprises not more than 100 ppm of an impurity selected from the group consisting of levomethadone, diphenylacetonitrile, dextromethadone nitrile, isodextromethadone nitrile, and isodextromethadone.

20. The process of claim 14, wherein the heating to above ambient temperature is heating the reaction mixture at a temperature up to the reflux temperature of the anhydrous solvent.

21. The process of claim 14, wherein the cooling comprises cooling to a temperature at or below ambient temperature.

22. The process of claim 14, further comprising adding water or aqueous hydrochloric acid to quench the reaction after cooling the reaction mixture, wherein the adding water or hydrochloric acid is performed at a temperature not to exceed 50° C.

\* \* \* \* \*